United States Patent
Frey et al.

(10) Patent No.: US 10,378,003 B2
(45) Date of Patent: Aug. 13, 2019

(54) TAG REMOVAL FROM PROTEINS EXPRESSED IN PRO- AND EUKARYOTIC HOSTS

(71) Applicant: MAX-PLANCK-GESELLSCHAFT ZUR FOERDERUNG DER WISSENSCHAFTEN E.V, Munich (DE)

(72) Inventors: Steffen Frey, Goettingen (DE); Dirk Goerlich, Goettingen (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 26 days.

(21) Appl. No.: 15/525,487

(22) PCT Filed: Nov. 10, 2015

(86) PCT No.: PCT/EP2015/076218
§ 371 (c)(1),
(2) Date: May 9, 2017

(87) PCT Pub. No.: WO2016/075143
PCT Pub. Date: May 19, 2016

(65) Prior Publication Data
US 2018/0195056 A1     Jul. 12, 2018

(30) Foreign Application Priority Data
Nov. 10, 2014   (EP) .................................. 14192557

(51) Int. Cl.
*C12N 9/64*     (2006.01)
*C07K 1/22*     (2006.01)
*C12N 9/50*     (2006.01)

(52) U.S. Cl.
CPC .............. *C12N 9/641* (2013.01); *C07K 1/22* (2013.01); *C12N 9/50* (2013.01); *C12N 9/6405* (2013.01)

(58) Field of Classification Search
CPC ............................... C12N 9/641; C12Y 304/22
See application file for complete search history.

(56) References Cited

FOREIGN PATENT DOCUMENTS

| WO | WO 02/090495 A2 | 11/2002 |
| WO | WO 03/057174 A2 | 7/2003 |
| WO | WO 2005/003313 A2 | 1/2005 |
| WO | WO 2006/073976 A2 | 7/2006 |
| WO | WO 2008/083271 A2 | 7/2008 |
| WO | WO 2015/049230 A1 | 4/2015 |

OTHER PUBLICATIONS

Hellsten et al. 2010; The genome of the Western clawed from Xenopus tropicalis. Science. 238: 633-636, with sequence alignment.*
Xenopus Gene Collection Project. 2004; Accession No. Q640G7.*
Shu et al. 2010; Synthetic substrates for measuring activity of autophagy proteases autophagins (Atg4). Autophagy 6(7): 936-947.*
Arnau et al., "Current strategies for the use of affinity tags and tag removal for the purification of recombinant proteins," Protein Expr. Purif., vol. 48, 2006 (available online Dec. 28, 2005), pp. 1-13.
Blow et al., "Initiation of DNA replication in nuclei and purified DNA by a cell-free extract of Xenopus eggs," Cell, vol. 47, Nov. 21, 1986, pp. 577-587.
Butt et al., "SUMO fusion technology for difficult-to-express proteins," Protein Expr. Purif., vol. 43, 2005 (available online Apr. 9, 2005), pp. 1-9.
Conzelmann et al., "A major 125-kd membrane glycoprotein of *Saccharomyces cerevisiae* is attached to the lipid bilayer through an inositol-containing phospholipid," EMBO J., vol. 7. No. 7, 1988, pp. 2233-2240.
Database UNIPARC [Online], "Protein fig|8364.3.peg.17647: *Xenopus tropicalis* (western clawed frog)," EBI Accession No. UNIPARC:UPI00004D3CE0, Mar. 19, 2013, XP002754660, 1 page.
Database Uniprot [Online], "RecName: Full=Cysteine protease ATG4B; EC=3.4.22.-; AltName: Full=Autophagy-related protein 4 homolog B," EBI Accession No. UNIPROT: Q640G7, Mar. 15, 2005, XP002754661, 1 page.
Enke, "Towards a recombinant in vitro translation system from wheat," Georg-August-Universität Göttingen, Jun. 2010, pp. 1-134 (144 pages total).
Frey et al., "A new set of highly efficient, tag-cleaving proteases for purifying recombinant proteins," Journal of Chromatography A, vol. 1337, 2014 (available online Feb. 19, 2014), pp. 95-105.
Frey el al., "Purification of protein complexes of defined subunit stoichiometry using a set of orthogonal, tag-cleaving proteases," Journal of Chromatography A, vol. 1337, 2014 (available online Feb. 19, 2014), pp. 106-115.
Frey et al., "The Xenopus laevis Atg4B Protease: Insights into Substrate Recognition and Application for Tag Removal from Proteins Expressed in Pro- and Eukaryotic Hosts," PLoS One, vol. 10, No. 4, e0125099, Apr. 29, 2015, pp. 1-25.
Griesbeck et al., "Reducing the Environmental Sensitivity of Yellow Fluorescent Protein," J Biol Chem., vol. 276, No. 31, Aug. 3, 2001 (published online May 31, 2001), pp. 29188-29194 (8 pages total).

(Continued)

*Primary Examiner* — Karen Cochrane Carlson
(74) *Attorney, Agent, or Firm* — Birch, Stewart, Kolasch & Birch, LLP

(57) ABSTRACT

The present invention belongs to the field of biotechnology. More specifically, the present invention provides a protease, a non-naturally occurring fusion protein comprising a corresponding protease recognition site, expression vectors encoding same, host cells comprising said expression vectors, kit of parts as well as methods applying the protease, fusion protein, and uses thereof, as defined in the claims. The presently disclosed protease/protease recognition site is particularly useful in methods requiring an orthogonal set of proteases, and is suitable for use in both prokaryotic and selected eukaryotic expression systems.

14 Claims, 13 Drawing Sheets

Specification includes a Sequence Listing.

(56) References Cited

OTHER PUBLICATIONS

Heikal et al., "Molecular spectroscopy and dynamics of intrinsically fluorescent proteins: Coral red (dsRed) and yellow (Citrine)," PNAS, vol. 97, No. 22, Oct. 24, 2000, pp. 11996-12001 (7 pages total).

Hemelaar et al., "A Single Protease, Apg4B, Is Specific for the Autophagy-related Ubiquitin-like Proteins GATE-16, MAP1-LC3, GABARAP, and Apg8L," J Biol Chem., vol. 278, No. 51, Dec. 19, 2003 (published online Oct. 6, 2003), pp. 51841-51850 (11 pages total).

Kabeya et al., "LC3, GABARAP and GATE16 localize to autophagosomal membrane depending on form-II formation,"J Cell Sci., vol. 117, No. 13, 2004, pp. 2805-2812.

Kapust et al., "Tobacco etch virus protease: mechanism of autolysis and rational design of stable mutants with wild-type catalytic proficiency," Protein Engineering, vol. 14, No. 12, 2001, pp. 993-1000.

Kumanomidou et al., "The Crystal Structure of Human Atg4b, a Processing and De-conjugating Enzyme for Autophagosome-forming Modifiers," J. Mol. Biol., vol. 355, 2006 (available online Nov. 28, 2005), pp. 612-618.

Li et al., "A new protease required for cell-cycle progression in yeast," Nature, vol. 398, Mar. 18, 1999, pp. 246-251.

Li et al., "Kinetics Comparisons of Mammalian Atg4 Homologues Indicate Selective Preferences toward Diverse Atg8 Substrates," J Biol Chem., vol. 286, No. 9, Mar. 4, 2011 (published online Dec. 22, 2010), pp. 7327-7338 (13 pages total).

Liu et al., "Enhanced protein expression in the baculovirus/insect cell system using engineered SUMO fusions," Protein Expr. Purif., vol. 62, 2008 (available online Aug. 5, 2008), pp. 21-28.

Malakhov et al., "SUMO fusions and SUMO-specific protease for efficient expression and purification of proteins," J Struct Funct Genomics, vol. 5, 2004, pp. 75-86.

Mariño et al., "Human autophagins, a family of cysteine proteinases potentially implicated in cell degradation by autophagy," J Biol Chem., vol. 278, No. 6, Feb. 7, 2003 (published online Nov. 21, 2002), pp. 3671-3678 (9 pages total).

Nilsson et al., "Affinity Fusion Strategies for Detection, Purification, and Immobilization of Recombinant Proteins," Protein Expr. Purif., vol. 11, Oct. 1997, pp. 1-16.

Peroutka et al., "Enhanced protein expression in mammalian cells using engineered SUMO fusions: Secreted phospholipase $A_2$, " Protein Sci., vol. 17, 2008, pp. 1586-1595.

Renicke et al., "A Tobacco Etch Virus Protease with Increased Substrate Tolerance at the P1' position,"PLoS One, vol. 8, Issue 6, e67915, Jun. 24, 2013, pp. 1-12.

Riezman et al., "Import of proteins into mitochondria: a 70 kilodalton outer membrane protein with a large carboxy-terminal deletion is still transported to the outer membrane," EMBO J., vol. 2, No. 12, 1983, pp. 2161-2168.

Satoo et al., "The structure of Atg4B-LC3 complex reveals the mechanism of LC3 processing and delipidation during autophagy,"EMBO J. vol. 28, No. 9, 2009 (published online Mar. 26, 2009), pp. 1341-1350.

Shu et al., "Synthetic substrates for measuring activity of autophagy proteases: autophagins (Atg4)," Autophagy, vol. 6, Issue 7, Oct. 1, 2010, pp. 936-947.

Sugawara et al., "Structural Basis for the Specificity and Catalysis of Human Atg4B Responsible for Mammalian Autophagy," J Biol Chem., vol. 280, No. 48, Dec. 2, 2005 (published online Sep. 23, 2005), pp. 40058-40065 (9 pages total).

Tanida et al., "HsAtg4B/HsApg4B/Autophagin-1 Cleaves the Carboxyl Termini of Three Human Atg8 Homologues and Delipidates Microtubule-associated Protein Light Chain 3- and GABAA Receptor-associated Protein-Phospholipid Conjugates," J Biol. Chem., vol. 279, No. 35, Aug. 27, 2004 (published online Jun. 8, 2004), pp. 36268-36276 (10 pages total).

Taxis et al., "Efficient protein depletion by genetically controlled deprotection of a dominant N-degron," Mol. Syst. Biol., vol. 5, Article No. 267, Apr. 28, 2009, pp. 1-7.

Taxis et al., "TIPI: TEV Protease-Mediated Induction of Protein Instability," Methods Mol Biol., vol. 832, 2012, pp. 611-626.

UNIPROT, "UniProtKB—Q640G7 (ATG4B_XENLA)," http://www.uniprot.org/uniprot/Q640G7, Mar. 15, 2005, 5 pages.

Urabe et al., "A Switching System Regulating Subcellular Localization of Nuclear Proteins Using a Viral Protease," Biochem Biophys Res Commun., vol. 266, No. 1, 1999, pp. 92-96.

Van Den Berg et al., "Improved solubility of TEV protease by directed evolution," Journal of Biotechnology, vol. 121, 2006, pp. 291-298.

Van Der Veen et al., "Ubiquitin-like proteins," Annu. Rev. Biochem., vol. 81, 2012 (published online Mar. 9, 2012), pp. 323-357.

Woo et al., "Differential processing of *Arabidopsis* ubiquitin-like Atg8 autophagy proteins by Atg4 cysteine proteases," PNAS, vol. 111, No. 2, Jan. 14, 2014 (corrections issued on Jun. 24, 2014), pp. 863-868 (7 pages total).

Yeh et al., "Ubiquitin-like proteins: new wines in new bottles," Gene, vol. 248, 2000, pp. 1-14.

Young et al., "Recombinant protein expression and purification: A comprehensive review of affinity tags and microbial applications," Biotechnol. J., vol. 7, 2012, pp. 620-634.

\* cited by examiner ic applica-
TAG REMOVAL FROM PROTEINS EXPRESSED IN PRO- AND EUKARYOTIC HOSTS The present invention belongs to the field of biotechnology. More specifically, the present invention provides a protease, a non-naturally occurring fusion protein comprising a corresponding protease recognition site, expression vectors encoding same, host cells comprising said expression vectors, kit of parts as well as methods applying the protease, fusion protein, and uses thereof, as defined in the claims. The presently disclosed protease/protease recognition site is particularly useful in methods requiring an orthogonal set of proteases, and is suitable for use in both prokaryotic and eukaryotic expression systems.

BACKGROUND OF THE INVENTION

Macroautophagic self-degradation (hereafter autophagy) is a common response of eukaryotic cells to stress stimuli like starvation or pathogen infection. Generally, bulk cytoplasm is non-selectively enclosed in autophagosomes, which are double membrane vesicles that fuse with lysosomes or the vacuole for degradation or recycling of the engulfed components. However, also specific targets can be degraded via receptors and adaptor proteins. During autophagosome formation, small ubiquitin-like proteins (UBLs) of the Atg8 family are covalently attached via their C-terminal Gly residue to phosphatidylethanolamine (PE) lipids on the autophagosomal membrane. Although it is clear that Atg8 lipidation and tethering to the autophagosomal membrane is essential for autophagosome biogenesis, the precise mechanism of Atg8 function so far remains elusive. Unlike S. cerevisiae that has only one Atg8 homolog, mammals encode two families of paralogous Atg8-like proteins (LC3 and GABARAP/GATE16) that may each contain several members and act as protein binding scaffolds in distinct steps of autophagosome formation. All Atg8 family members are structurally similar. Their structured core domain consists of an β-grasp fold preceded by two additional N-terminal α-helices and represents a versatile protein interaction surface that is essential for recruitment of the autophagy machinery to the autophagosomal membrane. The characteristic and flexible C-terminus ends with Phe-Gly (FG) or Tyr-Gly (YG). It is generated by Atg4 proteases that cleave C-terminally extended precursors. This group of highly specific proteases is also responsible for deconjugating Atg8 proteins from phosphatidylethanolamine (PE), a process that is required at a late stage of autophagosome formation.

As for Atg8, several paralogous Atg4-like proteases exist in higher eukaryotes, which might have different specificities for Atg8 paralogs (Li, M., Hou, Y., Wang, J., Chen, X., Shao, Z. M. and Yin, X. M. (2011) *J Biol Chem* 286, 7327-7338; Woo, J., Park, E. and Dinesh-Kumar, S. P. (2014) *Proc Natl Acad Sci USA* 111, 863-868). Amongst the four human Atg4 paralogs (Atg4A-D (Hemelaar, J., Lelyveld, V. S., Kessler, B. M. and Ploegh, H. L. (2003) *J Biol Chem* 278, 51841-51850; Kabeya, Y., Mizushima, N., Yamamoto, A., Oshitani-Okamoto, S., Ohsumi, Y. and Yoshimori, T. (2004) *J Cell Sci* 117, 2805-2812; Marino, G., Uria, J. A., Puente, X. S., Quesada, V., Bordallo, J. and Lopez-Otin, C. (2003) *J Biol Chem* 278, 3671-3678; Tanida, I., Sou, Y. S., Ezaki, J., Minematsu-Ikeguchi, N., Ueno, T. and Kominami, E. (2004) *J Biol Chem* 279, 36268-36276), Atg4B is the most versatile and active enzyme on recombinant fusion proteins. It can process the human Atg8 paralogs LC3B, GATE16, GABARAP and Atg8L with similar efficiencies (Li, M., Hou, Y., Wang, J., Chen, X., Shao, Z. M. and Yin, X. M. (2011) *J Biol Chem* 286, 7327-7338). The other three Atg4 enzymes are catalytically substantially less active. Solved structures of the free human Atg4B (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065) and LC3B-bound Atg4B (Satoo, K., Noda, N. N., Kumeta, H., Fujioka, Y., Mizushima, N., Ohsumi, Y. and Inagaki, F. (2009) *EMBO J* 28, 1341-1350) show that the protease has a papain-like fold with an additional unique domain participating in the protease's interaction with the folded substrate domain. The flexible C-terminus of Atg8-like substrates makes additional contacts to a pocket on the protease surface that directs the substrates' C-terminal Gly residues into active site. The protease's flexible N-terminus may fold back onto the substrate-binding pocket and has therefore been suggested to negatively regulate substrate interaction (Satoo, K., Noda, N. N., Kumeta, H., Fujioka, Y., Mizushima, N., Ohsumi, Y. and Inagaki, F. (2009) *EMBO J* 28, 1341-1350). The human Atg4B protease also contains a flexible extension at the C-terminus. In substrate-free structures (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065), this extension is poorly resolved and folds back on the substrate interaction surface, which might suggest that it interferes with substrate binding. To obtain crystals of substrate-bound Atg4B, the C-terminal extension had to be deleted (Satoo, K., Noda, N. N., Kumeta, H., Fujioka, Y., Mizushima, N., Ohsumi, Y. and Inagaki, F. (2009) *EMBO J* 28, 1341-1350). Its functional relevance so far remained elusive. Atg8-like proteins represent only one class of UBLs. This larger group of small protein modifiers also includes the founding member ubiquitin, SUMO and NEDD8 that act as regulators of various intracellular processes (reviewed in van der Veen, A. G. and Ploegh, H. L. (2012) *Annu Rev Biochem* 81, 323-357; and Yeh, E. T., Gong, L. and Kamitani, T. (2000) *Gene* 248, 1-14). In contrast to Atg8-like proteins, other UBLs, however, generally possess a C-terminal Gly-Gly (GG) motif and are conjugated to proteins by isopeptide bonds formed between their C-terminal carboxyl group primary amine groups on the surface of target proteins. Importantly, all mentioned UBLs are initially processed and often deconjugated by dedicated proteases (van der Veen, A. G. and Ploegh, H. L. (2012) *Annu Rev Biochem* 81, 323-357). In most cases, these proteases are highly efficient, which can be exploited for biochemical applications. The yeast SUMO specific protease Ulp1, for example, has successfully been used for the in vitro tag-removal from recombinant proteins (Malakhov, M. P., Mattern, M. R., Malakhova, O. A., Drinker, M., Weeks, S. D. and Butt, T. R. (2004) *J Struct Funct Genomics* 5, 75-86). Recently, the inventors characterized additional UBL-specific proteases and found that the *Brachypodium distachyon* (bd) SUMO- and NEDD8-specific proteases bdSENP1 and bdNEDP1 remove tags even more robustly and with an up to 1000 times higher efficiency than TEV protease (Frey, S. and Görlich, D. (2014) *J Chromatogr A* 1337, 95-105; Frey, S. and Görlich, D. (2014) *J Chromatogr A* 1337, 106-115). Importantly, bdSENP1 and bdNEDP1 display mutually exclusive (i.e. orthogonal) substrate specificity and can thus be used for the highly efficient purification of recombinant proteins and stoichiometric protein complexes by on-column or post-column cleavage (Frey, S. and Görlich, D. (2014) *J Chromatogr A* 1337, 95-105; Frey, S. and Görlich, D. (2014) *J Chromatogr A* 1337, 106-115). The application of UBL-specific proteases in eukaryotic systems is typically hampered by cross-reactivity with endogenous UBL-processing enzymes. Recently, the SUMO variant SUMOstar has been introduced, which allows purification of recombinant fusion proteins also from eukaryotic hosts (Liu, L., Spurrier, J., Butt, T. R. and Strickler, J. E. (2008) *Protein Expr Purif* 62, 21-28; Peroutka, R. J., Elshourbagy, N., Piech, T. and Butt, T. R. (2008) *Protein Sci* 17, 1586-1595). Further UBL substrates that are stable in eukaryotic hosts might become valuable tools that can be used for the purification of protein complexes (Frey, S. and Görlich, D. (2014) *J Chromatogr A* 1337, 106-115). In other applications, such substrates may be used for the induced in-vivo cleavage of recombinant fusion upon intracellular expression of the respective protease. Such in-vivo manipulation can e.g. be applied to modify the stability or localization of a protein of interest (Taxis, C. and Knop, M. (2012) *Methods Mol Biol* 832, 611-626; Urabe, M., Kume, A., Takahashi, T., Serizawa, N., Tobita, K. and Ozawa, K. (1999) *Biochem Biophys Res Commun* 266, 92-96; Taxis, C., Stier, G., Spadaccini, R. and Knop, M. (2009) *Mol Syst Biol* 5, 267). Tag-removing proteases are powerful tools in protein biochemistry. Although several proteases are routinely used for this purpose (Malakhov, M. P., Mattern, M. R., Malakhova, O. A., Drinker, M., Weeks, S. D. and Butt, T. R. (2004) *J Struct Funct Genomics* 5, 75-86; Butt, T. R., Edavettal, S. C., Hall, J. P. and Mattern, M. R. (2005) *Protein Expr Purif* 43, 1-9; Arnau, J., Lauritzen, C., Petersen, G. E. and Pedersen, J. (2006) *Protein Expr Purif* 48, 1-13; Li, S. J. and Hochstrasser, M. (1999) *Nature* 398, 246-251; Nilsson, J., Stahl, S., Lundeberg, J., Uhlen, M. and Nygren, P. A. (1997) *Protein Expr Purif* 11, 1-16; Young, C. L., Britton, Z. T. and Robinson, A. S. (2012) *Biotechnol J* 7, 620-634), most of them have severe drawbacks including low specific activity, limited specificity or strict constraints concerning temperature, buffer requirements or sequence context. Recent work from the inventors has introduced bdSENP1 and bdNEDP1, two new proteases that are largely devoid of these limitations (Frey, S. and Görlich, D. (2014) *J Chromatogr A* 1337, 95-105). The inventors recently also described the application of the *S. cerevisiae* (sc) Atg4 protease for tag removal (Frey, S. and Görlich, D. (2014) *J Chromatogr A* 1337, 95-105). scAtg4 is highly active in vitro and displays mutually exclusive cleavage specificity to SUMO, NEDD8 and ubiquitin-processing enzymes. Unfortunately, however, neither this protease nor scAtg8 fusion proteins are well behaved in terms of solubility and/or expression level.

WO 2002/090495, WO 2003/057174, WO 2005/003313, and WO 2006/073976 disclose the use of SUMO and other UBLs for increasing expression levels of proteins. WO 2005/003313 and WO 2008/083271 further mention that UBLs can be cleaved using SUMO proteases.

The amino acid sequence of xlAtg4B is known from UniProt sequence Q640G7. It is an object of the present invention to provide new proteases that could potentially be used for tag removal. More specifically, the inventors were interested to find well-behaved and stable protease fragments with optimal proteolytic activity.

SUMMARY OF THE INVENTION

The inventors now identified a seemingly optimal alternative to scAtg4, *Xenopus laevis* (xl) Atg4B protease (xlAtg4B) along with its substrates xlLC3B and xlGATE16 (FIG. 1). Fusions to both xlLC3B and xlGATE16 can be highly over-expressed in *E. coli* without impairing their solubility. Similarly, recombinant xlAtg4B can be produced in high yield. The inventors found compelling evidence that the so far uncharacterized C-terminal extension of xlAtg4B is crucially involved in recognition of xlLC3B and xlGATE16 substrates. The inventors identified an optimized fragment of xlAtg4B (xlAtg4B$^{14-384}$) that combines robust substrate interaction and cleavage with high thermal stability (FIGS. 4-7). xlAtg4B$^{14-384}$ is extraordinarily salt tolerant (FIG. 5A), has a high promiscuity for residues in the P$_1$' position (FIG. 8) and cleaves its substrates also at low temperatures (e.g. FIG. 4). At 0° C., xlAtg4B has a turnover rate similar to bdNEDP1 and is thus ≈30- to 50-fold more active than TEV protease (Frey, S. and m Görlich, D. (2014) *J Chromatogr A* 1337, 95-105). xlAtg4B has superior properties to its yeast homolog scAtg4 in terms of expression, solubility and thermal stability (FIG. 3, FIG. 7).

Accordingly, the present disclosure provides a protease comprising an amino acid sequence with at least 80% identity over amino acids 25-384 of SEQ ID NO: 1 (xlAtg4B), with the proviso that the protease is not the protease of SEQ ID NO: 1, wherein said protease is capable of cleaving the protease recognition site (PRS) according to SEQ ID NO: 2 (xlLC3B) with at least 20% activity as compared to the parent protease with the amino acid sequence of SEQ ID NO: 1, if tested using a native substrate protein shown in SEQ ID NO: 3 (His$_{14}$-xlLC3B-MBP) and 500 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT and/or wherein said protease is capable of cleaving the protease recognition site (PRS) according to SEQ ID NO: 4 (xlGATE16) with at least 20% activity as compared to the parent protease with the amino acid sequence of SEQ ID NO: 1, if tested using 500 nM of said protease and a native substrate protein shown in SEQ ID NO: 5 (His$_{14}$-xlGATE16-MBP) at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

Correspondingly, the present disclosure further provides a non-naturally occurring fusion protein, comprising a protease recognition site (PRS), which PRS comprises, preferably consists of
 (I) an amino acid sequence as shown in SEQ ID NO: 2 (xlLC3B); or
 (ii) a derivative of (i) with an amino acid sequence having at least 75% identity over the full length of SEQ ID NO: 2 (xlLC3B),
  wherein the protease shown in SEQ ID NO: 1 (xlAtg4B) is capable of cleaving said PRS derivative with at least 20% activity as compared to when using the amino acid sequence of SEQ ID NO: 2 (xlLC3B), under identical conditions of 1 hour incubation at 0° C., 500 nM protease, 100 µM initial concentration of substrate protein in a buffer consisting of 250 mM NaCl, 40 mM Tris/HCl pH 7.5, 2 mM MgCl$_2$, 250 mM sucrose, 2 mM DTT.

Also described is a non-naturally occurring fusion protein, comprising a protease recognition site (PRS), which PRS comprises, preferably consists of
 (i) an amino acid sequence as shown in SEQ ID NO: 4 (xlGATE16); or (ii) a derivative of (i) with an amino acid sequence having at least 75% identity over the full length of SEQ ID NO: 4 (xlGATE16), wherein the protease shown in SEQ ID NO: 1 (xlAtg4B) is capable of cleaving said PRS derivative with at least 20% activity as compared to when using the amino acid sequence of SEQ ID NO: 4 (xl-GATE16), under identical conditions of 1 hour incubation at 0° C., 200 nM protease, 100 µM initial concentration of substrate protein in a buffer consisting of 250 mM NaCl, 40 mM Tris/HCl pH 7.5, 2 mM $MgCl_2$, 250 mM sucrose, 2 mM DTT.

Also disclosed is an expression vector, comprising a multiple cloning site in functional linkage with a nucleic acid sequence encoding such a protease recognition site as comprised in the above fusion protein.

Likewise, there is provided an expression vector, comprising a nucleic acid sequence encoding the fusion protein of the disclosure.

The xlAtg4B substrates xlLC3B and xlGATE16 (FIG. 1) and the bdNEDP1 substrate bdNEDD8 greatly promote expression and solubility of proteins fused to their C-terminus in *E. coli* (FIG. 2, FIG. 9E). xlAtg4B protease allows to purify target proteins from xlLC3B or xlGATE16 fusions expressed in *E. coli* by a single sequence of affinity capture and proteolytic release (FIG. 9). Highly efficient tag removal by xlAtg4B[14-384] can be performed in solution (e.g. FIG. 4) or on-column (FIGS. 9 and 12). Similar purifications of bdNEDD8- and bdSUMO-tagged proteins using bdNEDP1 or bdSENP1 have already been described (WO 2015/049230). Since xlAtg4B[14-384] is orthogonal to TEV protease, bdSENP1, bdNEDD8, xlUsp2 and SUMOstar protease (FIG. 10), it can be used for the purification of protein complexes with defined subunit stoichiometry by sequential affinity capture and proteolytic release steps as described in WO 2015/049230 and Frey and Görlich (2014) *J Chromatogr A* 1337, 106-115).

A major limitation of available highly efficient protease systems for tag removal is that fusions of the recognized UBLs to the target protein are intrinsically instable in eukaryotic hosts due to the presence of endogenous proteases. Here, it is shown that xlLC3B and xlGATE16 fusions are stable in wheat germ extract (FIG. 11). Furthermore, full-length xlLC3B and bdNEDD8 fusion proteins can be produced in *S. cerevisiae* (FIG. 11).

Similar to the already known SUMOstar protease/SUMOstar system, the xlAtg4B/xlLC3B- and bdNEDP1/bdNEDD8-systems can be used for purification of target proteins from eukaryotic hosts (FIG. 12). Amongst SUMOstar, bdNEDD8 and xlLC3B fusions, the xlLC3B fusion is the only one that seems completely stable upon expression in *S. cerevisiae*. xlLC3B fusions can therefore be used for protein expression and induced in-vivo manipulation of fusion proteins in selected eukaryotic hosts.

Accordingly, the present disclosure further provides a host cell, comprising an expression vector as defined above.

Further disclosed is the use of the protease of the disclosure for removing a protein tag, preferably wherein the protein tag is an affinity tag; and the use of an expression vector as disclosed herein or of a host cell as disclosed herein in the production of a fusion protein in a eukaryotic expression system.

The disclosure further describes a method for purifying a stoichiometric protein is complex composed of at least two subunits from a mixture, said mixture comprising said protein complex and monomers of said at least two subunits, wherein said at least two subunits comprised in said mixture each comprise an N-terminal affinity tag (AT) separated from the subunit by a protease recognition site (PRS), wherein the ATs of each of said at least two subunits differ from each other and allow affinity chromatography being selective for each AT, and wherein the PRS of each of said at least two subunits is cleavable by a protease, which protease is orthogonal to the PRS of the other subunit(s), wherein the method comprises the steps of
a) subjecting the mixture to a first affinity chromatography selective for the AT of the first of said at least two subunits, whereby
   (i) the protein complex binds to the affinity resin via the AT of the first subunit, and
   (ii) impurities are washed off the column, and
   (iii) the protein complex is eluted from the column and the AT of the first subunit is cleaved off, or the protein complex is eluted by on-column cleavage, using said orthogonal protease which is specific for the PRS of said first subunit, and
   (iv) optionally removing the cleaved off AT of the first subunit; and
b) subjecting the eluate from step a) to a second affinity chromatography selective for the AT of the second of said at least two subunits, whereby
   (i) the protein complex binds to the affinity resin via the AT of the second subunit, and
   (ii) impurities are washed off the column, and
   (iii) the protein complex is eluted from the column and the AT of the second subunit is cleaved off, or the protein complex is eluted by on-column cleavage, using said orthogonal protease which is specific for the PRS of said second subunit, and
   (iv) optionally removing the cleaved off AT of the second subunit;

characterized in that one PRS comprises, preferably consists of
(i) an amino acid sequence as shown in SEQ ID NO: 2 (xlLC3B); or
(ii) a derivative of (i) with an amino acid sequence having at least 75% identity over the full length of SEQ ID NO: 2 (xlLC3B), wherein the protease shown in SEQ ID NO: 1 (xlAtg4B) is capable of cleaving said PRS derivative with at least 20% activity as compared to when using the amino acid sequence of SEQ ID NO: 2 (xlLC3B), under identical conditions of 500 nM protease, 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; or (i) an amino acid sequence as shown in SEQ ID NO: 4 (xlGATE16); or
(ii) a derivative of (i) with an amino acid sequence having at least 75% identity over the full length of SEQ ID NO: 4 (xlGATE16), wherein the protease shown in SEQ ID NO: 1 (xlAtg4B) is capable of cleaving said PRS derivative with at least 20% activity as compared to when using the amino acid sequence of SEQ ID NO: 4 (xl-GATE16), under identical conditions of 200 nM protease, 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; and wherein the AT of the subunit comprising said PRS is cleaved off using a protease according to the present disclosure.

Also provided is a kit of parts, comprising (i) the protease according to the present disclosure, and (ii) an expression vector as disclosed herein or a host cell as disclosed herein.

Further provided is a kit of parts, comprising
(i) the protease according to the present disclosure, and at least one protease selected from the group of proteases consisting of
(ii) a protease having an amino acid sequence with at least 45% identity over the full length of SEQ ID NO: 11 (bdSENP1),
  wherein said protease is capable of cleaving the PRS according to ID NO: 10 (bdSUMO) with at least 20% activity as compared to the parent protease of SEQ ID NO: 10 (bdSENP1), if tested using a native substrate protein shown in SEQ ID NO: 8 (His$_{14}$-bdSUMO-MBP) and 30 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT;
  preferably wherein the protease comprises the amino acid sequence shown as amino acids 1-224 in SEQ ID NO: 11 (bdSENP1$^{248-481}$);
  more preferably wherein the protease consists of the amino acid sequence shown as amino acids 1-224 in SEQ ID NO: 11 (bdSENP1$^{248-481}$);
(iii) a protease having an amino acid sequence with at least 35% identity over the full length of SEQ ID NO: 13 (bdNEDP1),
wherein said protease cleaves the PRS according to SEQ ID NO: 12 (bdNEDD8) with at least 20% activity as compared to the parent protease of SEQ ID NO: 13 (bdNEDP1), if tested using a native substrate protein shown in SEQ ID NO: 7 (His$_{14}$-bdNEDD8-MBP) and 300 nM of said protease at standard conditions 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT;
  preferably wherein the protease comprises the amino acid sequence as shown in SEQ ID NO: 13 (bdNEDP1);
  more preferably wherein the protease consists of the amino acid sequence as shown in SEQ ID NO: 13 (bdNEDP1);
(iv) a protease having an amino acid sequence with at least 80% identity over the full length of SEQ ID NO: 15 or 16,
  wherein said protease is capable of cleaving the PRS according to SEQ ID NO: 14 (TEV) with at least 20% activity as compared to the parent protease of SEQ ID NO: 15 or 16, if tested using a native substrate protein shown in SEQ ID NO: 6 (His$_{10}$-ZZ-TEV-MBP) and 10 µM of said protease at standard conditions 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT;
  preferably wherein the protease comprises the amino acid sequence as shown in SEQ ID NO: 15 or 16,
  more preferably wherein the protease consists of the amino acid sequence as shown in SEQ ID NO: 15 or 16;
(v) a protease having an amino acid sequence with at least 80% identity over the full length of SEQ ID NO: 18 (xlUsp2),
  wherein said protease is capable of cleaving the PRS according to ID NO: 17 (xlUb) with at least 20% activity as compared to the parent protease of SEQ ID NO: 18 (xlUsp2), if tested using a native substrate protein shown in SEQ ID NO: 9 (His$_{14}$-xlUb-MBP) and 1 µM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.
  preferably wherein the protease comprises the amino acid sequence as shown in SEQ ID NO: 18 (xlUsp2);
  more preferably wherein the protease consists of the amino acid sequence as shown in SEQ ID NO: 18 (xlUsp2);
(vi) a protease having an amino acid sequence with at least 80% identity over the full length of SEQ ID NO: 24 (SUMOstar protease),
  wherein said protease is capable of cleaving the PRS according to ID NO: 23 (SUMOstar) with at least 20% activity as compared to the parent protease as defined in (i), if tested using a native substrate protein shown in SEQ ID NO: 22 (His$_{14}$-SUMOstar-MBP) and 30 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT;
  preferably wherein the protease comprises the amino acid sequence as shown in SEQ ID NO: 24 (SUMOstar protease);
  more preferably wherein the protease consists of the amino acid sequence as shown in SEQ ID NO: 24 (SUMOstar protease).

The kit of parts can be used in a method of purifying stoichiometric protein complexes comprising at least two subunits, preferably a method as disclosed herein. Finally, the kit of parts can also be used for on-column cleavage in an affinity chromatography.

DETAILED DESCRIPTION OF THE PREFERRED EMBODIMENTS

Provided is a protease comprising an amino acid sequence with at least 80% identity, preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, more preferably 99% identity, and most preferably 99.5% identity over amino acids 25-384 of SEQ ID NO: 1 (xlAtg4B), with the proviso that the protease is not the protease of SEQ ID NO: 1.

In a preferred embodiment, the protease comprises an amino acid sequence with at least 80% identity, preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, more preferably 99% identity, and most preferably 99.5% identity to amino acids 14-384 of SEQ ID NO: 1 (xlAtg4B), more preferably wherein the protease comprises an amino acid sequence with at least 80% identity, preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, more preferably 99% identity, and most preferably 99.5% identity over the full length of SEQ ID NO: 1 (xlAtg4B). Still more preferably, the protease comprises the amino acid sequence of amino acids 25-384 of SEQ ID NO: 1 (xlAtg4B). In an even more preferred embodiment, the protease comprises the amino acid sequence of amino acids 14-384 of SEQ ID NO: 1 (xlAtg4B). In still a more preferred embodiment, the protease consists of the amino acid sequence of amino acids 25-384 of SEQ ID NO: 1 (xlAtg4B), and in a most preferred embodiment the protease consists of the amino acid sequence of amino acids 14-384 of SEQ ID NO: 1 (xlAtg4B). The protease may further comprise an affinity tag, preferably a poly-His tag, a MBP-tag or a ZZ-tag.

Said protease is capable of cleaving the protease recognition site (PRS) according to SEQ ID NO: 2 (xlLC3B) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to the parent protease with the amino acid sequence of SEQ ID NO: 1, if tested using a native substrate protein shown in SEQ ID NO: 3 (His$_{14}$-xlLC3B-MBP) and 500 nM of said protease at standard conditions of 1 hour incubation at 0° C., 100 μM initial concentration of substrate protein in a buffer consisting of 250 mM NaCl, 40 mM Tris/HCl pH 7.5, 2 mM MgCl$_2$, 250 mM sucrose, 2 mM DTT.

Alternatively, or in addition, said protease is capable of cleaving the protease recognition site (PRS) according to SEQ ID NO: 4 (xlGATE16) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to the parent protease with the amino acid sequence of SEQ ID NO: 1, if tested using 500 nM of said protease and a native substrate protein shown in SEQ ID NO: 5 (His$_{14}$-xlGATE16-MBP) at standard conditions of 1 hour incubation at 0° C., 100 μM initial concentration of substrate protein in a buffer consisting of 250 mM NaCl, 40 mM Tris/HCl pH 7.5, 2 mM MgCl$_2$, 250 mM sucrose, 2 mM DTT.

As used herein, an amino acid sequence is said to have "X % sequence identity with SEQ ID NO: Y" over a defined length of amino acids if the sequence in question is aligned with said SEQ ID NO: Y and the sequence identity between those to aligned sequences is at least X %. Such an alignment can be performed using for example publicly available computer homology programs such as the "BLAST" program, such as "blastp" provided at the NCBI homepage at ncbi.nlm.nih.gov/blast/blast.cgi, using the default settings provided therein. Subsequently, identical residues are determined, such as by counting by hand, and a subsequent calculation of the percentage identity (PID) by dividing the number of identities over the indicated length of SEQ ID NO: Y gives "X % sequence identity". If a particular length is not specifically indicated, the sequence identity is calculated over the entire/full length of SEQ ID NO: Y. Further methods of calculating sequence identity percentages of sets of polypeptides are known in the art.

Preferably, the nature of amino acid residue changes by which the polypeptide having at least X % identity to a reference sequence differs from said reference sequence is a semi-conservative and more preferably a conservative amino acid residue exchange.

| Amino acid | Conservative exchange | Semi-conservative exchange |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q; |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Changing from M to E, R or K is semi-conservative if the ionic tip of the new side group can reach the protein surface while the methylene groups make hydrophobic contacts. Changing from P to one of K, R, E or D is semi-conservative, if the side group is on the surface of the protein. Furthermore, the skilled person will appreciate that glycines at sterically demanding positions should not be substituted and that P should not be introduced into parts of the protein which have an alpha-helical or a beta sheet structure. Residues critical for the structure and activity of the PRS or protease, and which may therefore not be made subject of substitutions, can be identified by alanine-scanning mutagenesis, as generally known in the art.

In particular the protease fragments have advantageous properties as compared to the full-length wild-type protease, as demonstrated in the Examples and as is further described below.

For example, the protease exhibits high activity at low temperature. More specifically, the protease as disclosed herein is capable of cleaving at least 90% of a 100-fold, preferably 150-fold, more preferably 200-fold molar excess of a native substrate protein shown in SEQ ID NO: 3 (His$_{14}$-xlLC3B-MBP) at standard conditions of 1 hour incubation at 0° C., 100 μM initial concentration of substrate protein in a buffer consisting of 250 mM NaCl, 40 mM Tris/HCl pH 7.5, 2 mM MgCl$_2$, 250 mM sucrose, 2 mM DTT.

Moreover, the protease as disclosed herein also shows high activity at ambient temperatures. For example, the protease is capable of cleaving
  (i) at least 90% of a 500-fold, preferably 1000-fold, more preferably 1500-fold, most preferably 2000-fold molar excess of a native substrate protein shown in SEQ ID NO: 3 (His$_{14}$-xlLC3B-MBP); and/or
  (ii) at least 90% of a 2000-fold, preferably 3000-fold, more preferably 4000-fold, even more preferably 5000-fold, more preferably 6000-fold, most preferably 6600-fold molar excess of a native substrate protein shown in SEQ ID NO: 5 (His$_{14}$-xlGATE16-MBP);

at conditions of 1 hour incubation at 25° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

At the same time, the protease as disclosed herein shows great promiscuity in the P$_1$' position of the cleavage site. In particular, the protease is capable of cleaving at least 90%, more preferably 91%, more preferably 92%, more preferably 93%, more preferably 94%, and even more preferably 95% of a 100-fold molar excess of native substrate protein variants in which only residue 152 in SEQ ID NO: 3 (the P$_1$' position of His$_{14}$-xlLC3B-MBP) has been mutated to Met, Tyr, Arg or Glu relative to SEQ ID NO: 3 at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

Apart from the above, the protease shows good activity even at high salt conditions. For example, the protease is capable of cleaving at least 50%, preferably 55%, more preferably 60%, more preferably 65%, and most preferably at least 70% of a 200-fold molar excess of a native substrate protein as shown in SEQ ID NO: 3 (His$_{14}$-xlLC3B-MBP) within one hour at 0° C. at high-salt conditions of 100 µM initial concentration of substrate protein in a buffer consisting of 1.5 M NaCl, 40 mM Tris/HCl pH 7.5, 2 mM MgCl$_2$, 250 mM sucrose, 2 mM DTT. This property makes the protease particularly useful in certain methods of protein purification, as it may allow omission of salt reducing steps of dialysis or buffer exchange or the use of the protease in on-column cleavage. As shown in the Examples, if the protease does not comprise a polyHis-tag, the protease, is capable of cleaving a substrate protein as shown in SEQ ID NO: 25 (His$_{14}$-IF2d1-xlLC3B-MBP) immobilized on a Ni(II) chelate resin with at least 10%, preferably at least 20%, more preferably at least 30%, more preferably at least 40%, and most preferably at least 50% efficiency as compared to the non-immobilised substrate at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

As also shown in the Examples, the protease is highly specific and orthogonal to protease recognition sites of other proteases. Hence, in a preferred embodiment, the protease cleaves at stringent conditions any of the substrates shown in SEQ ID NO: 6 (His$_{10}$-ZZ-TEV-MBP), SEQ ID NO: 7 (His$_{14}$-bdNEDD8-MBP), SEQ ID NO: 8 (His$_{14}$-bdSUMO-MBP), SEQ ID NO: 9 (His$_{14}$-xlUb-MBP), or SEQ ID NO: 22 (His$_{14}$-SUMOstar-MBP) at least 10 000 fold less efficiently than the substrate shown in SEQ ID NO: 3 (His$_{14}$-xlLC3B-MBP), wherein stringent conditions are defined as 3 hour incubation at 25° C., 20 µM protease, 100 µM initial concentration of substrate protein in a buffer consisting of 250 mM NaCl, 40 mM Tris/HCl pH 7.5, 2 mM MgCl$_2$, 250 mM sucrose, 2 mM DTT. This property makes the protease useful in methods for purifying stoichiometric protein complexes, as further described below.

Finally, the protease of the disclosure also exhibits good thermal stability. Preferably, the protease retains at least 50%, more preferably at least 60%, more preferably at least 70%, more preferably at least 80%, more preferably at least 85% of its activity when pre-incubated for 16 h at 42° C. in the absence of oxygen in a buffer consisting of 250 mM NaCl, 40 mM Tris/HCl pH 7.5, 2 mM MgCl$_2$, 250 mM sucrose, 20 mM DTT, as compared to said non-treated protease, if tested using a native substrate protein shown in SEQ ID NO: 3 (His$_{14}$-xlLC3B-MBP) and 500 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

Correspondingly, the present disclosure further provides a non-naturally occurring fusion protein. In one embodiment, said fusion protein comprises a protease recognition site (PRS), which PRS comprises, preferably consists of
  (i) an amino acid sequence as shown in SEQ ID NO: 2 (xlLC3B); or
  (ii) a derivative of (i) with an amino acid sequence having at least 75% identity, preferably at least 80% identity, more preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, and more preferably 99% identity over the full length of SEQ ID NO: 2 (xlLC3B),
wherein the protease shown in SEQ ID NO: 1 (xlAtg4B) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to when using the amino acid sequence of SEQ ID NO: 2 (xlLC3B), under identical conditions of 1 hour incubation at 0° C., 500 nM protease, 100 µM initial concentration of substrate protein in a buffer consisting of 250 mM NaCl, 40 mM Tris/HCl pH 7.5, 2 mM MgCl$_2$, 250 mM sucrose, 2 mM DTT.

In another embodiment, said fusion protein comprises a protease recognition site (PRS), which PRS comprises, preferably consists of
  (i) an amino acid sequence as shown in SEQ ID NO: 4 (xlGATE16); or
  (ii) a derivative of (i) with an amino acid sequence having at least 75% identity, preferably at least 80% identity, more preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, and more preferably 99% identity over the full length of SEQ ID NO: 4 (xlGATE16),
wherein the protease shown in SEQ ID NO: 1 (xlAtg4B) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to when using the amino acid sequence of SEQ ID NO: 4 (xlGATE16), under identical conditions of 1 hour incubation at 0° C., 200 nM protease, 100 µM initial concentration of substrate protein in a buffer consisting of 250 mM NaCl, 40 mM Tris/HCl pH 7.5, 2 mM MgCl$_2$, 250 mM sucrose, 2 mM DTT.

The fusion protein preferably further comprises an affinity tag, wherein the affinity tag is located in the fusion so that it is cleaved off, if the fusion protein is incubated with the protease shown in SEQ ID NO: 1 (xlAtg4B). In a more preferred embodiment, the affinity tag is N-terminal from the PRS.

For preparing the fusion proteins described herein, the present disclosure further provides an expression vector, comprising a multiple cloning site in functional linkage with a nucleic acid sequence encoding the protease recognition site as defined above. In accordance with the above disclosure, the nucleic acid sequence may further encode an affinity tag. Once the protein of interest has been ligated into the multiple cloning site, an expression vector comprising a nucleic acid sequence encoding the fusion protein as disclosed herein is obtained. Said expression vector can then be transformed into a suitable host cell for producing the fusion protein.

Accordingly, also provided is a host cell, comprising an expression vector as disclosed above. As shown in the Examples using selected representative host cells, the PRS of the fusion protein disclosed herein is not cleaved in vivo in both prokaryotic host cells and selected eukaryotic host cells. In particular the latter is a surprising finding. Therefore, in a preferred embodiment, the host cell is a eukaryotic host cell, in particular a fungal cell or a plant cell. In one particularly preferred embodiment, the host cell is a fungal cell, preferably a yeast cell, more preferably the cell is of the genus *Saccharomyces*, even more preferably the host cell is a cell of *Saccharomyces cerevisiae*. In another particularly preferred embodiment, the host cell is a plant cell, preferably wherein said plant cell is a cell of the order Poales, more preferably wherein said cell is of the family Poaceae, even more preferably wherein said cell is of the subfamily Pooideae, still more preferably wherein said cell is of the tribe Triticeae, and most preferably, wherein said cell is of the genus *Triticum*. In case a prokaryotic expression system is used the host cell is preferably a cell of *Escherichia coli*.

The protease as disclosed herein may be used for removing a protein tag, preferably wherein the protein tag is an affinity tag, e.g. for on-column cleavage in an affinity chromatographic purification step. However, it is also contemplated that the protease may be used in vivo in a cell, e.g., in order to direct the fusion protein to a particular cell compartment, where the signal sequence is cleaved off. Thus, further contemplated is a host cell as disclosed herein, which further expresses a protease of the disclosure as defined above.

Taken together, the expression vector as disclosed above or a host cell a disclosed above can be used in the production of a fusion protein in a eukaryotic expression system. Moreover, these can be used in a method for purifying a stoichiometric protein complex.

Hence, also provided is a method for purifying a stoichiometric protein complex composed of at least two subunits from a mixture, said mixture comprising said protein complex and monomers of said at least two subunits, wherein said at least two subunits comprised in said mixture each comprise an N-terminal affinity tag (AT) separated from the subunit by a protease recognition site (PRS), wherein the ATs of each of said at least two subunits differ from each other and allow affinity chromatography being selective for each AT, and wherein the PRS of each of said at least two subunits is cleavable by a protease, which protease is orthogonal to the PRS of the other subunit(s), wherein the method comprises the steps of a) subjecting the mixture to a first affinity chromatography selective for the AT of the first of said at least two subunits, whereby (i) the protein complex binds to the affinity resin via the AT of the first subunit, and
(ii) impurities are washed off the column, and
(iii) the protein complex is eluted from the column and the AT of the first subunit is cleaved off, or the protein complex is eluted by on-column cleavage, using said orthogonal protease which is specific for the PRS of said first subunit, and
(iv) optionally removing the cleaved off AT of the first subunit; and b) subjecting the eluate from step a) to a second affinity chromatography selective for the AT of the second of said at least two subunits, whereby
(i) the protein complex binds to the affinity resin via the AT of the second subunit, and
(ii) impurities are washed off the column, and
(iii) the protein complex is eluted from the column and the AT of the second subunit is cleaved off, or the protein complex is eluted by on-column cleavage, using said orthogonal protease which is specific for the PRS of said second subunit, and
(iv) optionally removing the cleaved off AT of the second subunit;

characterized in that one PRS comprises, preferably consists of (i) an amino acid sequence as shown in SEQ ID NO: 2 (xlLC3B); or
(ii) a derivative of (i) with an amino acid sequence having at least 75% identity, preferably at least 80% identity, more preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, and more preferably 99% identity over the full length of SEQ ID NO: 2 (xlLC3B),
wherein the protease shown in SEQ ID NO: 1 (xlAtg4B) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to when using the amino acid sequence of SEQ ID NO: 2 (xlLC3B), under identical conditions of 500 nM protease, 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; or (i) an amino acid sequence as shown in SEQ ID NO: 4 (xlGATE16); or
(ii) a derivative of (i) with an amino acid sequence having at least 75% identity, preferably at least 80% identity, more preferably 85% identity, more preferably 90% identity, more preferably 91% identity, more preferably 92% identity, more preferably 93% identity, more preferably 94% identity, more preferably 95% identity, more preferably 96% identity, more preferably 97% identity, more preferably 98% identity, and more preferably 99% identity over the full length of SEQ ID NO: 4 (xlGATE16),
wherein the protease shown in SEQ ID NO: 1 (xlAtg4B) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100%, as compared to when using the amino acid sequence of SEQ ID NO: 4 (xlGATE16), under identical conditions of 200 nM protease, 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT; and wherein the AT of the subunit comprising said PRS is cleaved off using a protease according to the present disclosure.

Among the two PRSs, xlLC3B is preferred. In a most preferred embodiment, one PRS comprises, even more preferably consists of an amino acid sequence as shown in SEQ ID NO: 2 (xlLC3B).

In one embodiment, the stoichiometric protein complex is composed of at least two subunits. However, the stoichiometric protein complex may also be composed of three, four, five, six, seven, eight or nine subunits, which each differ from each other.

If the protein complex comprises a third subunit, one may incorporate a third affinity chromatography step. Such a third affinity chromatography step will further improve the purity, and it makes sure that only those complexes are purified, which contain all three subunits.

In this case, said third subunit comprised in said mixture comprises an N-terminal affinity tag (AT) separated from the subunit by a protease recognition site (PRS), wherein the AT of said third subunit differs from the AT of the other subunits and allows affinity chromatography being selective for the AT of said third subunit, and wherein the PRS of said third subunit is cleavable by a protease, which protease is orthogonal to the PRS of the other two subunits, further comprising after step b) and prior to optional step c) an additional step b') subjecting the eluate from step b) to an affinity chromatography selective for the AT of the third subunit, whereby
  (i) the protein complex binds to the affinity resin via the AT of the third subunit, and
  (ii) impurities (e.g. monomers) are washed off the column, and
  (iii) the protein complex is eluted from the column and the AT of the third subunit is cleaved off, or the protein complex is eluted by on-column cleavage, using said orthogonal protease which is specific for the PRS of said third subunit, preferably wherein the protein complex is eluted by on-column cleavage, and
  (iv) optionally removing the cleaved off AT of the third subunit.

If deemed appropriate, the method comprises the additional step of c) removing the protease from the eluate originating from the last affinity chromatography step. For example, step c) may be an affinity chromatography, a size exclusion chromatography, or a precipitation step, as generally known in the art. However, any method suitable for removing the protease from the eluate may be applied. In a preferred embodiment, the protease from the eluate originating from the last affinity chromatography prior to step c) comprises an affinity tag, preferably a poly-His tag or a ZZ tag, and step c) is an affinity chromatography step, whereby the protease binds to the affinity resin, and the protein complex is collected in the flow-through. Said affinity tag of the protease may be the same than one of the affinity tags used in the affinity chromatography steps a), b), or b'), but with the provisio that it differs from the affinity tag used in the directly preceding affinity chromatography step b), or b'. For example, the affinity tag of the final protease may be a polyHis-tag, and step c) is a Ni$^{2+}$-chelate affinity chromatography.

Preferably, the protein complex is eluted in step a) (iii) or step b) (iii) by on-column cleavage. More preferably both step a) (iii) and step b) (iii) are on-column cleavage steps. Likewise, if the method further comprises optional steps b') (iii), said step b') may be an on column-cleavage step. On-column cleavage offers several advantages. It not only makes purifications more time-efficient by avoiding any lengthy buffer exchange and reverse chromatography steps. On-column cleavage also allows the target proteins to be specifically released from the resin under very mild conditions: As the elution buffer differs from the washing buffer only by a minute amount of protease, on-column cleavage bypasses more drastic elution conditions as high concentrations of competitor, significant alterations in the buffer composition or pH changes. Most importantly, however, on-column cleavage potentiates the efficiency of protein purifications by elegantly combining the specificities of the affinity resin and the protease: Only proteins containing the proper affinity tag and the proper protease recognition site will be bound and consecutively released from the resin. In contrast, contaminant proteins non-specifically interacting with the resin and thus lacking the specific protease recognition site—will remain bound to the affinity resin during the elution step. Preferably, the most efficient orthogonal protease is used in the final affinity chromatography step, in order to keep the protease "contamination" in the final product low.

The term "stoichiometric protein complex" is intended to mean that each complex is composed of the same molar ratio of the same subunits, and that each complex has a definite identical size as defined by the number of subunits forming the complex. In very special cases one subunit A may form a complex comprising, e.g., either a subunit B or a subunit C, in which case there will be a mixture of stoichiometric protein complexes comprising subunits AB and complexes comprising subunits AC. However, a stoichiometric protein complex is to be distinguished from random protein aggregates, which are characterized by a random molar distribution, and which differ by its constituents.

The subunit(s) may further comprise a spacer between the AT and the PRS, and/or between the PRS and the subunit. In a preferred embodiment, the subunit(s) further comprise a spacer between the AT and the PRS. A typical spacer should be flexible and hydrophilic, without representing a substrate for endogenous proteases or comprising a PRS as defined herein. Usually, spacers having a high content of glycine and serine (as well as threonine and asparagine) are used. However, charged residues (especially negative charged residues) are not excluded. The skilled person will recognize suitable spacers.

The affinity tag (AT) may be any affinity tag suitable in the above-described method. In other words, any affinity tag may be used as long as it enables purification by affinity chromatography and as long as it is specific and does not interact with other affinity resins used in the method. For example, the AT may be a peptide tag, a covalent tag or a protein tag. Examples of a peptide tag are an Avi-tag, a CBP (calmodulin-binding peptide)-tag, a Flag-tag, a HA-tag, a polyHis-tag, a Myc-tag, a S-tag, a SBP-tag, a Softag 1, a Softag 3, a V5-tag, a Strep-tag or a Xpress-tag. Examples of a covalent tag are Isopeptag and Spytag. Examples for a protein tag are BCCP, GST-tag, GFP-tag, MBP-tag, NusA-tag, GFP-tag, ZZ-tag or a thioredoxin-tag. The AT may be selected from the group consisting of a polyHis-tag, ZZ-tag, FLAG-tag, HA-tag, GST-tag, GST-epitope tag, GFP-tag, thioredoxin, epitope tag of thioredoxin, Avi-tag, or another peptide tag. Preferably, the AT is selected from a polyHis-tag, ZZ tag, FLAG tag, HA tag, and GST tag; more preferably the AT is selected from a polyHis-tag and a ZZ-tag. In practice, in the first affinity chromatography step a resin that allows for a quick and highly efficient capture of target complexes is preferred. For this purpose, the inventors routinely use a $Ni^{2+}$ chelate resin along with a polyHis-tagged first subunit. The protease used for on-column cleavage must therefore not contain a polyHis-tag. In the second affinity purification step several well-established matrices can be used, amongst them the IgG-resin binding to ZZ-tag, or any antibody-based resin directed against peptide tags. Thus, in a specific embodiment, the first subunit comprises a polyHis-tag, and preferably the second subunit comprises a ZZ-tag. The "mixture" may be any suitable starting material for the purification method, such as an aqueous buffered or non-buffered solution comprising the stoichiometric protein complex. The "mixture" may be a lysate, a supernatant, a pre-purified lysate or a pre-purified supernatant, or mixtures thereof, e.g. a mixture of lysates, a mixture of supernatants, or a mixture of a lysate and a supernatant, and the like. Accordingly, the mixture may originate from a mixture of lysates and/or supernatants and/or a pre-purified solution, each comprising at least one of the subunits; or the mixture may originate from a single lysate or supernatant or pre-purified solution comprising all subunits of the protein complex. In a preferred embodiment, the mixture originates from a suitable eukaryotic expression host cell, preferably wherein said eukaryotic cell is a fungal cell, plant cell, mammalian cell, or insect cell; more preferably wherein said host cell is a fungal cell or a plant cell, even more preferably wherein the cell is a fungal cell, even more preferably the host cell is a yeast cell, still more preferably wherein the cell is of the genus *Saccharomyces*, most preferably wherein the host cell is a cell of *Saccharomyces cerevisiae*.

The term "impurities" may also encompass an undesired buffered solution or a saline, undesired proteins other than the subunits of the complex, cell debris, and possibly monomers of the respective subunits and/or degradation products of said complex. Accordingly, apart from removing such monomers and/or degradation products, the method of the invention may also be used for replacing the buffered solution or saline, or for removing an undesired compound within the buffered solution or saline.

In analogy to the purification of binary complexes using two orthogonal tags and proteases, a purification scheme employing three or more orthogonal tags and proteases can be used for a straightforward purification of stoichiometric triple or higher order complexes. In general, the method allows for the purification of complexes comprising each orthogonally tagged subunit at least once. More specifically, the method is ideally suited for the purification of stoichiometric complexes if each orthogonally tagged subunit is comprised in the complex exactly once. If the protein complex is composed of two subunits, it preferably has a stoichiometry of 1:1. Likewise, if the protein complex is composed of 3 different subunits, it preferably has a stoichiometry of 1:1:1. Dependent on the nature of the protein complex, each of the subunits may be comprised once, twice or more often in the protein complex. For example, if the protein complex is composed of 2 different subunits, it may have a stoichiometry of 1:1, 1:2, 2:1, 2:2, 1:3, 3:1, 2:3, 3:2, or 3:3, etc. As the method only allows selecting for the presence of orthogonally tagged subunits, purification of such complexes with defined stoichiometry is preferably performed using orthogonal tags on otherwise identical subunits.

In this context, the term "orthogonal" is intended to mean that the protease exhibits only cleavage activity against its corresponding substrate recognition sequence, but not on the other PRS or sequences in the subunits. The inventors have discovered and identified such orthogonal protease/PRS systems, which enable the above described method, and which are largely devoid of such drawbacks. They will therefore be of great practical use for labs routinely purifying recombinant proteins and protein complexes. Most importantly, the proposed purification schemes for single proteins and protein complexes are highly efficient and generally applicable. Due to the high efficiency of the provided proteases even at low temperatures and their tolerance towards various buffer conditions, the schemes can be adapted to the needs of the target proteins or complexes over a wide range of conditions.

Accordingly, one PRS may comprise, preferably consist of
(i) an amino acid sequence as shown in SEQ ID NO: 9 (bdSUMO); or
(ii) a PRS derivative of (i) with an amino acid sequence having at least 60% identity, preferably at least 65% identity, more preferably at least 70% identity, more preferably at least 75% identity, more preferably at least 80% identity, more preferably at least 85% identity, more preferably at least 90% identity, more preferably at least 95% identity, even more preferably at least 98% identity, and most preferably at least 99% identity over the full length of SEQ ID NO: 10 (bdSUMO),
wherein the protease shown in SEQ ID NO: 11 (bdSENP1$^{248\text{-}481}$) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to when using the parent PRS with the amino acid sequence of SEQ ID NO: 10, under identical conditions of 30 nM protease, 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT.

The AT of the subunit comprising said bdSUMO PRS is cleaved off using
(i) a protease comprising, preferably consisting of the amino acid sequence shown in amino acids 1-224 of SEQ ID NO: 11 (bdSENP1$^{248\text{-}481}$), or
(ii) a protease derivative of (i) having an amino acid sequence with at least 45% identity, preferably at least 50% identity, more preferably at least 55% identity, more preferably at least 60% identity, more preferably at least 65% identity, more preferably at least 70% identity, more preferably at least 75% identity, more preferably at least 80% identity, more preferably at least 85% identity, more preferably at least 90% identity, more preferably at least 95% identity, even more preferably at least 98% identity, and most preferably at least 99% over the full length of SEQ ID NO: 11, wherein said protease derivative is capable of cleaving the PRS according to ID NO: 10 (bdSUMO) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease as defined in (i), if tested using a native substrate protein shown in SEQ ID NO: 8 (His$_{14}$-bdSUMO-MBP) and 30 nM of said protease at standard conditions 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

However, most preferably said bdSUMO containing subunit is eluted from the column using the protease shown in in amino acids 1-224 of SEQ ID NO: 11 (bdSENP1$^{248-481}$).

In addition, or alternatively, one PRS comprises, preferably consists of
(i) an amino acid sequence as shown in SEQ ID NO: 12 (bdNEDD8); or
(ii) a PRS derivative of (i) with an amino acid sequence having at least 85% identity, more preferably at least 90% identity, more preferably at least 95% identity, even more preferably at least 98% identity, and most preferably at least 99% over the full length of SEQ ID NO: 12,
wherein the protease shown in SEQ ID NO: 13 (bdNEDP1) is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to when using the parent PRS with the amino acid sequence of SEQ ID NO: 12 under identical conditions of 300 nM protease, 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

The AT of the subunit comprising said bdNEDD8 PRS is cleaved off using
(i) a protease comprising, preferably consisting of the amino acid sequence shown in SEQ ID NO: 13 (bdNEDP1), or
(ii) a protease derivative of (i) having an amino acid sequence with at least 35% identity, more preferably at least 40% identity, more preferably at least 45% identity, more preferably at least 50% identity, more preferably at least 55% identity, more preferably at least 60% identity, more preferably at least 65% identity, more preferably at least 70% identity, more preferably at least 75% identity, more preferably at least 80% identity, more preferably at least 85% identity, more preferably at least 90% identity, more preferably at least 95% identity, even more preferably at least 98% identity, and most preferably at least 99% over the full length of SEQ ID NO: 13 (bdNEDP1),
wherein said protease derivative, cleaves the PRS according to SEQ ID NO: 12 (bdNEDD8) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease as defined in (i), if tested using a native substrate protein shown in SEQ ID NO: 7 (His$_{14}$-bdNEDD8-MBP) and 300 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

In a preferred embodiment, the subunit comprising said bdNEDD8 PRS is eluted from the column using the protease comprising, preferably consisting of the amino acid sequence shown in SEQ ID NO: 13 (bdNEDP1).

One can easily envision that other well-established proteases recognizing linear peptide motifs (e.g. TEV protease) constitute further groups of proteases with orthogonal specificity. Accordingly, one PRS may comprise, preferably consist of the TEV protease recognition site shown in SEQ ID NO: 14. The AT of the subunit comprising such an TEV-PRS is cleaved off using a TEV protease as shown in SEQ ID NO: 15 or a derivative thereof having an amino acid sequence with at least 80% identity, preferably at least 85% identity, more preferably with at least 90% identity, even more preferably with at least 95% identity, and most preferably with at least 98% identity over the full length of SEQ ID NO: 15 (TEV), wherein said protease derivative is capable of cleaving the TEV-PRS shown in SEQ ID NO: 14 with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to the protease as shown in SEQ ID NO: 15, if tested using a native substrate protein shown in SEQ ID NO: 6 (His$_{10}$-ZZ-TEV-MBP) and 10 µM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT. One example of such a derivative is the protease as shown in SEQ ID NO: 16.

In addition, or alternatively, one PRS comprises, preferably consists of
(i) an amino acid sequence as shown in SEQ ID NO: 17 (xlUb); or
(ii) a PRS derivative of (i) with an amino acid sequence having at least 80% identity, preferably at least 85% identity, more preferably with at least 90% identity, even more preferably with at least 95% identity, and most preferably with at least 98% identity over the full length of SEQ ID NO: 17,
wherein the protease shown in SEQ ID NO: 18 (xlUsp2), is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to when using the parent PRS with the amino acid sequence of SEQ ID NO: 17 under identical conditions of 1 µM protease, 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT; and The AT of the subunit comprising said xlUb-PRS is cleaved off using
(i) a protease comprising, preferably consisting of the amino acid sequence shown in SEQ ID NO: 18 (xlUsp2), or
(ii) a protease derivative of (i) having an amino acid sequence with at least 80% identity, preferably at least 85% identity, more preferably with at least 90% identity, even more preferably with at least 95% identity, and most preferably with at least 98% identity over the full length of SEQ ID NO: 18, wherein said protease derivative is capable of cleaving the PRS according to ID NO: 17 (xlUb) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to the parent protease as defined in (i), if tested using a native substrate protein shown in SEQ ID NO: 9 (His$_{14}$-xlUb-MBP) and 1 µM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

In addition, or alternatively, one PRS comprises, preferably consists of
(i) an amino acid sequence as shown in SEQ ID NO: 23 (SUMOstar); or
(ii) a PRS derivative of (i) with an amino acid sequence having at least 80% identity, preferably at least 85% identity, more preferably with at least 90% identity, even more preferably with at least 95% identity, and most preferably with at least 98% identity over the full length of SEQ ID NO: 23,
wherein the protease shown in SEQ ID NO: 24 (SUMOstar protease), is capable of cleaving said PRS derivative with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to when using the parent PRS with the amino acid sequence of SEQ ID NO: 23 under identical conditions of 30 nM protease, 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT; and The AT of the subunit comprising said SUMOstar-PRS is cleaved off using
(i) a protease comprising, preferably consisting of the amino acid sequence shown in SEQ ID NO: 24 (SUMOstar protease), or
(ii) a protease derivative of (i) having an amino acid sequence with at least 80% identity, preferably at least 85% identity, more preferably with at least 90% identity, even more preferably with at least 95% identity, and most preferably with at least 98% identity over the full length of SEQ ID NO: 24, wherein said protease derivative is capable of cleaving the PRS according to ID NO: 23 (SUMOstar) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% activity as compared to the parent protease as defined in (i), if tested using a native substrate protein shown in SEQ ID NO: 22 (His$_{14}$-SUMOstar-MBP) and 30 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

Particular preferred combinations of orthogonal protease sets are in case of fungal cell expression systems
(a) wherein one subunit comprises the PRS xlLC3B or a PRS derivative thereof, and wherein the elution is carried out using an xlAtg4B protease or derivative thereof as disclosed herein; and wherein the other subunit comprises the PRS bdNEDD8 or a PRS derivative thereof and wherein the elution is carried out using the bdNEDP1 or derivative thereof, as defined above;
(b) wherein one subunit comprises the PRS xlLC3B or a PRS derivative thereof, and wherein the elution is carried out using an xlAtg4B protease or derivative thereof as disclosed herein; and wherein the other subunit comprises the PRS SUMOstar or a PRS derivative thereof and wherein the elution is carried out using the SUMOstar protease or a derivative thereof, as defined above; or
(c) wherein one subunit comprises the PRS xlLC3B or a PRS derivative thereof, and wherein the elution is carried out using an xlAtg4B protease or derivative thereof as disclosed herein; and wherein a second subunit comprises the PRS bdNEDD8 or a PRS derivative thereof and wherein the elution is carried out using the bdNEDP1 or derivative thereof, as defined above; and wherein a third subunit comprises the PRS SUMOstar or a PRS derivative thereof and wherein the elution is carried out using the SUMOstar protease or a derivative thereof, as defined above.

Particular preferred combinations of orthogonal protease sets are in case of plant cell expression systems
(a) wherein one subunit comprises the PRS xlLC3B or a PRS derivative thereof, and wherein the elution is carried out using an xlAtg4B protease or derivative thereof as disclosed herein; and wherein the other subunit comprises the PRS SUMOstar or a PRS derivative thereof and wherein the elution is carried out using the SUMOstar protease or a derivative thereof, as defined above, or
(b) wherein one subunit comprises the PRS xlGATE16 or a PRS derivative thereof, and wherein the elution is carried out using an xlAtg4B protease or derivative thereof as disclosed herein; and wherein the other subunit comprises the PRS SUMOstar or a PRS derivative thereof and wherein the elution is carried out using the SUMOstar protease or a derivative thereof, as defined above.

In case of plant cell expression systems, (a) is preferred.

However, the protease sets of the present disclosure may also be useful in other eukaryotic expression systems, such as host cells of the kingdom Excavate (such as Leishmania cells) as well as of the kingdom Amoebozoa, Chromalveolata, or Rhizaria. In this case, the PRS of one subunit may be selected from the PRS xlLC3B or a PRS derivative thereof and the PRS xlGATE16 or a PRS derivative thereof, preferably the PRS xlLC3B or a PRS derivative thereof, and wherein the elution is carried out using an xlAtg4B protease or derivative thereof as disclosed herein; and a second subunit comprises the PRS SUMOstar or a PRS derivative thereof and wherein the elution is carried out using the SUMOstar protease or a derivative thereof; or said second subunit comprises the PRS bdNEDD8 or a PRS derivative thereof and wherein the elution is carried out using the bdNEDP1 or derivative thereof, as defined above; or wherein a second subunit comprises the PRS bdNEDD8 or a PRS derivative thereof and wherein the elution is carried out using the bdNEDP1 or derivative thereof, as defined above; and wherein a third subunit comprises the PRS SUMOstar or a PRS derivative thereof and wherein the elution is carried out using the SUMOstar protease or a derivative thereof, as defined above.

Further guidance for the method of the disclosure is provided in WO 2015/049230 and Frey and GOrlich (2014) J Chromatogr A 1337, 106-115.

Also provided is a kit of parts, comprising (i) the xlAtg4B protease fragment or derivative as disclosed herein, and (ii) an expression vector or a host cell of the present disclosure.

Finally, the present disclosure provides a kit of parts, comprising
(i) the xlAtg4B protease fragment or derivative as disclosed herein, and at least one protease selected from the group of proteases consisting of
(ii) a protease having an amino acid sequence with at least 45% identity, preferably at least 50% identity, more preferably at least 55% identity, more preferably at least 60% identity, more preferably at least 65% identity, more preferably at least 70% identity, more preferably at least 75% identity, more preferably at least 80% identity, more preferably at least 85% identity, more preferably at least 90% identity, more preferably at least 95% identity, even more preferably at least 98% identity, and most preferably at least 99% over the full length of SEQ ID NO: 11 (bdSENP1),
wherein said protease is capable of cleaving the PRS according to ID NO: 10 (bdSUMO) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease of SEQ ID NO: 10 (bdSENP1), if tested using a native substrate protein shown in SEQ ID NO: 8 ($His_{14}$-bdSUMO-MBP) and 30 nM of said protease at standard conditions of 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; preferably wherein the protease comprises the amino acid sequence shown as amino acids 1-224 in SEQ ID NO: 11 ($bdSENP1^{248-481}$); and more preferably wherein the protease consists of the amino acid sequence shown as amino acids 1-224 in SEQ ID NO: 11 ($bdSENP1_{248-481}$);
(iii) a protease having an amino acid sequence with at least 35% identity, preferably at least 40% identity, more preferably at least 45% identity, more preferably at least 50% identity, more preferably at least 55% identity, more preferably at least 60% identity, more preferably at least 65% identity, more preferably at least 70% identity, more preferably at least 75% identity, more preferably at least 80% identity, more preferably at least 85% identity, more preferably at least 90% identity, more preferably at least 95% identity, even more preferably at least 98% identity, and most preferably at least 99% over the full length of SEQ ID NO: 13 (bdNEDP1),
wherein said protease cleaves the PRS according to SEQ ID NO: 12 (bdNEDD8) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease of SEQ ID NO: 13 (bdNEDP1), if tested using a native substrate protein shown in SEQ ID NO: 7 ($His_{14}$-bdNEDD8-MBP) and 300 nM of said protease at standard conditions of 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; preferably wherein the protease comprises the amino acid sequence as shown in SEQ ID NO: 13 (bdNEDP1); and more preferably wherein the protease consists of the amino acid sequence as shown in SEQ ID NO: 13 (bdNEDP1);
(iv) a protease having an amino acid sequence with at least 80% identity, preferably at least 85% identity, more preferably at least 90% identity, more preferably at least 95% identity, even more preferably at least 98% identity, and most preferably at least 99% over the full length of SEQ ID NO: 15 or 16, wherein said protease is capable of cleaving the PRS according to SEQ ID NO: 14 (TEV) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease of SEQ ID NO: 15 or 16, if tested using a native substrate protein shown in SEQ ID NO: 6 ($His_{10}$-ZZ-TEV-MBP) and 10 µM of said protease at standard conditions of 1 hour incubation at 0° C., 100 µM initial concentration of substrate protein in a buffer consisting of 250 mM NaCl, 40 mM Tris/HCl pH 7.5, 2 mM $MgCl_2$, 250 mM sucrose, 2 mM DTT; preferably wherein the protease comprises the amino acid sequence as shown in SEQ ID NO: 15 or 16, and more preferably wherein the protease consists of the amino acid sequence as shown in SEQ ID NO: 15 or 16;
(v) a protease having an amino acid sequence with at least 80% identity, preferably at least 85% identity, more preferably at least 90% identity, more preferably at least 95% identity, even more preferably at least 98% identity, and most preferably at least 99% over the full length of SEQ ID NO: 18 (xlUsp2),
wherein said protease is capable of cleaving the PRS according to ID NO: 17 (xlUb) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease of SEQ ID NO: 18 (xlUsp2), if tested using a native substrate protein shown in SEQ ID NO: 9 (His$_{14}$-xlUb-MBP) and 1 µM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT; preferably wherein the protease comprises the amino acid sequence as shown in SEQ ID NO: 18 (xlUsp2); and more preferably wherein the protease consists of the amino acid sequence as shown in SEQ ID NO: 18 (xlUsp2);

(vi) a protease having an amino acid sequence with at least 80% identity, preferably at least 85% identity, more preferably at least 90% identity, more preferably at least 95% identity, even more preferably at least 98% identity, and most preferably at least 99% over the full length of SEQ ID NO: 24 (SUMOstar protease), wherein said protease is capable of cleaving the PRS according to ID NO: 23 (SUMOstar) with at least 20% activity, preferably at least 30% activity, more preferably at least 40% activity, even more preferably at least 50% activity, still more preferably at least 60% activity, still even more preferably at least 70% activity, most preferably at least 80% activity, even most preferably at least 90% activity such as more than 100% as compared to the parent protease as defined in (i), if tested using a native substrate protein shown in SEQ ID NO: 22 (His$_{14}$-SUMOstar-MBP) and 30 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT; preferably wherein the protease comprises the amino acid sequence as shown in SEQ ID NO: 24 (SUMOstar protease); and more preferably wherein the protease consists of the amino acid sequence as shown in SEQ ID NO: 24 (SUMOstar protease).

Particularly preferred combination of proteases are (i) and (ii); (i) and (iii); and (i) and (iv). At least one protease may further comprises an affinity tag, preferably a poly-His tag or a ZZ tag.

The orthogonal proteases disclosed herein as well as the kit comprising these orthogonal proteases can be advantageously used in a method of purifying stoichiometric protein complexes comprising at least two subunits. In a preferred embodiment the method is further defined as described above, e.g., wherein the mixture originates from a suitable eukaryotic expression host cell, in particular wherein said eukaryotic cell is a fungal cell or a plant cell. In a more preferred embodiment, the host cell is a fungal cell, even more preferably the host cell is a yeast cell, still more preferably wherein the cell is of the genus *Saccharomyces*, and most preferably wherein the host cell is a cell of *Saccharomyces cerevisiae*. In another more preferred embodiment, the host cell is a plant cell, preferably wherein said plant cell is a cell of the order Poales, more preferably wherein said cell is of the family Poaceae, even more preferably wherein said cell is of the subfamily Pooideae, still more preferably wherein said cell is of the tribe Triticeae, and most preferably, wherein said cell is of the genus *Triticum*.

In particular, the orthogonal proteases disclosed herein as well as the kit comprising these orthogonal proteases can be advantageously used for on-column cleavage in an affinity chromatography.

Other possible applications of xlATG4B may include regulated degradation (TIPI system (Taxis, C. and Knop, M. (2012) *Methods Mol Biol* 832, 611-626; Taxis, C., Stier, G., Spadaccini, R. and Knop, M. (2009) *Mol Syst Biol* 5, 267)) or targeted localization (Urabe, M., Kume, A., Takahashi, T., Serizawa, N., Tobita, K. and Ozawa, K. (1999) *Biochem Biophys Res Commun* 266, 92-96). These techniques have so far mostly been performed using TEV protease. For the TIPI system, however, it has been shown that the poor proteolytic activity and pronounced P$_1$' sensitivity of TEV protease is limiting for the proteolytic activation of the degradation signal (Renicke, C., Spadaccini, R. and Taxis, C. (2013) *PLoS One* 8, e67915). Here, xlAtg4B with its high activity and pronounced P$_1$' promiscuity could potentially have clear advantages over TEV protease.

In the following, the present invention is illustrated by figures and examples, which are not intended to limit the scope of the present invention. All references cited herein are explicitly incorporated by reference.

Figure 11:
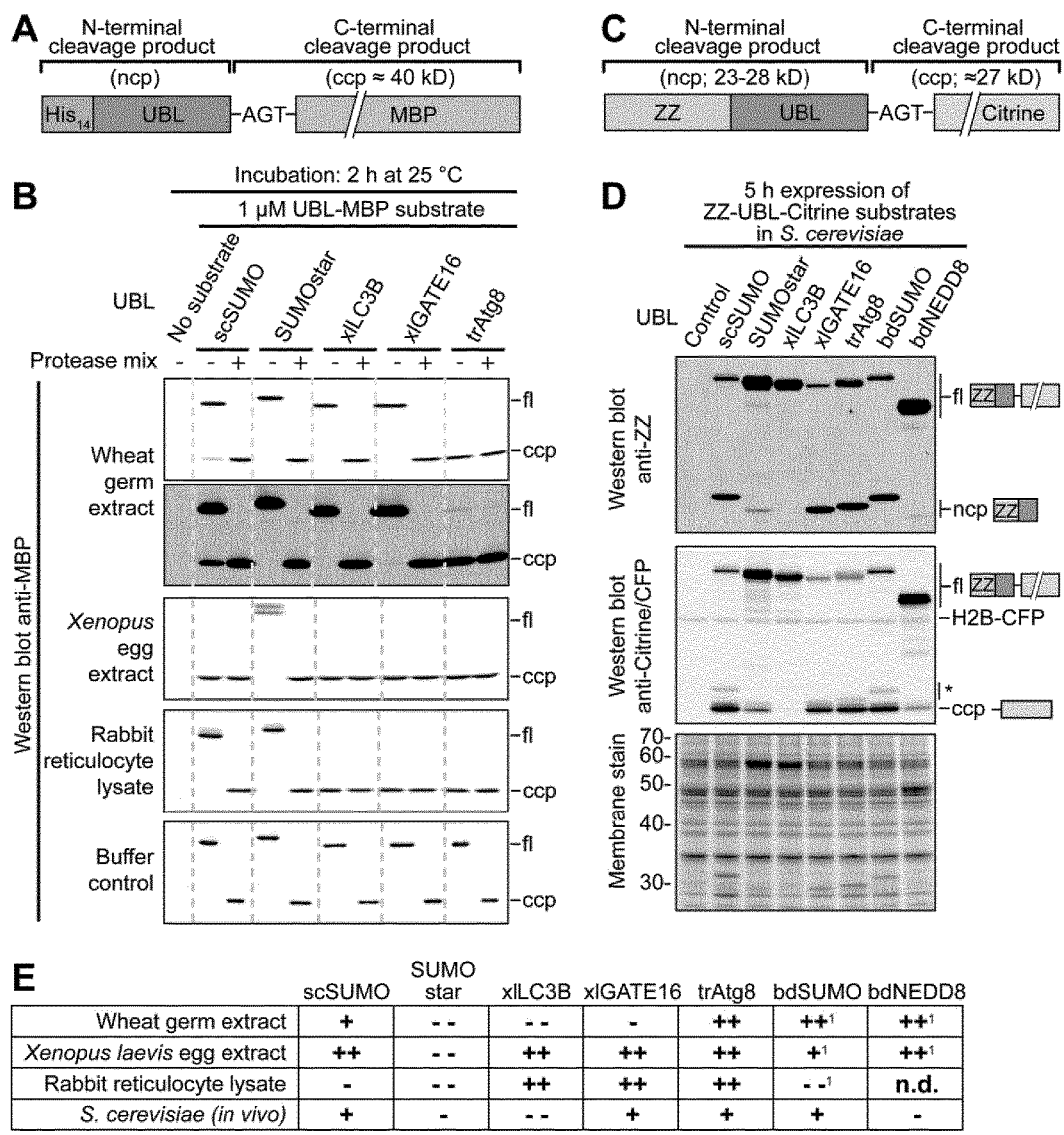

FIG. 11: Stability of UBL fusions in eukaryotic lysates and in *S. cerevisiae*. A, Schematic representation of substrates used for (B). B, Stability of protease substrates in cell extracts. C, Schematic representation of substrates used expression in *S. cerevisiae* (D) harboring an N-terminal ZZ-tag, a ubiquitin-like protein (UBL) and a C-terminal Citrine. D, In-vivo stability of protease substrates in *S. cerevisiae*. Indicated protease substrates were over-expressed in a *S. cerevisiae* strain constitutively expressing H2B-CFP as described in the section "Methods" in the Examples section below. Total cell lysates were analyzed by Western blot with an antibody recognizing the ZZ-tag (upper panel) or both Citrine and CFP (middle panel), respectively. Equal loading was confirmed by staining the membrane after blotting (lower panel). Bands marked with an asterisk (*) originate from ZZ-tagged proteins cross-reacting with the anti-Citrine/CFP antibody. E, Cleavage of UBL substrates in extracts and in *S. cerevisiae*. ++, highly efficient cleavage; +, cleavage; −, traces cleaved; −−, no cleavage; n.d.: not determined; [1] data not shown.

Figure 12:
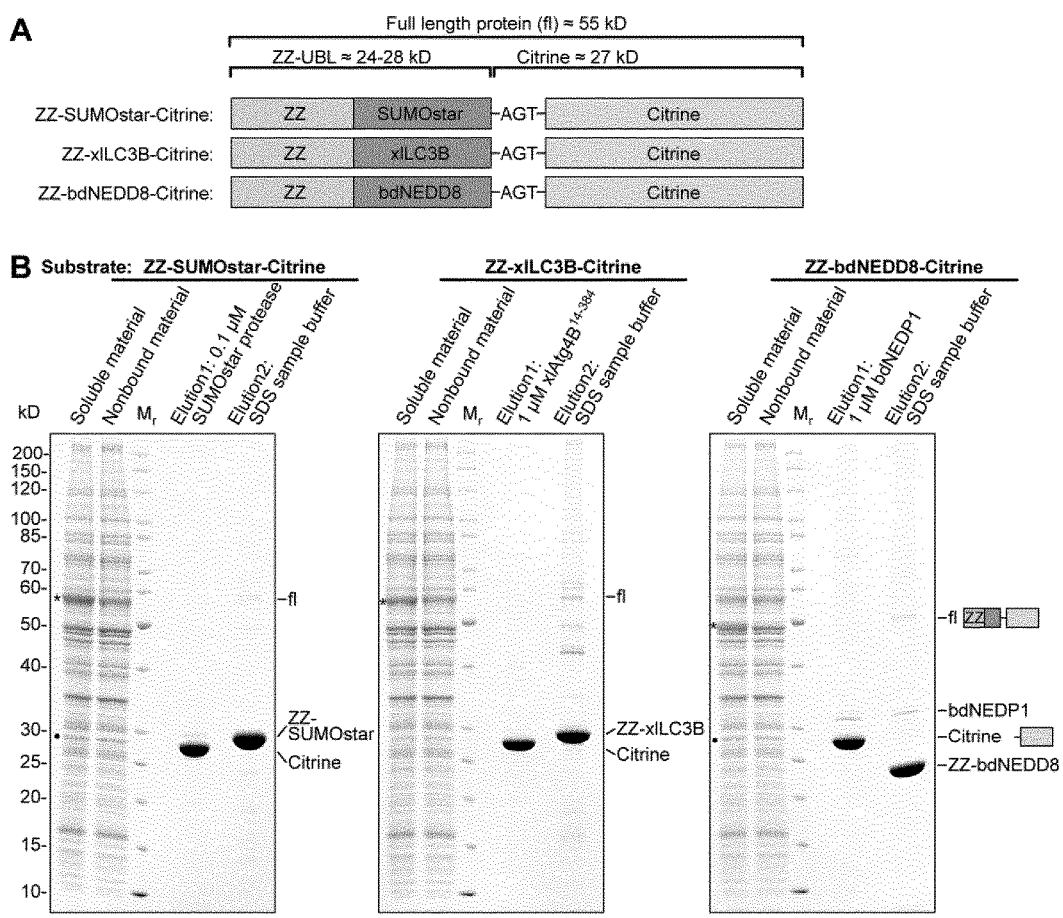

FIG. 12: One-step protein purification from *S. cerevisiae*. ZZ-UBL-Citrine fusions sketched in (A) were over-expressed in *S. cerevisiae* as described in the section "Methods" in the Examples section below. Cells were lysed and the soluble material was incubated with an anti-ZZ affinity resin. After washing off non-bound material, highly pure Citrine was eluted by treatment with 0.1 µM SUMOstar protease (B), 1 µM xlAtg4B$^{14-384}$ (C) or 1 µM bdNEDD8 (D) for 1 h at 4° C. Material remaining on the resin was analyzed after elution with SDS sample buffer. The asterisk (*) denotes the full-length xlLC3B fusion protein. The filled circle (●) marks band partially corresponding to low levels of free Citrine originating from in-vivo cleavage of the respective SUMOstar and bdNEDD8 fusion proteins.

DESCRIPTION OF THE SEQUENCES (*Xenopus laevis* Atg4B (xlAtg4B))
SEQ ID NO: 1
MDAATLTYDTLRFADTPDFPETAEPVWVLGRKYSALTEKEQLLNDITSRL
WFTYRRNFQAIGGTGPTSDTGWGCMLRCGQMIFAQALICRHVGRDWRWDK
QKPKGEYLNILTAFLDKKDSYYSIHQIAQMGVGEGKYIGQWYGPNTVAQV
LRKLAVFDQWSSIAVHIAMDNTVVVDEIRRLCRAGSGESSDAGALSNGYT
GDSDPSCAQWKPLVLLIPLRLGLSEINEAYIETLKHCFMVPQSLGVIGGR
PNSAHYFIGYVGDELIYLDPHTTQLSVEPSDCSFIEDESFHCQHPPCRMH
VSEIDPSIAVGFFCSSQEDFEDWCQHIKKLSLSGGALPMFEVVDQLPLHL
SNPDVLNLTPDSSDADRLDRFFDSEDEEFEILSL (*Xenopus laevis* LC3B (xlLC3B))
SEQ ID NO: 2
MPSEKTFKQRRSLEQRVEDVRLIREQHPTKIPVIIERYKGEKQLPVLDKT
KFLVPDHVNMSELIKIIRRRLQLNSNQAFFLLVNGHSMVSVSTPISEVYE
REKDEDGFLYMVYASQETFG (His$_{14}$-xlLC3B-MBP)
SEQ ID NO: 3
MSKHHHHSGHHHTGHHHHSGSHHHTGGSSGSESSEKTFKQRRSLEQRVED
VRLIREQHPTKIPVIIERYKGEKQLPVLDKTKFLVPDHVNMSELIKIIRR
RLQLNSNQAFFLLVNGHSMVSVSTPISEVYEREKDEDGFLYMVYASQETF
GAGTKTEEGKLVIWINGDKGYNGLAEVGKKFEKDTGIKVTVEHPDKLEEK
FPQVAATGDGPDIIFWAHDRFGGYAQSGLLAEITPDKAFQDKLYPFTWDA
VRYNGKLIAYPIAVEALSLIYNKDLLPNPPKTWEEIPALDKELKAKGKSA
LMFNLQEPYFTWPLIAADGGYAFKYENGKYDIKDVGVDNAGAKAGLTFLV
DLIKNKHMNADTDYSIAEAAFNKGETAMTINGPWAWSNIDTSKVNYGVTV
LPTFKGQPSKPFVGVLSAGINAASPNKELAKEFLENYLLTDEGLEAVNKD
KPLGAVALKSYEEELAKDPRIAATMENAQKGEIMPNIPQMSAFWYAVRTA
VINAASGRQTVDEALKDAQTNGTGC (*Xenopus laevis* GATE16 (xlGATE16))
SEQ ID NO: 4
MKWMFKEDHSLEHRCVESAKIRAKYPDRVPVIVEKVSGSQIVDIDKRKYL
VPSDITVAQFMWIIRKRIQLPSEKAIFLFVDKTVPQSSLTMGQLYEKEKD
EDGFLYVAYSGENTFG (His$_{14}$-xlGATE16-MBP)
SEQ ID NO: 5
MSKHHHHSGHHHTGHHHHSGSHHHTGGSSGSESSMKWMFKEDHSLEHRCV
ESAKIRAKYPDRVPVIVEKVSGSQIVDIDKRKYLVPSDITVAQFMWIIRK
RIQLPSEKAIFLFVDKTVPQSSLTMGQLYEKEKDEDGFLYVAYSGENTFG
AGTKTEEGKLVIWINGDKGYNGLAEVGKKFEKDTGIKVIVEHPDKLEEKF
PQVAATGDGPDIIFWAHDRFGGYAQSGLLAEITPDKAFQDKLYPFTWDAV
RYNGKLIAYPIAVEALSLIYNKDLLPNPPKTWEEIPALDKELKAKGKSAL
MFNLQEPYFTWPLIAADGGYAFKYENGKYDIKDVGVDNAGAKAGLTFLVD
LIKNKHMNADTDYSIAEAAFNKGETAMTINGPWAWSNIDTSKVNYGVTVL
PTFKGQPSKPFVGVLSAGINAASPNKELAKEFLENYLLTDEGLEAVNKDK
PLGAVALKSYEEELAKDPRIAATMENAQKGEIMPNIPQMSAFWYAVRTAV
INAASGRQTVDEALKDAQTNGTGC (His$_{10}$-ZZ-TEV-MBP)
SEQ ID NO: 6
MHHHHHHHHHHGSNKFNKEQQNAFYEILHLPNLNEEQRNAFIQSLKDDPS
QSANLLAEAKKLNDAQAPKVAMNKFNKEQQNAFYEILHLPNLNEEQRNAF
IQSLKDDPSQSANLLAEAKKLNDAQAPKVAMSGENLYFQGTKTEEGKLVI
WINGDKGYNGLAEVGKKFEKDTGIKVTVEHPDKLEEKFPQVAATGDGPDI
IFWAHDRFGGYAQSGLLAEITPDKAFQDKLYPFTWDAVRYNGKLIAYPIA
VEALSLIYNKDLLPNPPKTWEEIPALDKELKAKGKSALMFNLQEPYFTWP
LIAADGGYAFKYENGKYDIKDVGVDNAGAKAGLTFLVDLIKNKHMNADTD
YSIAEAAFNKGETAMTINGPWAWSNIDTSKVNYGVTVLPTFKGQPSKPFV
GVLSAGINAASPNKELAKEFLENYLLTDEGLEAVNKDKPLGAVALKSYEE
ELAKDPRIAATMENAQKGEIMPNIPQMSAFWYAVRTAVINAASGRQTVDE
ALKDAQTNGTGC (His$_{14}$-bdNEDD8-MBP)
SEQ ID NO: 7
MSKHHHHSGHHHTGHHHHSGSHHHSGTMIKVKTLTGKEIEIDIEPTDTID
RIKERVEEKEGIPPVQQRLIYAGKQLADDKTAKDYNIEGGSVLHLVLALR
GGAGTKTEEGKLVIWINGDKGYNGLAEVGKKFEKDTGIKVTVEHPDKLEE
KFPQVAATGDGPDIIFWAHDRFGGYAQSGLLAEITPDKAFQDKLYPFTWD

```
AVRYNGKLIAYPIAVEALSLIYNKDLLPNPPKTVVEEIPALDKELKAKGK
SALMFNLQEPYFTWPLIAADGGYAFKYENGKYDIKDVGVDNAGAKAGLTF
LVDLIKNKHMNADTDYSIAEAAFNKGETAMTINGPWAWSNIDTSKVNYGV
TVLPTFKGQPSKPFVGVLSAGINAASPNKELAKEFLENYLLTDEGLEAVN
KDKPLGAVALKSYEEELAKDPRIAATMENAQKGEIMPNIPQMSAFWYAVR
TAVINAASGRQTVDEALKDAQTNGTGC
```

(His₁₄-bdSUMO-MBP)
SEQ ID NO: 8
```
MSKHHHHSGHHHTGHHHHSGSHHHSGSAAGGEEDKKPAGGEGGGAHINLK
VKGQDGNEVFFRIKRSTQLKKLMNAYCDRQSVDMTAIAFLFDGRRLRAEQ
TPDELEMEDGDEIDAMLHQTGGAGTKTEEGKLVIWINGDKGYNGLAEVGK
KFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNP
PKTWEEIPALDKELKAKGKSALMFNLQEPYFTWPLIAADGGYAFKYENGK
YDIKDVGVDNAGAKAGLTFLVDLIKNKHMNADTDYSIAEAAFNKGETAMT
INGPWAWSNIDTSKVNYGVTVLPTFKGQPSKPFVGVLSAGINAASPNKEL
AKEFLENYLLTDEGLEAVNKDKPLGAVALKSYEEELAKDPRIAATMENAQ
KGEIMPNIPQMSAFWYAVRTAVINAASGRQTVDEALKDAQTNGTGC
```

(His₁₄-xlUb-MBP)
SEQ ID NO: 9
```
MSKHHHHSGHHHTGHHHHSGSHHHTGSSSGSESSMQIFVKTLTGKTITLE
VEPSDTIENVKAKIQDKEGIPPDQQRLIFAGKQLEDGRTLSDYNIQKEST
LHLVLRLRGGAGTKTEEGKLVIWINGDKGYNGLAEVGKKFEKDTGIKVTE
HPDKLEEKFPQVAATGDGPDIIFWAHDRFGGYAQSGLLAEITPDKAFQDK
LYPFTWDAVRYNGKLIAYPIAVEALSLIYNKDLLPNPPKTWEEIPALDKE
LKAKGKSALMFNLQEPYFTWPLIAADGGYAFKYENGKYDIKDVGVDNAGA
KAGLTFLVDLIKNKHMNADTDYSIAEAAFNKGETAMTINGPWAWSNIDTS
KVNYGVTVLPTFKGQPSKPFVGVLSAGINAASPNKELAKEFLENYLLTDE
GLEAVNKDKPLGAVALKSYEEELAKDPRIAATMENAQKGEIMPNIPQMSA
FWYAVRTAVINAASGRQTVDEALKDAQTNGTGC
```

(bdSUMO amino acids 21-97)
SEQ ID NO: 10
```
HINLKVKGQDGNEVFFRIKRSTQLKKLMNAYCDRQSVDMTAIAFLFDGRR
LRAEQTPDELEMEDGDEIDAMLHQTGG
```

(bdSENP1 amino acids 248-481)
SEQ ID NO: 11
```
PFVPLTDEDEDNVRHALGGRKRSETLSVHEASNIVITREILQCLNDKEWL
NDEVINLYLELLKERELREPNKFLKCHFFNTFFYKKLINGGYDYKSVRRW
TTKRKLGYNLIDCDKIFVPIHKDVHWCLAVINIKEKKFQYLDSLGYMDMK
ALRILAKYLVDEVKDKSGKQIDVHAWKQEGVQNLPLQENGWDCGMFMLKY
IDFYSRDMELVFGQKHMSYFRRRTAKEILDLKAG
```

(bdNEDD8; Brachypodium distachyon NEDD8)
SEQ ID NO: 12
```
MIKVKTLTGKEIEIDIEPTDTIDRIKERVEEKEGIPPVQQRLIYAGKQLA
DDKTAKDYNIEGGSVLHLVLALRGG
```

(bdNEDP1; Brachypodium distachyon NEDP1)
SEQ ID NO: 13
```
MDERVLSYGDVVLLRSDLAILRGPHFLNDRIIAFYLAHLSASFHGDGDLL
LLPPSIPYLLSNLPDPESVAEPLCLASRRLVLLPVNDNPDASVANGGSHW
TLLVLDAATTDPQAPRFVHHDSLRGSANAAAARRLARALTAGGAPLRFVE
APTPTQRNGHDCGVYVLAVARAICGWWRSSRRRENQQGGGGDWFATMMEE
VDAESVGAMRAELLQLIHRLIQDKEQEEEKKSKAGVEDTCGQ
```

Figure 10:
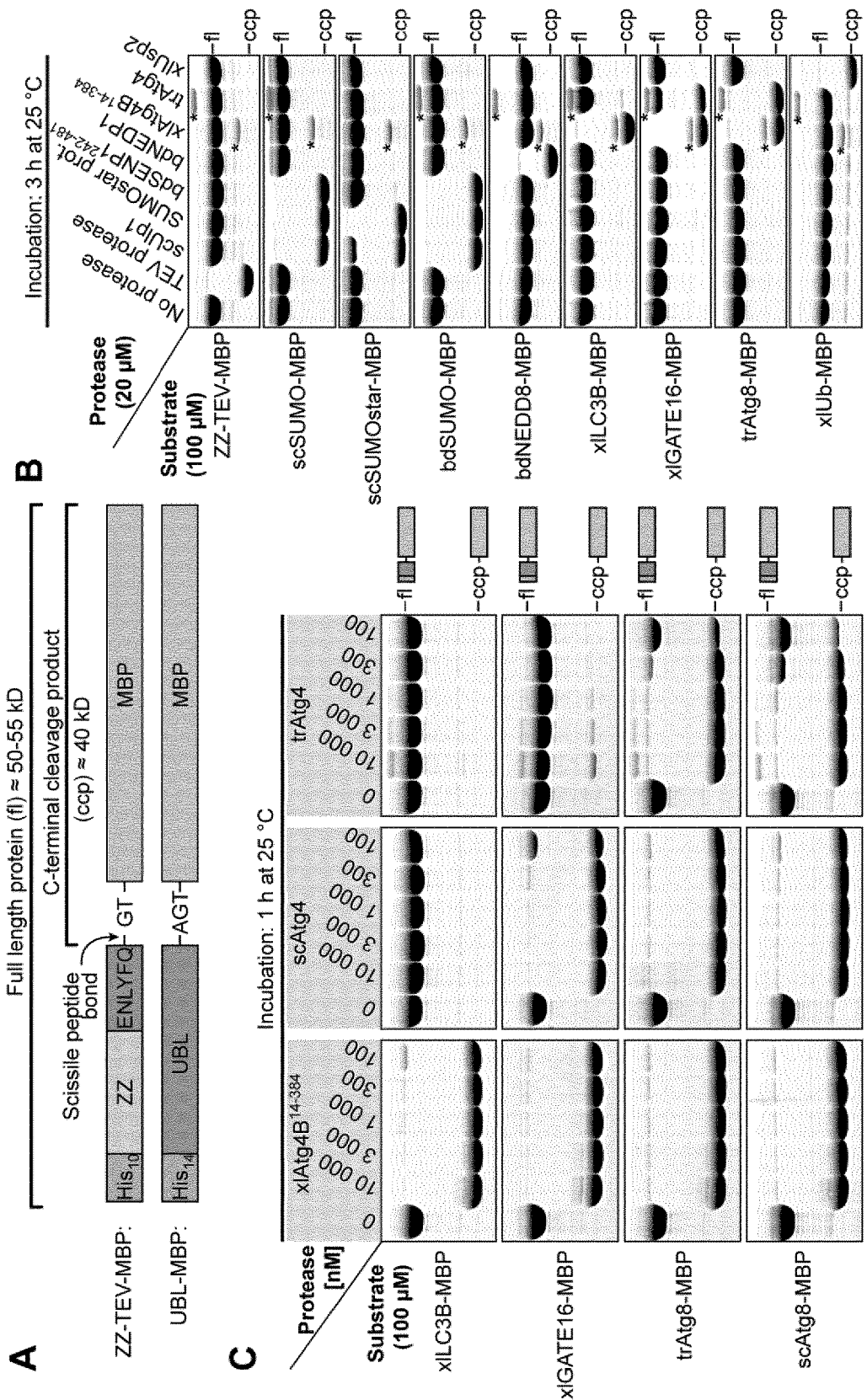
FIG. 10: In-vitro cross-reactivity with other tag cleaving proteases. A, Schematic representation of substrates used for (B) and (C). The TEV protease substrate contains an N-terminal His$_{10}$-ZZ tag preceding the TEV protease recognition site. All other substrates follow the scheme described in FIG. 4A, the protease recognition site, however, is replaced by the respective ubiquitin-like protein (UBL). B, Cross-reactivity between recombinant tag-cleaving proteases. bd, *Brachypodium distachyon*; tr, *Triticum aestivum* (summer wheat). 100 μM of indicated substrates were incubated with indicated proteases for 3 h at 25° C. in LS-S buffer. Bands marked with an asterisk (*) originate from the respective protease. C, Detailed titration analysis of cross-reactivity between *Xenopus laevis* (xl), *S. cerevisiae* (sc) and wheat (tr) Atg4 homologs. 100 µM of indicated substrates were incubated with various concentrations of indicated proteases for 1 h at 25° C. in LS-S buffer.

(TEV protease recognition site-spacer fusion (the spacer being underlined); cf. FIG. 10A)
SEQ ID NO: 14
ENLYFQG<u>T</u>

(TEV protease; Tobacco etch virus NIa protease)
SEQ ID NO: 15
```
GESLFKGPRDYNPISSTICHLTNESDGHTTSLYGIGFGPFIITNKHLFRR
NNGTLLVQSLHGVFKVKNTTTLQQHLIDGRDMIIIRMPKDFPPFPQKLKF
REPQREERICLVTINFQTKSMSSMVSDTSCTFPSSDGIFWKHWIQTKDGQ
CGSPLVSTRDGFIVGIHSASNFTNTNNYFTSVPKNFMELLTNQEAQQWVS
GWRLNADSVLWGGHKVFMSKPEEPFQPVKEATQLMNELVYSQ
```

(TEV(SH)ΔC6)
SEQ ID NO: 16
```
ESLFKGPRDYNPISSSICHLTNESDGHTTSLYGIGFGPFIITNKHLFRRN
NGTLLVQSLHGVFKVKDTTTLQQHLVDGRDMIIIRMPKDFPPFPQKLKFR
EPQREERICLVTTNFQTKSMSSMVSDTSCTFPSSDGIFWKHWIQTKDGQC
GSPLVSTRDGFIVGIHSASNFTNTNNYFTSVPKNFMELLTNQEAQQWVSG
WRLNADSVLWGGHKVFMNKPEEPFQPVKEATQLMN
```

(xlUb; Xenopus laevis ubiquitin)
SEQ ID NO: 17
```
MQIFVKILTGKTITLEVEPSDTIENVKAKIQDKEGIPPDQQRLIFAGKQL
EDGRTLSDYNIQKESTLHLVLRLRGG
```

(xlUsp2; Xenopus laevis ubiquitin-specific processing protease 2)
SEQ ID NO: 18
```
MRSHTLRIHGMGAGREHQIPGTVILSSIMDFILHRAKSSKHVQGLVGLRN
LGNTCFMNSILQCLSNTKDLRDYCQQNSYRRDLSSKKCNTAIMEEFARLL
QAIWTSSANEVVSPSEFKTQIQRYAPRFMGYNQQDAQEFLRFLLDGLHNE
VNRVTVKPRPSSQDLDHMPDSEKGKKMWKRYLEREDSRIVELFVGQLKSS
LTCTDCGYCSTVFDPFWDLSLPIAKKSASEVSLVDCMRLFTKEDVLDGDE
KPTCCRCKARRRCTKKFTIQRFPKILVLHLKRFSEGRIRSGKLSTFVNFP
LKDLDLREFSSESNPHATYNLYAVSNHSGTTMGGHYTAYCKNPSNGEWYT
FNDSRVTAMSSSQVKSSDAYVLFYELSGPSSRM
```

(Homo sapiens Atg4B (hsAtg4B))
SEQ ID NO: 19
```
MDAATLTYDTLRFAEFEDFPETSEPVWILGRKYSIFTEKDEILSDVASRL
WFTYRKNFPAIGGTGPTSDTGWGCMLRCGQMIFAQALVCRHLGRDWRWTQ
RKRQPDSYFSVLNAFIDRKDSYYSIHQIAQMGVGEGKSIGQWYGPNTVAQ
VLKKLAVFDTWSSLAVHIAMDNTVVMEEIRRLCRTSVPCAGATAFPADSD
RHCNGFPAGAEVTNRPSPWRPLVLLIPLRLGLTDINEAYVETLKHCFMMP
QSLGVIGGKPNSAHYFIGYVGEELIYLDPHTTQPAVEPTDGCFIPDESFH
```

-continued

CQHPPCRMSIAELDPSIAVGFFCKTEDDFNDWCQQVKKLSLLGGALPMFE

LVELQPSHLACPDVLNLSLDSSDVERLERFFDSEDEDFEILSL (Homo sapiens LC3B (hsLC3B))
SEQ ID NO: 20
MPSEKTFKQRRSFEQRVEDVRLIREQHPTKIPVIIERYKGEKQLPVLDKT

KFLVPDHVNMSELIKIIRRRLQLNANQAFFLLVNGHSMVSVSTPISEVYE

SERDEDGFLYMVYASQETFG (Homo sapiens GATE16 (hsGATE16))
SEQ ID NO: 21
MKWMFKEDHSLEHRCVESAKIRAKYPDRVPVIVEKVSGSQIVDIDKRKYL

VPSDITVAQFMWIIRKRIQLPSEKAIFLFVDKTVPQSSLTMGQLYEKEKD

EDGFLYVAYSGENTFG (His$_{14}$-SUMOstar-MBP)
SEQ ID NO: 22
MSKHHHHSGHHHTGHHHHSGSHHHTGSDSEVNQEAKPEVKPEVKPETHIN

LKVSDGSSEIFFKIKKTTPLRRLMEAFAKRQGKEMDSLTFLYDGIEIQAD

QTPEDLDMEDNDIIEAHREQIGGAGTKTEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTINDAVRYNGKLIAYPIAVEALSLIYNKDLLP

NPPKTWEEIPALDKELKAKGKSALMENLQEPYFTWPLIAADGGYAFKYEN

GKYDIKDVGVDNAGAKAGLTFLVDLIKNKHMNADTDYSIAEAAFNKGETA

MTINGPWAWSNIDTSKVNYGVTVLPTFKGQPSKPFVGVLSAGINAASPNK

ELAKEFLENYLLTDEGLEAVNKDKPLGAVALKSYEEELAKDPRIAATMEN

AQKGEIMPNIPQMSAFWYAVRTAVINAASGRQTVDEALKDAQTNGTGC (SUMOstar)
SEQ ID NO: 23
MSDSEVNQEAKPEVKPEVKPETHINLKVSDGSSEIFFKIKKTTPLRRLME

AFAKRQGKEMDSLTFLYDGIEIQADQTPEDLDMEDNDIIEAHREQIGG (SUMOstar protease)
SEQ ID NO: 24
LVPELNEKDDDQVQKALASRENTQLMNRDNIEITVRDFKTLAPRRWLNDT

IIEFFMKYIEKSTPNTVAFNSFFYTNLSERGYQGVRRWMKRKKTQIDKLD

KIFTPINLNQSHWALGIIDLKKKTIGYVDSLSNGPNAMSFAILTDLQKYV

MEESKHTIGEDFDLIHLDCPQQPNGYDCGIYVCMNTLYGSADAPLDFDYK

DAIRMRRFIAHLILTDALK (His$_{14}$-IF2d1-xlLC3B-MBP)
SEQ ID NO: 25
MSKHHHHSGHHHTGHHHHSGSHHHTGGSSGTDVTIKTLAAERQTSVERLV

QQFADAGIRKSADDSVSAQEKQTLIDHLNQKNSGPDKLTLQRKTRSTLNI

PGTGGKSKSVQIEVRKKRTFVKRDPQEAERLAAEEQAQREAEEQARREAE

ESAKREAQQKAEREAAEQAKREAAEQAKREAAEKDKVTSSEKTFKQRRSL

EQRVEDVRLIREQHPTKIPVIIERYKGEKQLPVLDKTKFLVPDHVNMSEL

IKIIRRRLQLNSNQAFFLLVNGHSMVSVSTPISEVYEREKDEDGFLYMVY

ASQETFGAGTKTEEGKLVIWINGDKGYNGLAEVGKKFEKDTGIKVIVEHP

DKLEEKFPQVAATGDGPDIIFWAHDRFGGYAQSGLLAEITPDKAFQDKLY

PFTWDAVRYNGKLIAYPIAVEALSLIYNKDLLPNPPKTWEEIPALDKELK

AKGKSALMFNLQEPYFTINPLIAADGGYAFKYENGKYDIKDVGVDNAGAK

AGLTFLVDLIKNKHMNADTDYSIAEAAFNKGETAMTINGPWAWSNIDTSK

VNYGVTVLPTFKGQPSKPFVGVLSAGINAASPNKELAKEFLENYLLTDEG

LEAVNKDKPLGAVALKSYEEELAKDPRIAATMENAQKGEIMPNIPQMSAF

WYAVRTAVINAASGRQTVDEALKDAQTNGTGC

EXAMPLES

Methods

Protein sequence alignments were performed using the ClustalW algorithm implemented in Protean version 11.2.1. (DNAStar, Inc.).

Substrate proteins and proteases were over-expressed in *E. coli* strain NEB Express from appropriate low copy expression vectors harboring an ColE1 origin of replication and conferring Kanamycin resistance as described before (Frey, S. and Görlich, D. (2014) *J Chromatogr A* 1337, 95-105). Further sequences are provided on request. Briefly, to produce protease substrates containing MBP as a target protein, *E. coli* cultures containing the appropriate expression vectors were grown with vigorous shaking over night at 30° C. in 50 ml TB medium containing 50 µg/ml Kanamycin (TB-Kan). Cultures were diluted by addition of 300 ml fresh TB-Kan medium and further shaken at 30° C. After 30 min, expression of substrate proteins was induced by addition of IPTG to a final concentration of 200 µM. After 3-4 h, 5 mM EDTA and 1 mM PMSF were added directly to the culture and cells were harvested by centrifugation for 7 min at 5000 g. The cell pellet was resuspended in ice-cold LS buffer (280 mM NaCl, 45 mM Tris/HCl pH 7.5, 4.5 mM $MgCl_2$, 10 mM DTT) containing 15 mM imidazole at a final density of 100 $OD_{600}$. After cell-lysis by sonication, cell debris were removed by centrifugation for 1 h at 200 000×g. The supernatant was incubated with 2 ml of an EDTA- and DTT-resistant $Ni^{2+}$-chelate resin (e.g. Roche cOmplete His-Tag Purification Resin) pre-equilibrated with LS buffer containing 15 mM imidazole for 1 h at 4° C. After washing off unbound proteins with LS buffer containing 15 mM imidazole, polyHis-tagged substrate proteins were eluted with LS buffer containing 300 mM imidazole. After exchanging the buffer to LS buffer using a PD-10 column (GE Healthcare), the substrate protein was mixed with ⅑ volume 2.5 M sucrose. Aliquots were snap-frozen in liquid nitrogen and stored at −80° C. until used.

Protease substrates with fluorescent target proteins (GFP or mCherry), and proteases were produced analogously after expression for 14-16 h at 18° C.

To obtain tag-free protease preparations, imidazole eluates were cleaved to completion with a polyHis-tagged protease appropriate for removal of the polyHis tag. After gel filtration on a SD200 16/60 column (GE Healthcare) pre-equilibrated with LS buffer, remaining traces of cleaved polyHis-tag and polyHis-tagged protease were removed by "reverse $Ni^{2+}$ chelate" chromatography. This guaranteed the final enzyme preparation to be free of any contaminating proteolytic activity. Final protease preparations were diluted with ⅑ volume 2.5 M sucrose. Aliquots ere snap-frozen in liquid nitrogen and stored at −80° C. until used. All proteins were quantified via their absorption at 280 nm and computed extinction coefficients. Accuracy of quantification and purity of the proteins were validated by SDS-PAGE followed by Coomassie-staining.

Cleavage assays in solution and on column were performed as described before (Frey, S. and Görlich, D. (2014) *J Chromatogr A* 1337, 95-105; Frey, S. and Görlich, D. (2014) *J Chromatogr A* 1337, 106-115): If not stated otherwise, cleavage reactions were performed in LS-S buffer (250 mM NaCl, 40 mM Tris/HCl pH 7.5, 2 mM MgCl$_2$, 250 mM sucrose, 2 mM DTT). Generally, substrates and proteases were pre-diluted in LS-S buffer to twice the aspired end-concentration. Cleavage was initiated by mixing identical volumes (generally 5 µl) of substrate and protease pre-dilutions and stopped by mixing with 9 volumes of hot SDS sample buffer. A fraction corresponding to 2.5 µg of substrate was separated by SDS-PAGE on 7-15% gradient gels. Gels were stained with Coomassie G250 and scanned.

On-column cleavage assays were done on EDTA- and DTT-resistant silica- or Sepharose-based Ni$^{2+}$ chelate resins with high porosity.

Dynamic light scattering (DLS): Proteases diluted to 10 µM in LS-S buffer were ultracentrifuged (200 000 g, 30 min), and assayed in a closed cuvette using a DynaPro NanoStar DLS instrument (Wyatt Technology). To acquire heat denaturation curves, the temperature was automatically raised by 1° C. every 10 min. DLS signals were acquired just before each temperature step.

In vitro binding assays: An EDTA- and DTT-resistant Ni$^{2+}$ chelate resin was loaded with 40 µM His$_{14}$-Spacer-xlLC3B-GFP or His$_{14}$-Spacer-xlGATE16-GFP. An empty resin served as a control. 20 µl aliquots were incubated with 100 µl of an equimolar mixture of full-length protease and a protease fragment (10 µM each) for 1 h at 25° C. in LS-S buffer. After washing (3×30 sec) with the same buffer, bound proteins were eluted with SDS sample buffer containing 500 mM imidazole and analyzed by SDS-PAGE.

Example purifications from *E. coli*: Relevant fusion proteins were over-expressed from appropriate expression vectors in *E. coli* (ColE1 origin, Kanamycin resistance). Cleared lysates in LS buffer containing 15 mM imidazole were incubated with an EDTA- and DTT-resistant Ni$^{2+}$ chelate resin. After washing with the same buffer, the target proteins were eluted with 500 nM xlAtg4B$^{14-384}$ in LS buffer at 4° C. After 1 h, proteins remaining on the resin were eluted with LS buffer containing 0.5 M imidazole. Relevant fractions were analyzed by SDS-PAGE.

Samples taken during elution were in addition quantified by measuring the OD$_{280}$.

Substrate Stability in Eukaryotic Extracts:

Rabbit reticulocyte lysate was purchased from Promega, wheat germ extract was prepared according to (Cathrin Enke, Doktorarbeit 2010, Cuvillier Verlag Göttingen, ISBN 978-3-86955-483-9), low-speed *Xenopus* egg extract was prepared according to (Blow, J. J., Laskey, R. A. (1986) *Cell* 47, 577-587). 1.25 µl of 10 µM protease substrates containing MBP as a target protein in LS-S buffer were incubated with 10 µl of indicated lysates in the presence or absence of a protease mix containing scUlp1, SUMOstar protease, xlAtg4B$^{14-384}$ and trAtg4B (0.1 µM each final concentration, supplied in 1.25 µl LS-S buffer) for 2 h at 25° C. in 12.5 µl total volume. Reaction products were analyzed by Western blot with an antibody recognizing *E. coli* MBP (Sigma-Aldrich # M1321).

Yeast Expression:

*S. cerevisiae* strain SFY122 (S288C, Mata, H2B-CFP:: TRP1, his3Δ200, leu2Δ0, lys2Δ0, met15Δ0, ura3Δ0) was transformed with 2µ expression plasmids encoding N-terminally ZZ-UBL-tagged Citrine (Griesbeck, O., Baird, G. S., Campbell, R. E., Zacharias, D. A. and Tsien, R. Y. (2001) *J Biol Chem* 276, 29188-29194; Heikal, A. A., Hess, S. T., Baird, G. S., Tsien, R. Y. and Webb, W. W. (2000) *Proc Natl Acad Sci USA* 97, 11996-12001) under the control of the GAL1 promoter (Sequences are provided on request). Single colonies were grown over night in CSM-Ura containing 2% glucose and 2% raffinose. Cells were washed three times in CSM-Ura +2% raffinose, diluted to OD$_{600}$=0.2 and shaken over night at 30° C. Protein expression was induced by addition of 2% galactose for 5 h. Total lysates were prepared by the NaOH/TCA method (modified from (Riezman, H., Hase, T., van Loon, A. P., Grivell, L. A., Suda, K. and Schatz, G. (1983) *EMBO J* 2, 2161-2168)) and analyzed by Western blot using an antibody recognizing Citrine and CFP. The ZZ-tag was detected using a fluorescently labeled anti-mouse-IgG antibody.

For protein purifications from yeast, cells extracts were prepared by glass bead lysis (modified from (Conzelmann, A., Riezman, H., Desponds, C. and Bron, C. (1988) *EMBO J* 7, 2233-2240)) in LS-S buffer with protease protection. After centrifugation for 1 h at 200 000 g, cleared lysates were incubated with an anti-ZZ affinity resin. Non-bound material was washed off with LS-S buffer and target proteins were eluted with the appropriate protease in the same buffer within 1 h at 4° C. Material remaining on the resin was analyzed after elution with SDS sample buffer.

Example 1

Expression of xlLC3B-Fusions in *E. coli*

Figure 1:
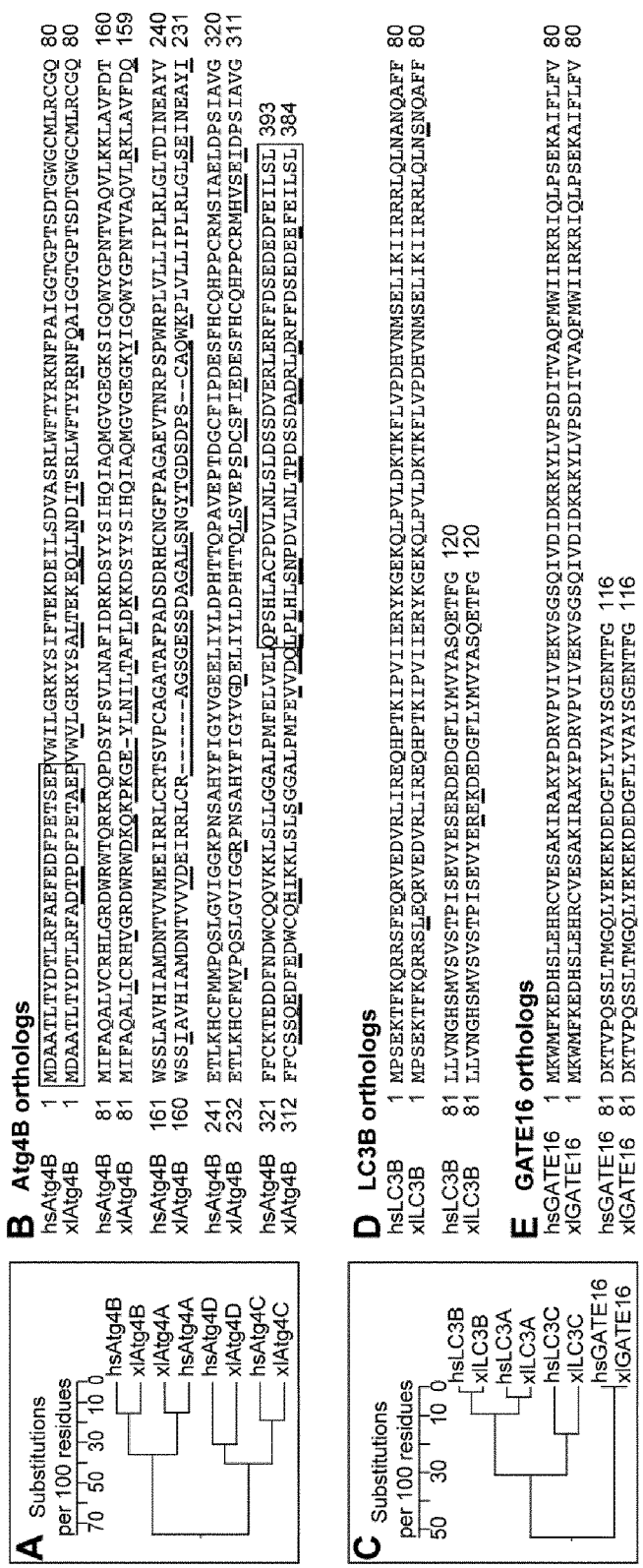
FIG. 1: Alignment of human and *Xenopus laevis* Atg4, LC3 and GATE16 homologs. A, Phylogenetic tree of human (hs) and *Xenopus laevis* (xl) Atg4 homologs. The alignment is based on the ClustalW algorithm. Note that isoforms A to D can be clearly separated in both organisms. B, Sequence alignment of human and *Xenopus laevis* Atg4B homologs. Exchanges with regard to hsAtg4B are underlined. Boxed areas correspond to N- and C-terminal extensions based on the solved structures of human Atg4B (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065; Satoo, K., Noda, N. N., Kumeta, H., Fujioka, Y., Mizushima, N., Ohsumi, Y. and Inagaki, F. (2009) *EMBO J* 28, 1341-1350). C, Phylogenetic tree of human and *Xenopus laevis* LC3 and GATE16 homologs. Note that GATE16 forms a separate branch and can be clearly separated from the LC3 isoforms. D and E, Sequence alignment of human and *Xenopus laevis* LC3B and GATE16 orthologs, respectively. Exchanges with regard to the human proteins are underlined. Mature human and *Xenopus laevis* GATE16 proteins share identical primary sequences. xlAtg4B is SEQ ID NO:1, xlLC3B is SEQ ID NO:2, xlGATE16 is SEQ ID NO:4, hsAtg4B is SEQ ID NO:19, hsLC3B is SEQ ID NO20, and hsGATE16 is listed as SEQ ID NO: 21.
Figure 2:
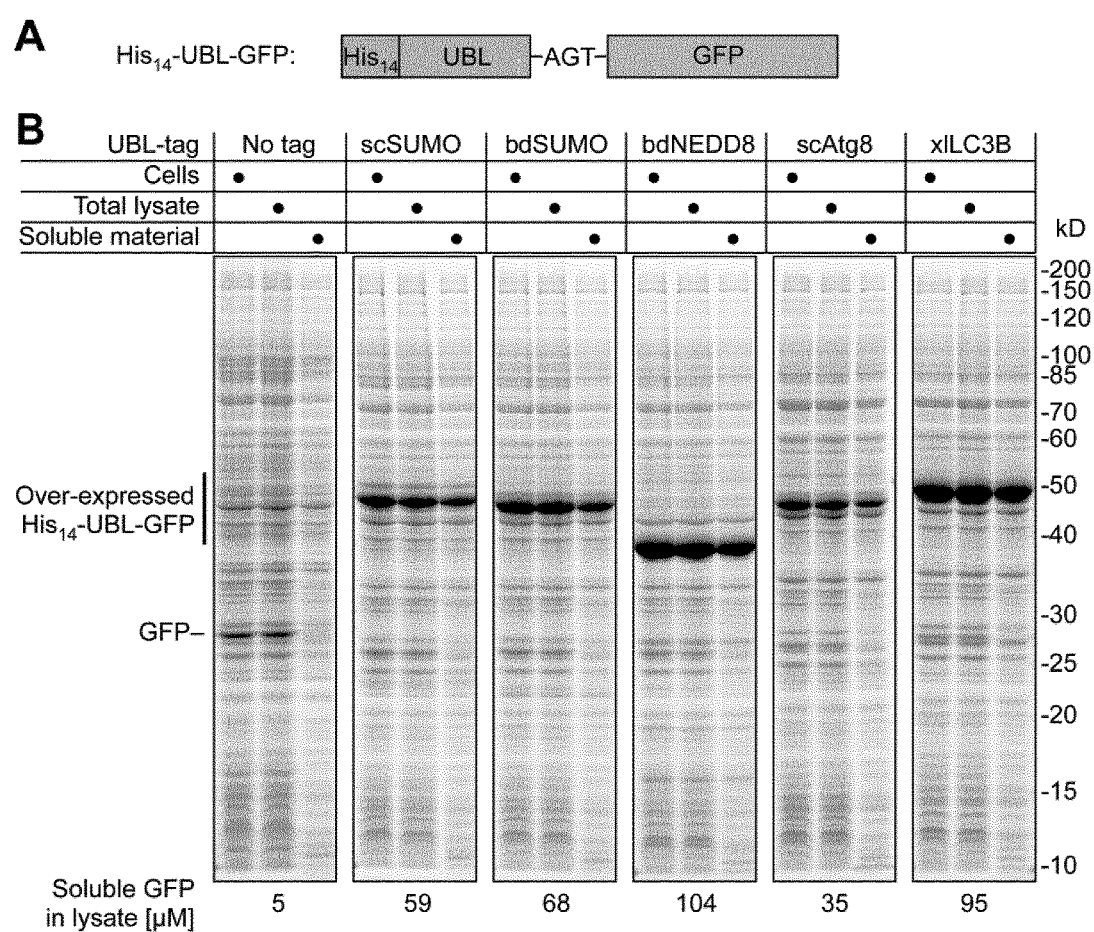
FIG. 2: Expression level and solubility of His$_{14}$-UBL-tagged GFP. Proteins sketched in (A) were over-expressed as described in the section "Methods" in the Examples section below from appropriate expression vectors in *E. coli* strain NEB Express for 16 h at 18° C. Equal amounts of resuspended cells, total lysate and soluble material were analyzed by SDS-PAGE (B). GFP present in the soluble fraction was quantified via its absorbance at 488 nm. Note that scAtg8 promotes significantly lower expression levels than the other UBLs.

Initially, the primary aim was to analyze the suitability of xlAtg4B for tag removal from recombinant proteins fused to *Xenopus laevis* Atg8 orthologs. As the inventors had observed before that fusions to *S. cerevisiae* Atg8 only show suboptimal expression levels (Frey, S. and Görlich, D. (2014) *J Chromatogr A* 1337, 95-105), the inventors first compared the impact of various UBLs including xlLC3B on expression and solubility of GFP (FIG. 2). Indeed, xlLC3B-GFP could be highly over-expressed in *E. coli* and produced nearly 3-times higher levels of soluble GFP as compared to the corresponding scAtg8 fusion. Remarkably, with regard to the expression level, both xlLC3B and bdNEDD8 clearly outperformed scSUMO, which is well known for its expression- and solubility-enhancing effects.

Example 2

Figure 3:
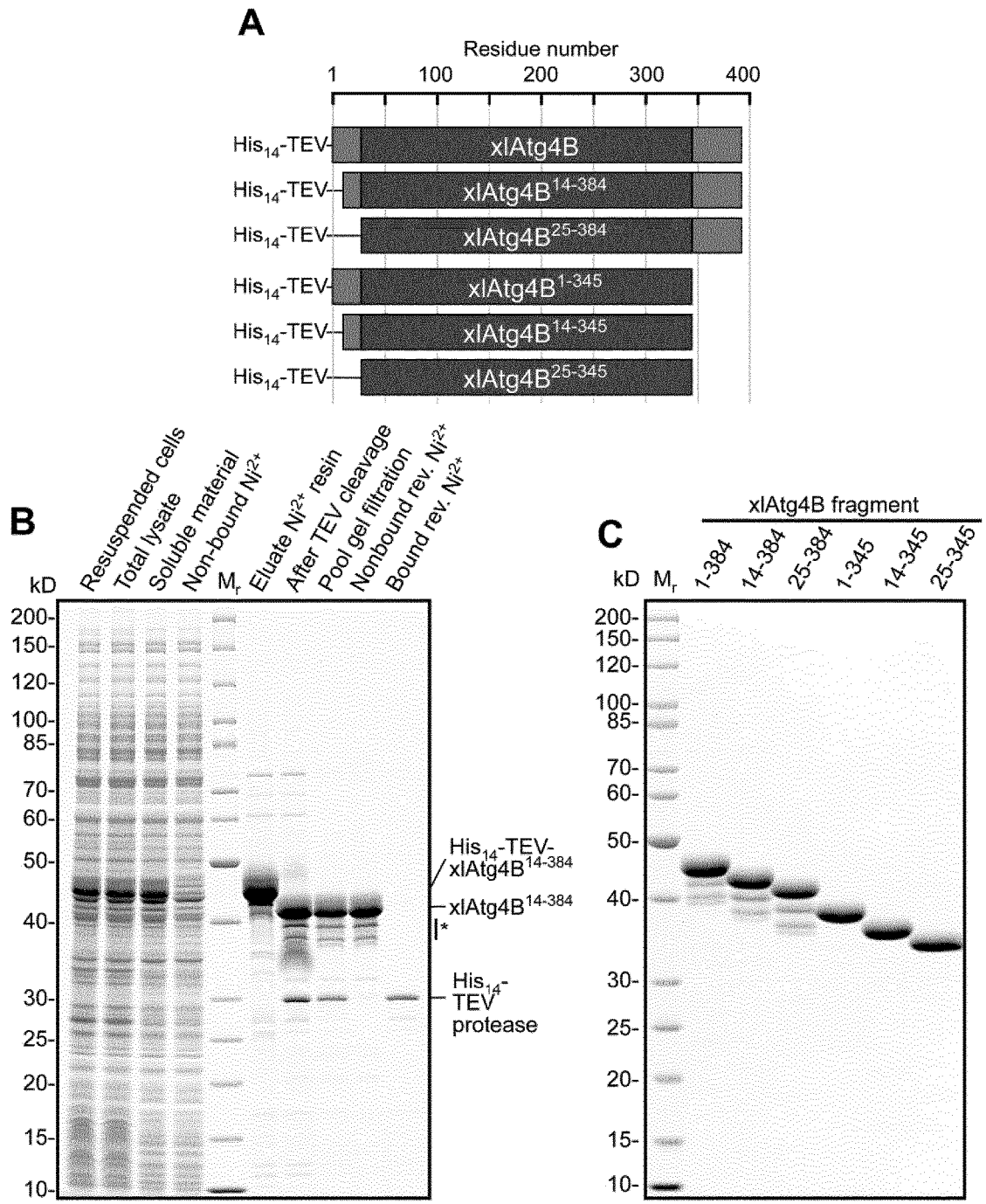
FIG. 3: Purification of xlAtg4B protease fragments. A, Schematic illustration of expression constructs used for (B) and (C). B, Exemplary purification of xlAtg4B$^{14-384}$. His$_{14}$-TEV-xlAtg4B$^{14-384}$ was over-expressed from an appropriate expression vector in *E. coli* strain NEB Express. After cell lysis and centrifugation, the soluble material was applied to a Ni$^{2+}$ chelate resin. Bound proteins were eluted with imidazole and treated with polyHis-tagged TEV protease over night at 4° C. before loading on a Superdex 200 gel filtration column. The pooled peak fractions mainly containing cleaved xlAtg4B$^{14-384}$ and TEV protease were subjected to a reverse Ni$^{2+}$ chromatography step (rev. Ni$^{2+}$). Here, the polyHis-tagged TEV protease bound to the resin while pure xlAtg4B$^{14-384}$ was found in the non-bound fraction. Purification of other xlAtg4B fragments was done identically. The remaining degradation bands (*) are specific for protease fragments containing the full-length C-terminus. C, Purity of xlAtg4B protease fragments. 40 pmol (≈1.6 μg) of purified protease fragments were analyzed by SDS-PAGE and Coomassie-staining.

Identification and Characterization of xlAtg4B Protease and xlAtg4B Protease Fragments As a next step, the inventors wanted to find well-expressible and well-soluble xlAtg4B fragments displaying optimal stability and catalytic properties. Based on known structures of the human Atg4B homolog (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065; Satoo, K., Noda, N. N., Kumeta, H., Fujioka, Y., Mizushima, N., Ohsumi, Y. and Inagaki, F. (2009) *EMBO J* 28, 1341-1350), full-length xlAtg4B (residues 1-384) and five shorter xlAtg4B fragments harboring N- and/or C-terminal truncations (xlAtg4B$^{14-384}$, xlAtg4B$^{25-384}$ xlAtg4B$^{1-345}$, xlAtg4B$^{14-345}$ and xlAtg4B$^{25-345}$) were cloned and expressed. All proteases fragments could be over-expressed in *E. coli* and obtained in high yield and purity (FIG. 3). Typical yields of the pure proteases were >120 mg per liter culture, i.e. 10-20 times more than obtained for the yeast ortholog scAtg4 (typically 5-10 mg).

To compare their catalytic properties efficiencies, a subset of these protease fragments was assayed in various in vitro cleavage assay (Frey, S. and GOrlich, D. (2014) *J Chro-*

Figure 4:
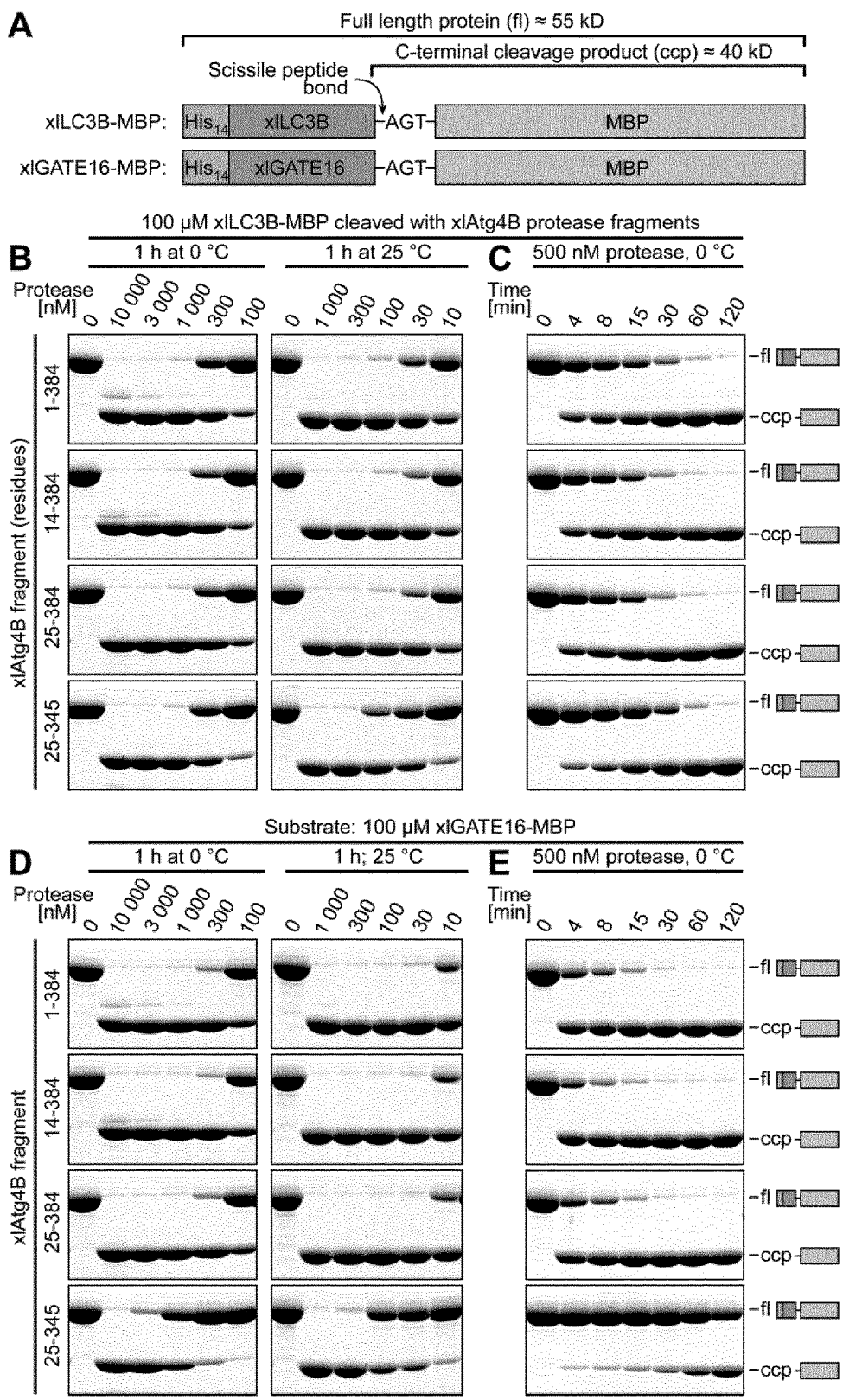
FIG. 4: In-vitro assay for xlAtg4B activity. A, Schematic representation of the protease substrates xlLC3B-MBP (top) and xlGATE16-MBP (bottom). Both fusion proteins contain an N-terminal polyHis-tag, a protease recognition site (xlLC3B or xlGATE16) and MBP (*E. coli* maltose binding protein, MBP) as a model target protein. To ensure a comparable accessibility, the scissile bond is followed by the identical tri-peptide (AGT; Ala-Gly-Thr) in both substrate proteins. For simplicity, substrate names do not contain the polyHis-tag. B, Protease titration. The substrate xlLC3B-MBP (100 μM) was incubated for 1 h at 0° C. (left) or 25° C. (right) in the presence of a defined concentrations of indicated proteases. Cleavage products were separated by SDS-PAGE and stained with Coomassie G250. Shown are full-length substrate proteins (fl) and the C-terminal cleavage products (ccp). C, Time course. 100 μM of xlLC3B-MBP was incubated at 0° C. with 500 nM of indicated protease fragments. At indicated time points, aliquots were withdrawn and analyzed as described in (C). D and E, Protease titration and time course with the xlGATE16-MBP substrate were performed in parallel to the corresponding experiments described in (C) and (D).

*matogr A* 1337, 95-105) using two analogous substrate proteins with different xlAtg4B protease recognition sites (xlLC3B or xlGATE16, respectively; FIG. 4A). For a direct comparison, all reactions of a given experimental setups were performed in parallel for all analyzed protease fragments and substrates. In a first setup, the inventors titrated the protease concentration and assayed the cleavage of substrate proteins at 0° C. and 25° C., respectively (FIGS. 4B and D). At 0° C., all four proteases cleaved the xlLC3B substrate with similar efficiency: 1 µM of each protease fragment was sufficient to cleave 100 µM of substrate within 1 h (FIG. 4B, left panel). At closer inspection, however, it became apparent that the C-terminal truncation within xlAtg4B$^{25-345}$ slightly impaired xlLC3B processing while the two N-terminally shortened protease fragments were similarly active as the full-length enzyme. These subtle differences were more obvious when analyzing the cleavage kinetics using a fixed protease concentration (FIG. 4C): Here, efficient cleavage (i.e. >95% cleavage) of the xlLC3B substrate required twice as long when using xlAtg4B$^{25-345}$ instead of the full-length or just N-terminally truncated xlAtg4B enzymes. At 25° C., about 10-fold less full-length or N-terminally truncated protease was required for efficient xlLC3B cleavage (FIG. 4B, right panel). Thus, the C-terminal deletion caused at 25° C. a more drastic loss in activity than at 0° C. Compared to the xlLC3B substrate, processing of the xlGATE16 substrate was generally more efficient and required 2- to 3-fold less full-length or N-terminally truncated proteases at either temperature (FIG. 4D). xlGATE16 processing was, however, strikingly more sensitive towards the C-terminal protease truncations: ≈10-fold and ≈30-fold more xlAtg4B$^{25-345}$ was required for xlGATE16 processing as compared to the other protease fragments at 0° C. and 25° C., respectively. Consistently, 500 nM of xlAtg4B$^{25-345}$ were insufficient to cleave 100 µM of xlGATE16 substrate within 2 h at 0° C. (FIG. 4E). As with the xlLC3B substrate, no significant differences in activity could be observed between full-length and N-terminally truncated xlAtg4B fragments.

Salt Sensitivity

Figure 5:
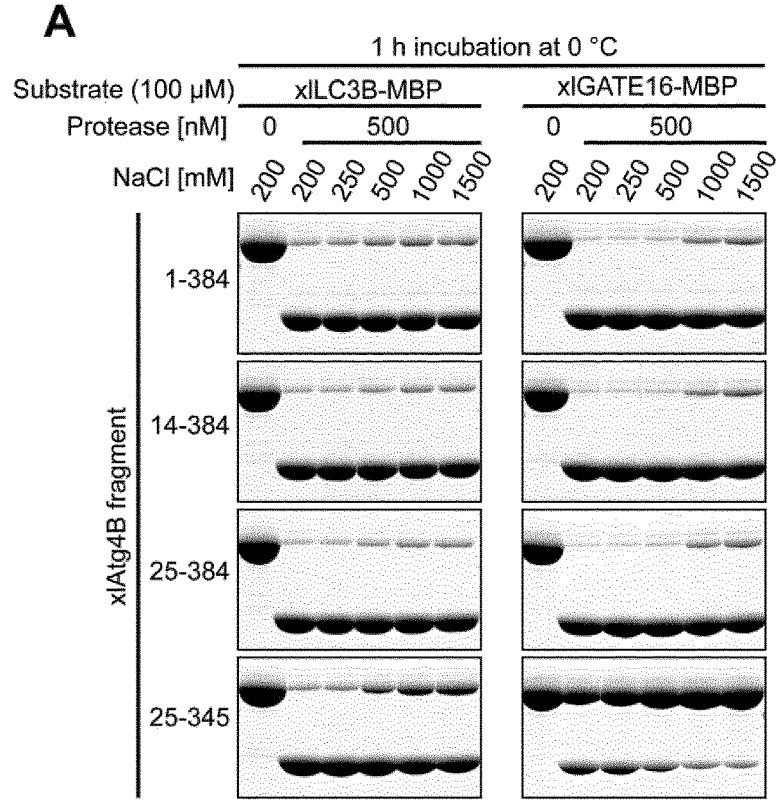
FIG. 5: Salt sensitivity and temperature dependence. A, Salt sensitivity. 100 μM of xlLC3B-MBP (left) or xlGATE16-MBP (right) were incubated for one hour at 0° C. with 500 nM protease fragments at NaCl concentrations ranging from 0.2 to 1.5 M. B, Temperature dependence. Indicated xlAtg4B fragments were incubated with 100 μM of xlLC3B-MBP (left) or xlGATE16-MBP (right) for 1 h at defined temperatures. Note that in comparison to the xlGATE16-MBP substrate, twice as much protease was used for cleavage of the xlLC3B-MBP substrate.
Figure 5:
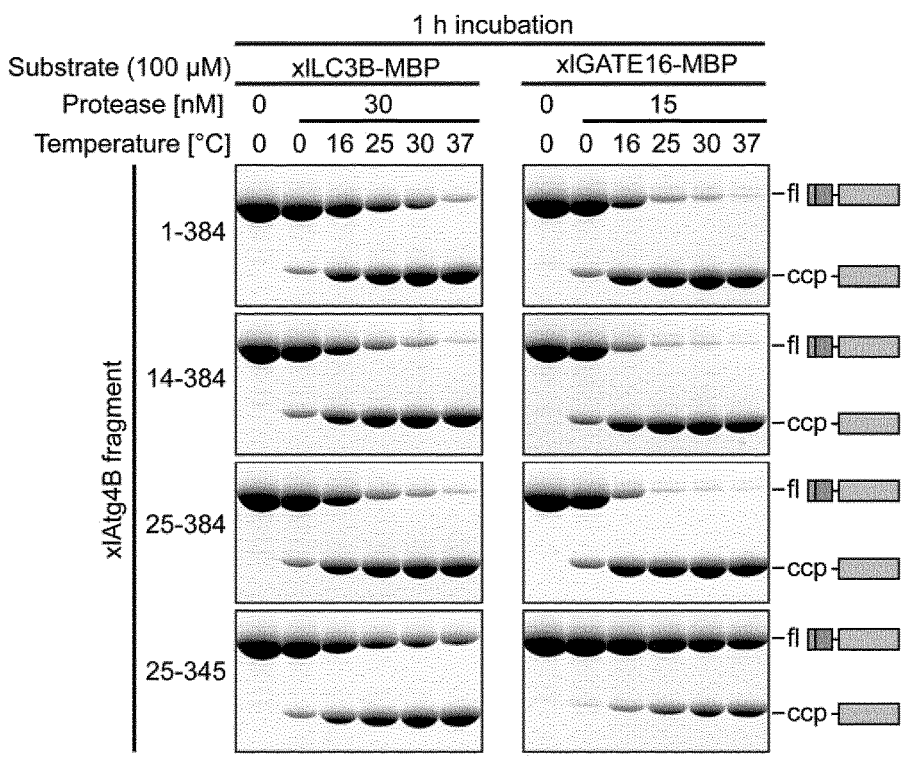

To learn more about the nature of the possible interaction between xlAtg4B and its substrates xlLC3B and xlGATE16, the inventors next tested the salt sensitivity of substrate processing. To this end, each substrate was incubated with 500 nM of each protease for 1 h at 0° C. at defined salt concentrations (FIG. 5A). Strikingly, xlLC3B processing by full-length xlAtg4B or its N-terminally truncated fragments was remarkably insensitive towards NaCl concentrations up to 1.5 M. Deletion of the protease's C-terminus, however, rendered the reaction salt sensitive at NaCl concentrations ≥0.5 M (FIG. 5A, left). In contrast to the xlLC3B substrate, xlGATE16 processing was generally more salt sensitive (FIG. 5A, right): Here, also full-length or N-terminally truncated xlAtg4B fragments showed a reduced cleavage activity at ≥1 M NaCl. The weak activity of xlAtg4B$^{25-345}$ on xlGATE16 was further reduced at salt concentrations ≥0.5 M.

Temperature Dependence

Next, the temperature dependence of substrate processing by the xlAtg4B fragments was analyzed (FIG. 5B). As expected, the efficiency of xlLC3B cleavage increased with increasing temperature for all protease fragments (FIG. 5B, left). The full-length enzyme showed a remarkable activity boost between 16 and 37° C. A similar boost could be observed already between 0° C. and 25° C. for the two N-terminally truncated protease fragments. Within 1 h at 37° C., all three enzymes were able to cleave a >3000-fold excess of the xlLC3B substrate to near completion. At 0° C., also the protease fragment lacking the C-terminal extension was similarly active as the other three fragments tested. The boost of xlLC3B substrate processing at higher temperatures, however, was much weaker for this protease fragment. A similar general trend was observed also for the xlGATE16 substrate (FIG. 5B, right). Here, however, near-complete cleavage of a 6600-fold substrate excess was reached for the two N-terminally shortened protease fragments already at 25° C., while the full-length enzyme required 37° C. for a similarly efficient cleavage. The C-terminally shortened xlAtg4B$^{25-345}$ fragment could only cleave ≈30-40% of a 6600-fold substrate excess even at 37° C.

xlAtg4B C-terminus

The results herein thus far show that deletion of the C-terminal xlAtg4B extension significantly impairs substrate processing, especially when using the xlGATE16 substrate at higher temperatures or elevated NaCl concentrations. Three possible explanations could possibly account for these effects: (i) The C-terminus of xlAtg4B might be required for enzymatic turnover, (ii) it could contribute to substrate recognition or (iii) be required for xlAtg4B stability. In the following, these scenarios were tested individually.

Figure 6:
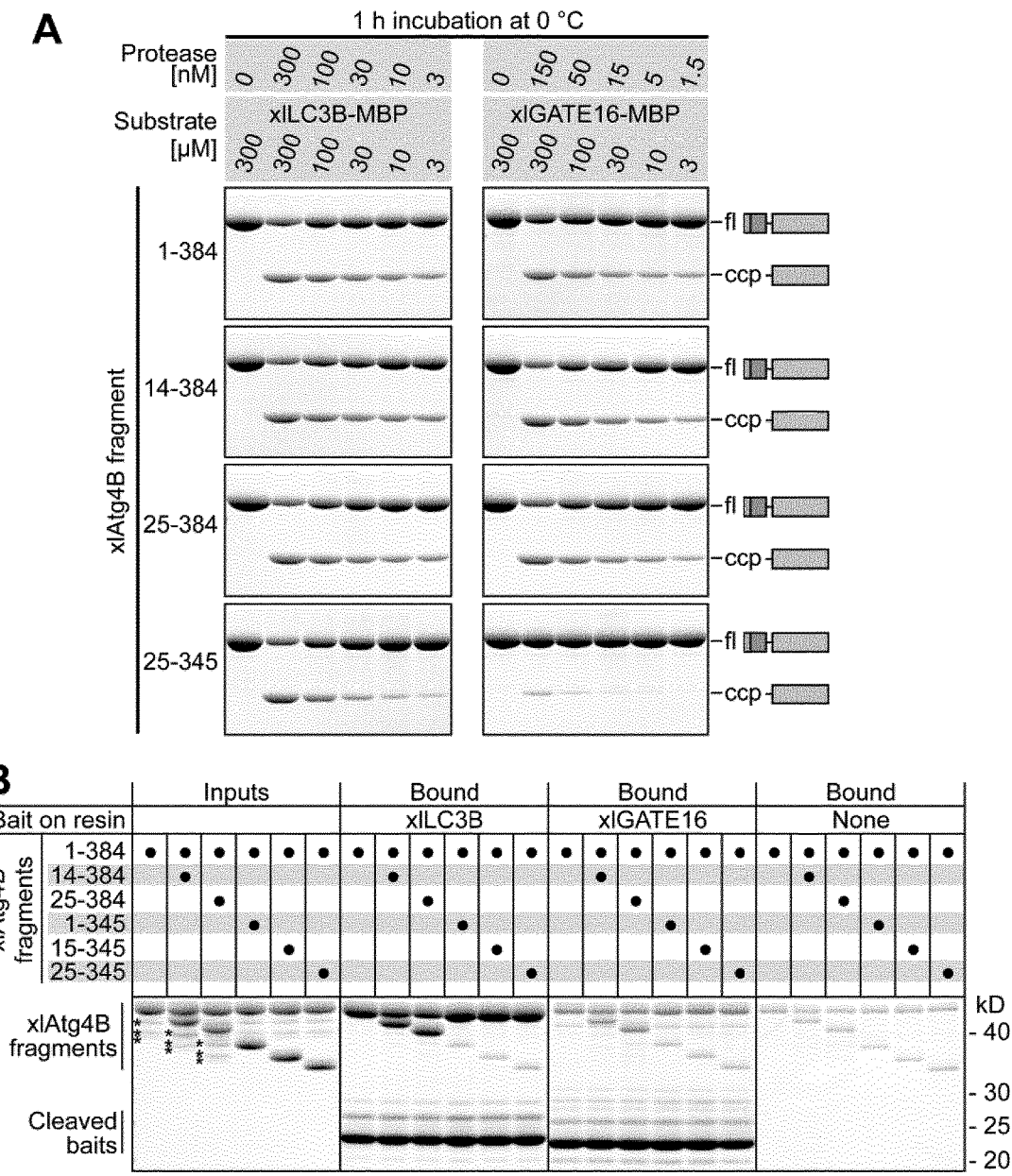
FIG. 6: Substrate recognition. A, Cleavage efficiency at limiting substrate concentrations. The concentration of indicated protease fragments and the substrates xlLC3B-MBP (left) or xlGATE16-MBP (right) was titrated at constant protease: substrate ratio (1:1000 or 1:2000, respectively). After cleavage (1 h at 0° C.), a fraction of each reaction corresponding to 1.2 μg (≈20 pmol) of substrate protein was analyzed by SDS-PAGE. Due to the different substrate concentrations, the absolute volume of the cleavage reaction analyzed by SDS-PAGE had to be adjusted accordingly. B, Competitive binding of xlAtg4B fragments to immobilized xlLC3B and xlGATE16. An equimolar mixture of full-length xlAtg4B and indicated fragments (10 μM each) was incubated with immobilized xlLC3B or xlGATE16. A resin without bait protein (right panel) served as a specificity control. Bound proteins were analyzed by SDS-PAGE. xlAtg4B degradation products lacking parts of the C-terminal extension are marked with an asterisk (*) in the input fractions. Note that binding is markedly reduced for protease fragments harboring C-terminal deletions. The pull-down efficiency is generally higher when using xlLC3B instead of xlGATE16 as a prey.

First, the cleavage efficiency of the xlAtg4B fragments at different dilutions was analyzed (FIG. 6A). Within one set of reactions, the concentrations of both, substrate and protease were varied proportionally while keeping the initial substrate/protease ratio constant. Strikingly, at 300 µM concentration of xlLC3B substrate, all protease fragments were similarly active, clearly showing that the C-terminus of xlAtg4B is dispensable for general enzymatic turnover (FIG. 6A, left). At higher dilutions, however, clear differences became apparent: While full-length xlAtg4B and both N-terminally shortened fragments could cleave the xlLC3B substrate rather efficiently even at substrate concentrations as low as 3-10 µM, the C-terminally truncated protease showed significantly reduced cleavage already at 100-30 µM substrate concentration (FIG. 6A, left lower panel).

At high concentrations, also the xlGATE16 substrate was efficiently cleaved by the full-length protease or both N-terminally truncated fragments (FIG. 6A, right). xlGATE16 processing, however, significantly dropped already at substrate concentrations lower than ≈30 µM. Even more drastic effects were observed when cleaving xlGATE16-MBP with xlAtg4B$^{25-345}$ (FIG. 6A, right lower panel). Here, processing was poor even at 300 µM substrate concentration. These results clearly indicate that a deletion of the C-terminal protease extension does not impair the enzymatic turnover but rather prevents efficient substrate recognition at high dilutions. In general, the xlGATE16 substrate is more sensitive to dilution indicating that the Michaelis-Menten constant ($K_M$) of the reaction is higher for xlGATE16 than for xlLC3B substrates.

To directly compare binding of N- and/or C-terminally shortened protease fragments with the full-length enzyme, competitive pull-down assays using equimolar binary protease mixtures as a prey were performed (FIG. 6B). In this setup, even small differences in affinity should affect the relative protease stoichiometries between the input and the bound fractions. xlLC3B pulled down a 1:1 mixture of full-length xlAtg4B and the N-terminally shortened fragments. The N-terminal protease truncations hence did not influence binding. Interaction of all protease fragments lacking the C-terminal extension was, however, reduced to background levels in the presence of full-length protease. Interestingly, also degradation products lacking less than 39 residues from the C-terminus (unintentionally present in the enzyme preparations) bound xlLC3B far less efficiently than the respective enzymes with full-length C-termini, showing that even the extreme C-terminus is required for full substrate binding. Similar results were obtained when using xlGATE16 as a bait. The interaction of all proteases with xlGATE16 was, however, significantly weaker than with xlLC3B.

Together, the experiments so far clearly show that xlAtg4B's C-terminal extension substantially contributes to recognition of both xlLC3B and xlGATE16 and is therefore required for robust substrate cleavage.

Thermal Stability

Figure 7:
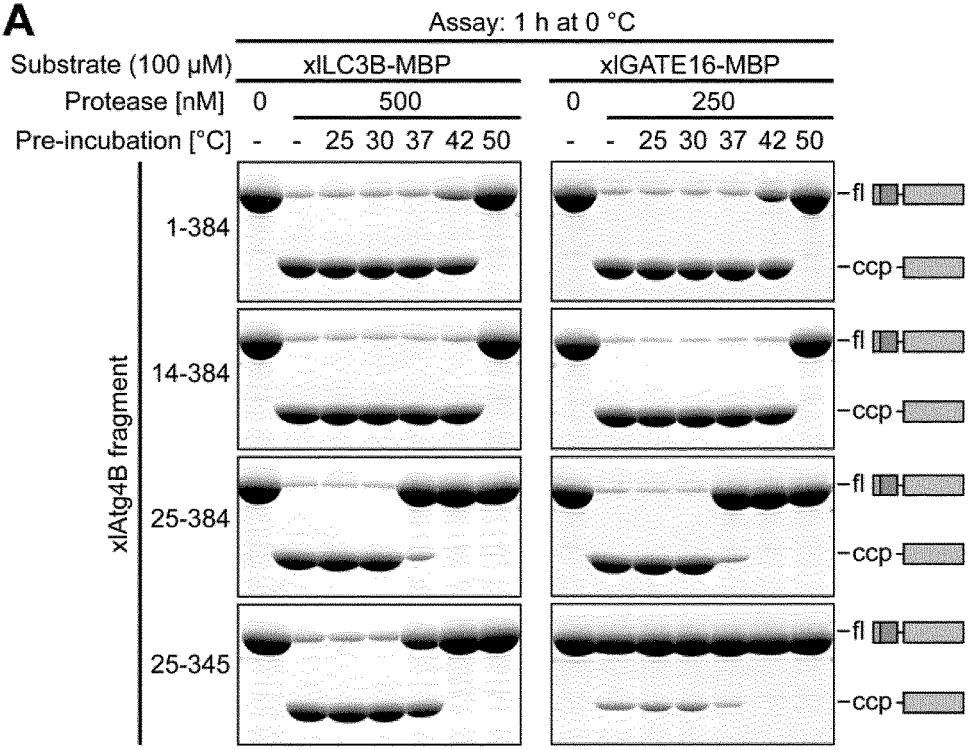
FIG. 7: Thermal stability. A, Long-term temperature stability. xlAtg4B fragments were pre-incubated for 16 h at indicated temperatures in the presence of 20 mM DTT under argon to protect the active site cysteines from oxidation. The remaining activity was then assayed by treating 100 μM of xlLC3B or xlGATE16 substrate with each protease for 1 h at 0° C. B, Thermal denaturation of xlAtg4B fragments followed by dynamic light scattering. C, Long-term DLS measurement of xlAtg4B$^{25-384}$. DLS signals were acquired for ≈20 h while incubating xlAtg4B$^{25-384}$ at 37° C. with protection from oxidation. Note that at this temperature the protease appears rather stable for ≈2 h. At longer incubation, a gradual increase in average particle size is observed, indicating slow denaturation and aggregate formation.
Figure 7:
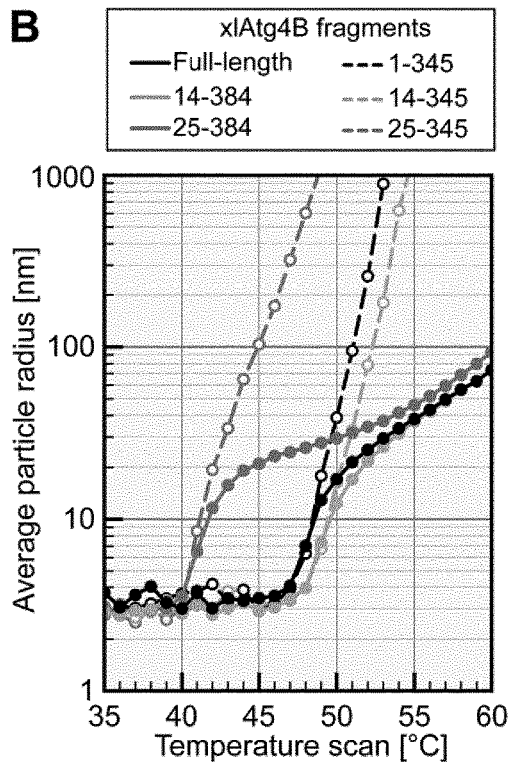
Figure 7:
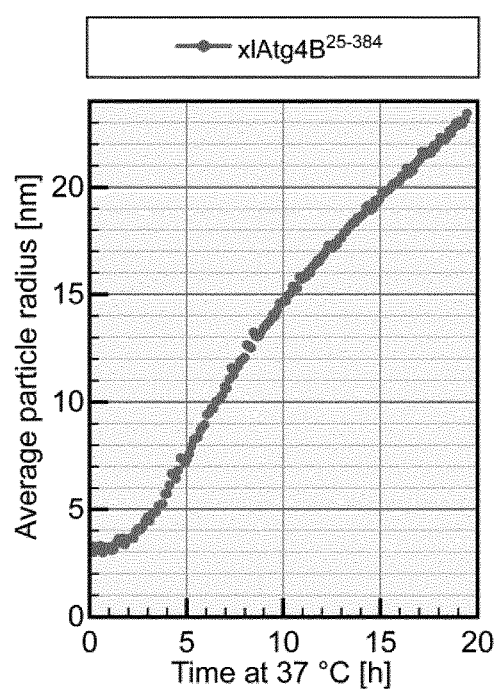

The inventors next asked if the N- and C-terminal extensions influence the (thermal) stability of xlAtg4B. To this end, all xlAtg4B fragments were pre-incubated for 16 h at different temperatures before analyzing their remaining activity in a standard xlLC3B cleavage assay (FIG. 7A, left). In this assay, the full-length enzyme retained full activity after over-night incubation at 37° C., but lost activity at higher temperatures. xlAtg4B$^{14-384}$ was more temperature stable and survived at least 42° C. for 16 h. A drastic loss in activity was, however, observed already at 37° C. for both enzyme fragments lacking the N-terminal 24 residues. Identical effects were obtained when using the xlGATE16 substrate (FIG. 7A, right).

In a second assay, dynamic light scattering (DLS) was used to analyze the thermal denaturation of the xlAtg4B fragments (FIG. 7B). The full-length enzyme started to unfold at 47-48° C. Fragments lacking the N-terminal 13 residues were slightly stabilized while an N-terminal deletion of 24 residues reduced the temperature stability by 7-8° C. All tested enzymes with an intact C-terminus showed biphasic denaturation curves, pointing to distinct steps of initial unfolding and subsequent aggregation (FIG. 7B). A deletion of the C-terminal extension did not significantly change the onset of denaturation (FIG. 7B, compare solid with dashed lines), but promoted subsequent aggregate formation. The strongly negatively charged C-terminus might thus act as a solubility enhancer that prevents immediate aggregation.

Interestingly, the temperatures required to observe an initial decline of enzymatic activity (FIG. 7A) were generally ≈5° C. lower than the onset of thermal denaturation observed by DLS (FIG. 7B). This discrepancy could be resolved by long-term DLS experiment with xlAtg4B$^{25-384}$ at 37° C. (FIG. 7C): Here, during the initial two hours of incubation, the protease appeared rather stable. At longer incubation, however, xlAtg4B$^{25-384}$ started to unfold and aggregate. The discrepancy between the activity assay (after 16 h of thermal denaturation) and the DLS experiment (temperature increase 1° C. per 10 min) can thus most likely be explained by the different experimental time-scales.

Promiscuity for Residues in the $P_1'$ Position

Figure 8:
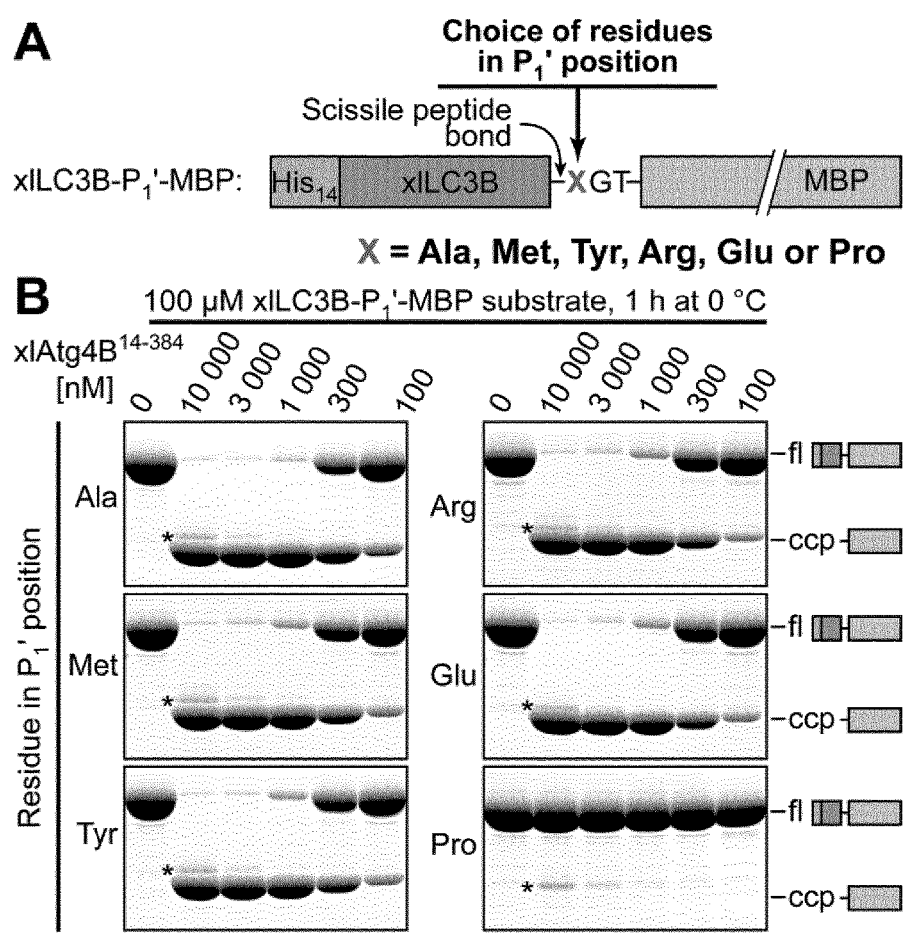
FIG. 8: P$_1$' preference of xlAtg4B$^{14-384}$. A, Protease substrates used to analyze the P$_1$' preference of xlAtg4B$^{14-384}$ follow the general outline shown in FIG. 4A. Here, however, the P$_1$' position of the P$_1$-P$_1$' scissile bond had been mutated to the potentially non-preferred residues methionine (Met), tyrosine (Tyr), arginine (Arg), glutamic acid (Glu), or proline (Pro). B, Solution cleavage assay with P$_1$' substrates sketched in (A). Bands marked with an asterisk (*) refer to the protease.

The experiments herein show that xlAtg4B$^{14-384}$ combines optimal enzyme stability with efficient and robust substrate cleavage. The inventors further analyzed the properties of this protease fragment with respect to in-vitro cleavage of recombinant proteins. If target proteins with a defined (e.g. the authentic) N-terminus are to be produced, the enzyme's sensitivity to the residue in the $P_1'$ position (i.e. the residue following the scissile bond; FIG. 8A) is an important parameter. An optimal enzyme will offer a maximal freedom to choose any desired residue in the $P_1'$ position. Therefore, the protease concentration required for cleavage of several analogous substrates with altered residues in the $P_1'$ position was analyzed. Surprisingly, the enzyme showed remarkable promiscuity and required only slightly more protease for efficient cleavage of substrates harboring Met, Tyr, Arg or Glu in the $P_1'$ position as compared to the original $P_1'_{Ala}$ substrate. The enzyme, however, was unable to process a $P_1'_{Pro}$ substrate.

Discussion

Based on the known structure of the human Atg4B ortholog (hsAtg4B) (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065; Satoo, K., Noda, N. N., Kumeta, H., Fujioka, Y., Mizushima, N., Ohsumi, Y. and Inagaki, F. (2009) *EMBO J* 28, 1341-1350), a series xlAtg4B fragments with N-terminal and C-terminal truncations was designed. At low temperature, the analyzed N-terminally truncated xlAtg4B fragments (xlAtg4B$^{14-384}$ and xlAtg4B$^{25-384}$) showed a catalytic activity comparable to the full-length enzyme. While these results seem to be in contrast to earlier studies on the human Atg4B ortholog that suggested an auto-inhibitory function of the N-terminal extension (Li, M., Hou, Y., Wang, J., Chen, X., Shao, Z. M. and Yin, X. M. (2011) *J Biol Chem* 286, 7327-7338; Satoo, K., Noda, N. N., Kumeta, H., Fujioka, Y., Mizushima, N., Ohsumi, Y. and Inagaki, F. (2009) *EMBO J* 28, 1341-1350), the inventors observed that at temperatures ≥16° C., indeed the two shorter fragments were slightly more active than the full-length enzyme. Without being bound by theory, this temperature effect could potentially be a result of several hydrophobic interactions that are observed between the N-terminal extension of the human enzyme and the protease surface near the catalytic center. Importantly, deletion of only 13 N-terminal residues was sufficient to efficiently prevent auto-inhibition and in addition created an enzyme fragment (xlAtg4B$^{14-384}$) with superior temperature stability compared to xlAtg4B$^{25-384}$.

The contribution of the flexible C-terminal protease extension (residues 346-384) to substrate recognition and processing was also analyzed. While the significance of this region so far had not been directly addressed, it was now found compelling evidence that it is required for an efficient interaction with two dedicated xlAtg4B substrate proteins, xlLC3B and xlGATE16. This finding was surprising for two reasons. First, the available structures of the substrate-free human Atg4B (hsAtg4B) suggest that the protease's C-terminus partially occupies the substrate-binding site (Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618; Sugawara, K., Suzuki, N. N., Fujioka, Y., Mizushima, N., Ohsumi, Y. and Inagaki, F. (2005) *J Biol Chem* 280, 40058-40065). It therefore has to be displaced before substrate binding can occur, which may thus hamper formation of the protease-substrate complex. Second, crystals of LC3B-bound hsAtg4B could be obtained only after removal of the C-terminal extension (Satoo, K., Noda, N. N., Kumeta, H., Fujioka, Y., Mizushima, N., Ohsumi, Y. and Inagaki, F. (2009) *EMBO J* 28, 1341-1350), which (i) shows that the C-terminus of xlAtg4B is not strictly required for substrate interaction and (ii) could indeed suggest an inhibitory effect on complex formation. In contrast, the results herein clearly show that the C-terminal extension is an integral part of the protease's substrate interaction surface.

While the C-terminal protease truncation affects processing of xlLC3B mainly under stringent conditions (high salt, elevated temperature or low substrate concentration), the effect is pronounced already under standard conditions (0° C., 250 mM NaCl, 100 µM initial substrate concentration) when using the xlGATE16 substrate. This striking difference might be attributed to the overall lower affinity of xlGATE16 to xlAtg4B as compared to xlLC3B (see FIG. 6). In addition the data herein indicates that the interaction between xlGATE16 and xlAtg4B is strongly dependent on protease's C-terminus while xlLC3B significantly interacts also with the folded protease domain. Although the C-terminally truncated protease fragment shows similar temperature stability as the corresponding full-length variant, impairment of substrate cleavage is stronger at higher temperatures. This suggests that the interaction of substrates with the protease core is mainly ionic (and thus weakened at higher temperatures) while interaction with the C-terminal extension involves a strong hydrophobic component. This conclusion is also in line with the observation that all protease fragments with intact C-termini robustly cleave the xlLC3B substrate at both high salt conditions and low temperature, suggesting that hydrophobic as well as ionic interactions participate in the proteasesubstrate interaction.

In combination, the folded core and the C-terminal extension of xlAtg4B mediate a strong interaction with the xlLC3B substrate, which is beneficial for efficient substrate processing at high dilution and complete processing of substrates. Strikingly, however, the turnover rate at high substrate concentrations is clearly lower for xlLC3B as compared to the xlGATE16 substrate, which has a lower affinity to the protease. Without being bound by theory, this seemingly paradoxical finding suggests that the rate-limiting step in xlAtg4B-mediated substrate cleavage is the substrate release. As a consequence, cleavage of xlLC3B substrates is slower but more robust.

Example 3

Figure 9:
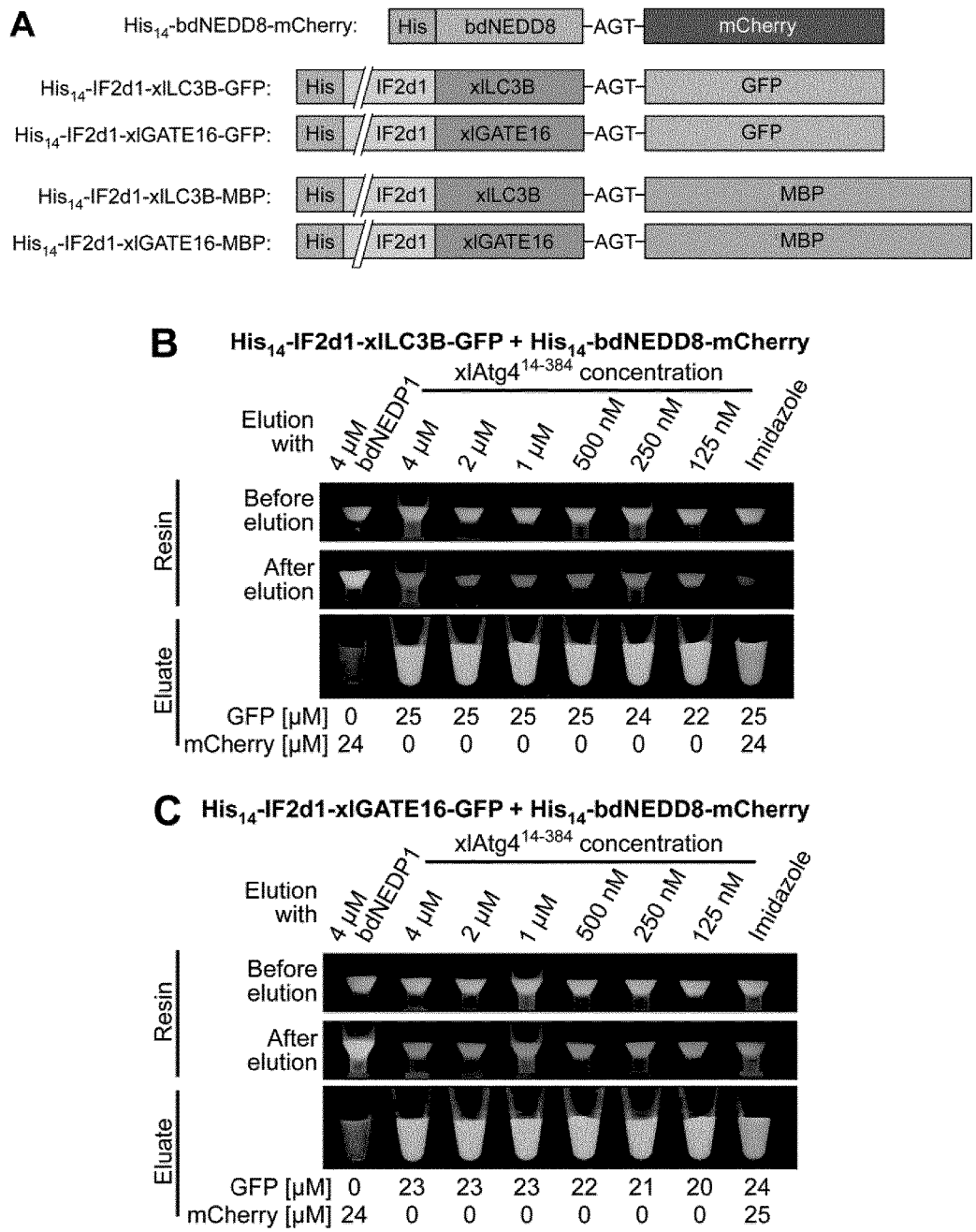
FIG. 9: On column cleavage using xlAtg4B$^{14-384}$. A, Schematic representation of substrate proteins used in (B)-(E). The N-terminal domain of *E. coli* IF2 (IF2d1 (58, 59)) serves as a spacer. B and C, A silica-based Ni$^{2+}$ chelate resin was pre-loaded with similar amounts of His$_{14}$-bdNEDD8-mCherry and either His$_{14}$-IF2d1-xLC3B-GFP (B) or His$_{14}$-IF2d1-xlGATE16-GFP (C). 50 μl aliquots were treated with indicated concentrations xlAtg4B$^{14-384}$ for 1 h at 4° C. Control incubations were performed with 4 μM bdNEDP1 or with buffer containing 400 mM imidazole. Resins and eluates were photographed while illuminated at 366 nm. GFP and mCherry in the eluate fractions were quantified via their specific absorption. Quantification results are given below the respective eluate fractions. D and E, Protein purification using on-column cleavage by xlAtg4B$^{14-384}$. Indicated substrates were over-expressed from appropriate expression vectors in *E. coli* strain NEB Express. After lysis and ultracentrifugation, the soluble material was incubated with a Ni$^{2+}$ chelate resin. The resin was washed and treated with 500 nM xlAtg4B$^{14-384}$ at 4° C. At indicated time points, the concentration and purity of the released MBP was determined using the calculated absorption coefficient at 280 nm (OD$_{280}$) and SDS-PAGE, respectively. Proteins remaining on the resin after 60 min were eluted by 500 mM imidazole. The time course of elution is shown in (D), the OD$_{280}$ reading at 60 min elution time was set to 100%. Relevant steps of the purifications are shown in (E).
Figure 9:
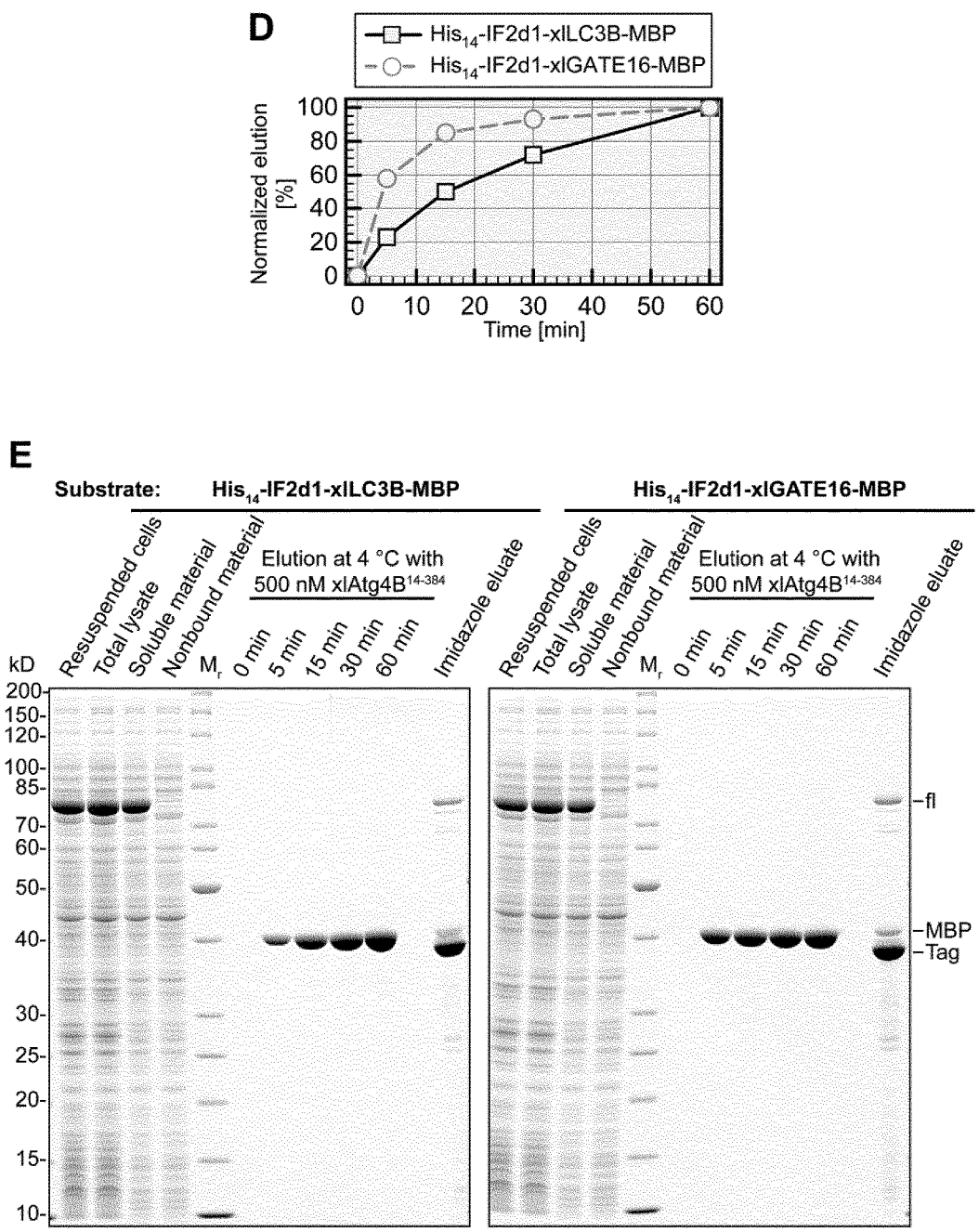

Application of the xlAtg4B Protease System for Tag Removal and On-Column Cleavage An important application of tag-cleaving proteases is on-column cleavage of recombinant proteins. The inventors directly addressed the suitability of xlAtg4B$^{14-384}$ for this purpose using polyHis-tagged substrate proteins bound to a Silica-based Ni$^{2+}$ chelate resin of high porosity (FIG. 9). More specifically, ≈100 µM of His$_{14}$-IF2d1-xlLC3B-GFP or His$_{14}$-IF2d1-xlGATE16-GFP were immobilized on the respective matrices along with the control protein His$_{14}$-bdNEDD8-mCherry (FIG. 9A) before incubation with defined concentrations of xlAtg4B$^{14-384}$ or bdNEDP1 for 1 h at 4° C. Under these conditions, 250-500 nM of xlAtg4B$^{14-384}$ was sufficient for near-quantitative elution of GFP from the Silica-based resin (FIG. 9B, C). The cleavage was specific as even at much higher concentrations of xlAtg4B$^{14-384}$ no elution of the bdNEDD8-tagged mCherry control protein could be detected. Vice versa, after treatment with a high concentration of the bdNEDD8-specific protease bdNEDP1, only mCherry but no GFP could be detected in the eluates. When using a Sepharose-based resin with high porosity, only slightly higher protease concentrations were required for efficient elution (not shown). The elution efficiency was, however, significantly reduced when matrices with low porosity or substrate proteins without flexible linker between the polyHis tag and the protease recognition site were used (data not shown).

The xlAtg4B/xlLC3B protease/substrate pair was exploited to purify the model target protein maltose binding protein (MBP) by on-column cleavage of either His$_{14}$-IF2d1-xlLC3B-MBP or His$_{14}$-IF2d1-xlGATE16-MBP (FIG. 9 D, E). Even at moderate induction strength, both proteins were highly over-expressed in *E. coli* and displayed excellent solubility (FIG. 9E). Stronger induction led to massive over-expression of fusion proteins without compromising their solubility (not shown). About 160-200 µM of each fusion protein was immobilized on a Ni$^{2+}$ chelate resin and treated in batch with 500 nM xlAtg4B$^{14-384}$ at 4° C. Strikingly, the initial cleavage rate was very high when using the xlGATE16 fusion protein (FIG. 9D). Here, >80% and >90% of the MBP target protein was released already after 15 min and 30 min, respectively. At the corresponding time points, the xlLC3B fusion protein was processed to only P-50% and 75%. In both cases, however, efficient release of highly pure MBP was reached within one hour (FIGS. 9D and E).

An important parameter for the practical application of tag-cleaving proteases is their substrate specificity. This parameter is especially important when mutually exclusive specificity ("orthogonality") to other proteases is strictly required, e.g. for purification of protein complexes with controlled subunit stoichiometry (Frey, S. and Görlich, D. (2014) *J Chromatogr A* 1337, 106-115). Also, it is important to know which host proteases could potentially cleave a given protease recognition site during expression. For practical applications, the inventors were especially interested in the cross-reactivity of xlAtg4B with the well-established TEV protease (Kapust, R. B., et al. (2001) *Protein Engineering* 14(12), 993-1000; van den Berg, S., et al. (2006) *Journal of Biotechnology* 121, 291-298), scUlp1 (Malakhov, M. P., et al. (2004) *J Struct Funct Genomics* 5, 75-86), SUMOstar protease (Liu, L., et al. (2008) *Protein Expr Purif* 62, 21-28; Peroutka, R. J., et al. (2008) *Protein Sci* 17, 1586-1595) and the recently described proteases bdSENP1, bdNEDP1, and xlUsp2 (Frey, S. and Görlich, D. (2014) *J Chromatogr A* 1337, 95-105; Frey, S. and Görlich, D. (2014) *J Chromatogr A* 1337, 106-115). In addition, the wheat (*Triticum*) Atg4 ortholog (trAtg4) was also included. To analyze the specificity profiles of these proteases, a high concentration (20 µM) of each protease was incubated with 100 µM of each substrate protein (see FIG. 10A) for 3 h at 25° C. in all possible binary combinations (FIG. 10B). For all proteases but TEV protease, these conditions correspond to a significant (>200- to 30 000-fold) over-digestion. Under these conditions, both xlAtg4B$^{14-384}$ and trAtg4 only cleaved substrates containing Atg8-like UBLs (xlLC3B, xlGATE16 or trAtg8), but none of the substrates dedicated to other proteases. Vice versa, substrates containing Atg8-like UBLs were exclusively cleaved by Atg4 proteases. Atg4 proteases and Atg8-type substrate proteins are therefore truly orthogonal to all other protease/substrate pairs analyzed. Within the Atg8-type substrates, interesting differences became apparent: While xlLC3B was nearly exclusively recognized by xlAtg4B$^{14-384}$, both xlGATE16 and trAtg8-containing substrates were in addition also cleaved by trAtg4.

These inter- and intra-species substrate preferences of Atg4-like enzymes were analyzed further using detailed protease titration assays (FIG. 10C). Here, the *S. cerevisiae* Atg4 ortholog (scAtg4) was also included along with its cognate substrate scAtg8 that have been described recently (Frey, S. and Görlich, D. (2014) *J Chromatogr A* 1337, 95-105). In this assay, xlAtg4B showed the broadest substrate promiscuity and cleaved a 1000-fold excess of all four substrate proteins (containing xlLC3B, xlGATE16, trAtg8 or scAtg8) within 1 h at 25° C. irrespective of their origin (FIG. 10C, left column). The yeast scAtg4 protease could efficiently process xlGATE16, trAtg8 and scAtg8, but was completely unable to cleave the xlLC3B substrate (FIG. 10C, middle column). The *Triticum* protease trAtg4 cleaved only its cognate substrate trAtg8 and the yeast substrate with decent efficiency (FIG. 10C, right column). In comparison, the *Xenopus* xlGATE16 substrate required drastically (>100-fold) higher trAtg4 concentrations for significant cleavage; xlLC3B cleavage by trAtg4 was only barely detectable.

The best performing xlAtg4B fragment, xlAtg4B$^{14-384}$, has great potential as a new tag-cleaving protease. This protease fragment is highly active and routinely cleaves a 100- to 200-fold substrate excess within 1 h at 0° C. For comparison, TEV protease, which is probably still the most common tag-cleaving protease, requires 30- to 50-fold higher protease concentrations under these conditions (Frey, S. and Görlich, D. (2014) *J Chromatogr A* 1337, 95-105). In addition, xlAtg4B$^{14-384}$ is highly temperature stable (≥42° C. for 16 h) and can therefore also be used at higher temperatures. At 25° C., e.g., xlAtg4B$^{14-384}$ can cleave a 2 000-fold substrate excess within one hour; at 37° C. even less protease is required for efficient cleavage. When used for in-vitro tag removal from recombinant proteins, this high specific activity reduces contamination of the final protein preparation by the protease. Compared to other tag-cleaving proteases like yeast Ulp1p (Malakhov, M. P., Mattern, M. R., Malakhova, O. A., Drinker, M., Weeks, S. D. and Butt, T. R. (2004) *J Struct Funct Genomics* 5, 75-86; Frey, S. and Görlich, D. (2014) *J Chromatogr A* 1337, 95-105) or SUMOstar protease (Liu, L., Spurrier, J., Butt, T. R. and Strickler, J. E. (2008) *Protein Expr Purif* 62, 21-28), xlAtg4B displays a superior salt tolerance (tested up to 1.5 M NaCl) and a broad P$_1$' promiscuity, parameters that are important for robust cleavage of recombinant substrate proteins in various buffer conditions and sequence contexts.

When analyzing cross-reactivity with other tag-cleaving proteases, the inventors found out that xlAtg4B displays orthogonal specificity to the recently introduced bdSENP1 and bdNEDP1 proteases (Frey, S. and Görlich, D. (2014) *J Chromatogr A* 1337, 95-105). Together, these highly efficient proteases thus ideally complement each other and can be combined to purify protein complexes with controlled subunit stoichiometry by successive affinity capture and proteolytic release steps (Frey, S. and Görlich, D. (2014) *J Chromatogr A* 1337, 106-115).

Example 4

Application of the xlAtg4B Protease System for Purification of Proteins from Eukaryotic Hosts The unexpectedly high resistance of xlLC3B towards cleavage by Atg4-like proteases originating from other species encouraged to address the stability of xlLC3B- and xlGATE16 fusions in various eukaryotic cell extracts (FIG. 11A, B). As controls, analogous fusions to trAtg8, scSUMO and the cleavage-resistant scSUMO variant SUMOstar (Liu, L., Spurrier, J., Butt, T. R. and Strickler, J. E. (2008) *Protein Expr Purif* 62, 21-28; Peroutka, R. J., Elshourbagy, N., Piech, T. and Butt, T. R. (2008) *Protein Sci* 17, 1586-1595) were also included. Indeed, in wheat germ extract 1 µM of xlLC3B and xlGATE16 substrates were not significantly processed within 2 h at 25° C., while the corresponding trAtg8 fusion was completely cleaved. In comparison, all substrate proteins harboring Atg8 homologs were completely cleaved both in *Xenopus* egg extract and rabbit reticulocyte lysate. Interestingly, the scSUMO fusion was only partially cleaved in wheat germ extract and remained stable in rabbit reticulocyte lysate. Control incubations containing a protease mix (1 µM each of scUlp1, SUMOstar protease, xlAtg4B$^{14-384}$ and trAtg4) confirmed that the extracts did not contain any substances inhibiting specific proteolytic substrate processing.

Next, it was desired to find out if some of the analyzed ubiquitin-like protease recognition sites would also be compatible with production of intact full-length recombinant fusion proteins in a living eukaryotic host. Therefore different ZZ-UBL-Citrine substrate proteins (FIG. 11C) were over-expressed in *S. cerevisiae* under the control of the GAL1 promoter. In line with the in-vitro cleavage experiments presented before (FIG. 10C) even after 5 h induction the xlLC3B substrate was completely intact. In contrast, the scSUMO-, xlGATE16-, trAtg8- and bdSUMO-fusions were largely cleaved by endogenous yeast proteases. Surprisingly, also the "cleavage-resistant" SUMOstar variant (Liu, L., Spurrier, J., Butt, T. R. and Strickler, J. E. (2008) *Protein Expr Purif* 62, 21-28; Peroutka, R. J., Elshourbagy, N., Piech, T. and Butt, T. R. (2008) *Protein Sci* 17, 1586-1595) was not completely inert in vivo as both, N-terminal and C-terminal cleavage products could be detected with specific antibodies (FIG. 11D). Unexpectedly it was found that a fusion protein containing bdNEDD8 was even more resistant towards in vivo cleavage than the SUMOstar substrate. These findings suggest that xlLC3B and the previously introduced bdNEDD8 (Frey, S. and GOrlich, D. (2014) *J Chromatogr A* 1337, 95-105) could potentially be used as protease recognition sites for the recombinant expression of intact full-length fusion proteins in *S. cerevisiae*.

To show that the xlLC3B/xlAtg4B and bdNEDD8/bdNEDP1 systems are indeed suited for purification of recombinant proteins from a eukaryotic host, recombinant Citrine was purified as a model target protein from *S. cerevisiae*. To this end, the ZZ-UBL-Citrine fusions were over-expressed in yeast for 5 h as before. After cell lysis in a native buffer, the full-length fusion protein was found in the soluble fraction from which highly pure recombinant Citrine could be obtained by an efficient one-step capture and on-column cleavage procedure (FIG. 12).

Discussion

Importantly, both analyzed xlAtg4B substrates, xlLC3B and xlGATE16, promote solubility and high-level expression of the respective fusion proteins in *E. coli* (see FIG. 2 and FIG. 9E). This is in striking contrast to their yeast homolog scAtg8, which in direct comparison consistently produces significantly lower levels of soluble fusion proteins (FIG. 2). All in all, both xlAtg4B substrates are thus promising fusion partners for expression of recombinant target proteins in *E. coli* and may at the same time serve as recognition sites for xlAtg4B. The right choice between the two possible protease recognition sites might depend on the specific application. While xlGATE16 is cleaved more efficiently under standard conditions, xlLC3B cleavage is slightly slower but extraordinary robust.

In addition, xlLC3B features additional remarkable advantages: It was found that xlLC3B fusions are stable in wheat germ extract and even under drastic conditions only marginally processed by wheat Atg4 (trAtg4) in vitro, suggesting that stable xlLC3B fusion proteins can be produced in plants. Even more, xlLC3B is not recognized by the *S. cerevisiae* Atg4 protease. Full-length xlLC3B fusions can thus be expressed in this eukaryotic host and purified by a simple one-step capture and proteolytic release strategy. Such eukaryotic expression might be exploited for the production of proteins that rely on the eukaryotic folding machinery or have to be modified by posttranslational modifications. Fully unexpectedly, it was found that also bdNEDD8 fusion proteins are only marginally processed in yeast. With xlLC3B, bdNEDD8 (Frey, S. and Görlich, D. (2014) *J Chromatogr A* 1337, 95-105) and SUMOstar (Liu, L., Spurrier, J., Butt, T. R. and Strickler, J. E. (2008) *Protein Expr Purif* 62, 21-28; Peroutka, R. J., Elshourbagy, N., Piech, T. and Butt, T. R. (2008) *Protein Sci* 17, 1586-1595), there are now three orthogonal UBL-derived protease recognition sites that in principle allow for full-length protein production in *S. cerevisiae* (FIG. 11E and FIG. 12). Strikingly, amongst these UBLs xlLC3B is the only one that is strictly stable in vivo while traces of cleavage products originating from the bdNEDD8 substrate and low amounts of cleaved SUMOstar were clearly detected (FIG. 11D and FIG. 12B). In combination, these UBLs should allow for the in-vivo co-expression and purification of three-subunit complexes with defined subunit stoichiometry also in yeast (Frey, S. and GOrlich, D. (2014) *J Chromatogr A* 1337, 106-115).

LIST OF REFERENCES

WO 2015/049230
WO 2008/083271 A2
WO 2002/090495 A2
WO 2003/057174 A2
WO 2005/003313 A2
WO 2006/073976 A2
Hemelaar, J., Lelyveld, V. S., Kessler, B. M. and Ploegh, H. L. (2003) *J Biol Chem* 278, 51841-51850
Kabeya, Y., Mizushima, N., Yamamoto, A., Oshitani-Okamoto, S., Ohsumi, Y. and Yoshimori, T. (2004) *J Cell Sci* 117, 2805-2812
Marino, G., Uria, J. A., Puente, X. S., Quesada, V., Bordallo, J. and Lopez-Otin, C. (2003) *J Biol Chem* 278, 3671-3678
Tanida, I., Sou, Y. S., Ezaki, J., Minematsu-Ikeguchi, N., Ueno, T. and Kominami, E. (2004) *J Biol Chem* 279, 36268-36276
Li, M., Hou, Y., Wang, J., Chen, X., Shao, Z. M. and Yin, X. M. (2011) *J Biol Chem* 286, 7327-7338
Woo, J., Park, E. and Dinesh-Kumar, S. P. (2014) *Proc Natl Acad Sci USA* 111, 863-868
Kumanomidou, T., Mizushima, T., Komatsu, M., Suzuki, A., Tanida, I., Sou, Y. S., Ueno, T., Kominami, E., Tanaka, K. and Yamane, T. (2006) *J Mol Biol* 355, 612-618
Sugawara, K., Suzuki, N. N., Fujioka, Y., Mizushima, N., Ohsumi, Y. and Inagaki, F. (2005) *J Biol Chem* 280, 40058-40065
Satoo, K., Noda, N. N., Kumeta, H., Fujioka, Y., Mizushima, N., Ohsumi, Y. and Inagaki, F. (2009) *EMBO J* 28, 1341-1350
van der Veen, A. G. and Ploegh, H. L. (2012) *Annu Rev Biochem* 81, 323-357
Yeh, E. T., Gong, L. and Kamitani, T. (2000) *Gene* 248, 1-14
Malakhov, M. P., Mattern, M. R., Malakhova, O. A., Drinker, M., Weeks, S. D. and Butt, T. R. (2004) *J Struct Funct Genomics* 5, 75-86
Frey, S. and Görlich, D. (2014) *J Chromatogr A* 1337, 95-105
Frey, S. and Görlich, D. (2014) *J Chromatogr A* 1337, 106-115
Liu, L., Spurrier, J., Butt, T. R. and Strickler, J. E. (2008) *Protein Expr Purif* 62, 21-28
Peroutka, R. J., Elshourbagy, N., Piech, T. and Butt, T. R. (2008) *Protein Sci* 17, 1586-1595
Taxis, C. and Knop, M. (2012) *Methods Mol Biol* 832, 611-626
Urabe, M., Kume, A., Takahashi, T., Serizawa, N., Tobita, K. and Ozawa, K. (1999) *Biochem Biophys Res Commun* 266, 92-96
Taxis, C., Stier, G., Spadaccini, R. and Knop, M. (2009) *Mol Syst Biol* 5, 267
Griesbeck, O., Baird, G. S., Campbell, R. E., Zacharias, D. A. and Tsien, R. Y. (2001) *J Biol Chem* 276, 29188-29194
Heikal, A. A., Hess, S. T., Baird, G. S., Tsien, R. Y. and Webb, W. W. (2000) *Proc Natl Acad Sci USA* 97, 11996-12001
Riezman, H., Hase, T., van Loon, A. P., Grivell, L. A., Suda, K. and Schatz, G. (1983) *EMBO J* 2, 2161-2168
Conzelmann, A., Riezman, H., Desponds, C. and Bron, C. (1988) *EMBO J* 7, 2233-2240
Butt, T. R., Edavettal, S. C., Hall, J. P. and Mattern, M. R. (2005) *Protein Expr Purif* 43, 1-9
Arnau, J., Lauritzen, C., Petersen, G. E. and Pedersen, J. (2006) *Protein Expr Purif* 48, 1-13
Li, S. J. and Hochstrasser, M. (1999) *Nature* 398, 246-251
Nilsson, J., Stahl, S., Lundeberg, J., Uhlen, M. and Nygren, P. A. (1997) *Protein Expr Purif* 11, 1-16
Young, C. L., Britton, Z. T. and Robinson, A. S. (2012) *Biotechnol J* 7, 620-634
Renicke, C., Spadaccini, R. and Taxis, C. (2013) *PLoS One* 8, e67915 UniProt Q640G7
Kapust, R. B., Tozser, J., Fox, J. D., Anderson, D. E. (2001) *Protein Engineering* 14(12), 993-1000
van den Berg, S., Lofdahl, P. A., Hard, T., Berglund, H. (2006) *Journal of Biotechnology* 121, 291-298.
Cathrin Enke, Doktorarbeit 2010, Cuvillier Verlag Göttingen, ISBN 978-3-86955-483-9
Blow, J. J., Laskey, R. A. (1986) *Cell* 47, 577-587.

The invention claimed is:

1. A protease comprising an amino acid sequence with at least 97% identity over amino acids 14 384 of SEQ ID NO: 1 (xlAtg4B), with the proviso that the protease is not the protease of SEQ ID NO: 1,
wherein said protease is capable of cleaving the protease recognition site (PRS) according to SEQ ID NO: 2 (xlLC3B) with at least 20% activity as compared to the parent protease with the amino acid sequence of SEQ ID NO: 1, if tested using a native substrate protein shown in SEQ ID NO: 3 (His$_{14}$-xlLC3B-MBP) and 500 nM of said protease at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT and/or
wherein said protease is capable of cleaving the protease recognition site (PRS) according to SEQ ID NO: 4 (xlGATE16) with at least 20% activity as compared to the parent protease with the amino acid sequence of SEQ ID NO: 1, if tested using 500 nM of said protease and a native substrate protein shown in SEQ ID NO: 5 (His$_{14}$-xlGATE16-MBP) at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

2. The protease of claim 1, wherein the protease comprises the amino acid sequence of amino acids 14-384 of SEQ ID NO: 1 (xlAtg4B).

3. The protease of claim 1, wherein the protease is capable of cleaving
(i) at least 90% of a 100-fold, preferably 150-fold, more preferably 200-fold molar excess of a native substrate protein shown in SEQ ID NO: 3 (His$_{14}$-xlLC3B-MBP); and/or
(ii) at least 90% of a 150-fold, preferably 200-fold, more preferably 300-fold molar excess of a native substrate protein shown in SEQ ID NO: 5 (His$_{14}$-xlGATE16-MBP);
at standard conditions of 1 hour incubation at 0° C., 100 µM initial concentration of substrate protein in a buffer consisting of 250 mM NaCl, 40 mM Tris/HCl pH 7.5, 2 mM MgCl$_2$, 250 mM sucrose, 2 mM DTT.

4. The protease of claim 1, wherein the protease is capable of cleaving
(i) at least 90% of a 500-fold, preferably 1000-fold, more preferably 1500-fold, most preferably 2000-fold molar excess of a native substrate protein shown in SEQ ID NO: 3 (His$_{14}$-xlLC3B-MBP); and/or
(ii) at least 90% of a 2000-fold, preferably 3000-fold, more preferably 4000-fold, even more preferably 5000-fold, still more preferably 6000-fold, most preferably 6600-fold molar excess of a native substrate protein shown in SEQ ID NO: 5 (His$_{14}$-xlGATE16-MBP);

at conditions of 1 hour incubation at 25° C., 100 μM initial concentration of substrate protein in a buffer consisting of 250 mM NaCl, 40 mM Tris/HCl pH 7.5, 2 mM $MgCl_2$, 250 mM sucrose, 2 mM DTT.

5. The protease of claim 1, wherein the protease is capable of cleaving at least 90% of a 100-fold molar excess of native substrate protein variants in which only residue 152 in SEQ ID NO: 3 (the $P_1'$ position of $His_{14}$-xlLC3B-MBP) has been mutated to Met, Tyr, Arg or Glu relative to SEQ ID NO: 3 at standard conditions of 1 hour incubation at 0° C., 100 μM initial concentration of substrate protein in a buffer consisting of 250 mM NaCl, 40 mM Tris/HCl pH 7.5, 2 mM $MgCl_2$, 250 mM sucrose, 2 mM DTT.

6. The protease of claim 1, wherein the protease is capable of cleaving at least 50% of a 200-fold molar excess of a native substrate protein as shown in SEQ ID NO: 3 ($His_{14}$-xlLC3B-MBP) within one hour at 0° C. at high-salt conditions of 100 μM initial concentration of substrate protein in a buffer consisting of 1.5 M NaCl, 40 mM Tris/HCl pH 7.5, 2 mM $MgCl_2$, 250 mM sucrose, 2 mM DTT.

7. The protease of claim 1, wherein the protease cleaves at stringent conditions any of the substrates shown in SEQ ID NO: 6 ($His_{10}$-ZZ-TEV-MBP), SEQ ID NO: 7 ($His_{14}$-bdNEDD8-MBP), SEQ ID NO: 8 ($His_{14}$-bdSUMO-MBP), SEQ ID NO: 9 ($His_{14}$-xlUb-MBP), or SEQ ID NO: 22 ($His_{14}$-SUMOstar-MBP) at least 10 000 fold less efficiently than the substrate shown in SEQ ID NO: 3 ($His_{14}$-xlLC3B-MBP), wherein stringent conditions are defined as 3 hour incubation at 25° C., 20 μM protease, 100 μM initial concentration of substrate protein in a buffer consisting of 250 mM NaCl, 40 mM Tris/HCl pH 7.5, 2 mM $MgCl_2$, 250 mM sucrose, 2 mM DTT.

8. The protease of claim 1, wherein the protease, if the protease does not comprise a polyHis-tag, is capable of cleaving a substrate protein as shown in SEQ ID NO: 25 ($His_{14}$-IF2d1-xlLC3B-MBP) immobilized on a Ni(II) chelate resin with at least 10% efficiency as compared to the non-immobilised substrate at standard conditions of 1 hour incubation at 0° C., 100 μM initial concentration of substrate protein in a buffer consisting of 250 mM NaCl, 40 mM Tris/HCl pH 7.5, 2 mM $MgCl_2$, 250 mM sucrose, 2 mM DTT.

9. The protease of claim 1, wherein the protease retains at least 50% of its activity when pre-incubated for 16 h at 42° C. in the absence of oxygen in a buffer consisting of 250 mM NaCl, 40 mM Tris/HCl pH 7.5, 2 mM $MgCl_2$, 250 mM sucrose, 20 mM DTT, as compared to said non-treated protease, if tested using a native substrate protein shown in SEQ ID NO: 3 ($His_{14}$-xlLC3B-MBP) and 500 nM of said protease at standard conditions of 1 hour incubation at 0° C., 100 μM initial concentration of substrate protein in a buffer consisting of 250 mM NaCl, 40 mM Tris/HCl pH 7.5, 2 mM $MgCl_2$, 250 mM sucrose, 2 mM DTT.

10. The protease of claim 1, wherein the protease further comprises a poly-His tag, a MBP-tag or a ZZ-tag.

11. The protease of claim 1, wherein the protease further comprises an affinity tag.

12. A protease consisting of the amino acid sequence of amino acids 14-384 of SEQ ID NO: 1 (xlAtg4B).

13. A method of removing a protein tag, which comprises contacting said protein tag the protease according to claim 1.

14. The method of claim 13, wherein the protease is used for on-column cleavage in an affinity chromatographic purification step.

* * * * *

SEQUENCE LISTING

```
<160> NUMBER OF SEQ ID NOS: 25

<210> SEQ ID NO 1
<211> LENGTH: 384
<212> TYPE: PRT
<213> ORGANISM: Xenopus laevis

<400> SEQUENCE: 1

Met Asp Ala Ala Thr Leu Thr Tyr Asp Thr Leu Arg Phe Ala Asp Thr
1               5                   10                  15

Pro Asp Phe Pro Glu Thr Ala Glu Pro Val Trp Val Leu Gly Arg Lys
            20                  25                  30
```

```
Tyr Ser Ala Leu Thr Glu Lys Glu Gln Leu Leu Asn Asp Ile Thr Ser
            35                  40                  45

Arg Leu Trp Phe Thr Tyr Arg Arg Asn Phe Gln Ala Ile Gly Gly Thr
 50                  55                  60

Gly Pro Thr Ser Asp Thr Gly Trp Gly Cys Met Leu Arg Cys Gly Gln
 65                  70                  75                  80

Met Ile Phe Ala Gln Ala Leu Ile Cys Arg His Val Gly Arg Asp Trp
                 85                  90                  95

Arg Trp Asp Lys Gln Lys Pro Lys Gly Glu Tyr Leu Asn Ile Leu Thr
            100                 105                 110

Ala Phe Leu Asp Lys Lys Asp Ser Tyr Tyr Ser Ile His Gln Ile Ala
        115                 120                 125

Gln Met Gly Val Gly Glu Gly Lys Tyr Ile Gly Gln Trp Tyr Gly Pro
    130                 135                 140

Asn Thr Val Ala Gln Val Leu Arg Lys Leu Ala Val Phe Asp Gln Trp
145                 150                 155                 160

Ser Ser Ile Ala Val His Ile Ala Met Asp Asn Thr Val Val Val Asp
                165                 170                 175

Glu Ile Arg Arg Leu Cys Arg Ala Gly Ser Gly Glu Ser Ser Asp Ala
            180                 185                 190

Gly Ala Leu Ser Asn Gly Tyr Thr Gly Asp Ser Asp Pro Ser Cys Ala
        195                 200                 205

Gln Trp Lys Pro Leu Val Leu Leu Ile Pro Leu Arg Leu Gly Leu Ser
    210                 215                 220

Glu Ile Asn Glu Ala Tyr Ile Glu Thr Leu Lys His Cys Phe Met Val
225                 230                 235                 240

Pro Gln Ser Leu Gly Val Ile Gly Gly Arg Pro Asn Ser Ala His Tyr
                245                 250                 255

Phe Ile Gly Tyr Val Gly Asp Glu Leu Ile Tyr Leu Asp Pro His Thr
            260                 265                 270

Thr Gln Leu Ser Val Glu Pro Ser Asp Cys Ser Phe Ile Glu Asp Glu
        275                 280                 285

Ser Phe His Cys Gln His Pro Pro Cys Arg Met His Val Ser Glu Ile
    290                 295                 300

Asp Pro Ser Ile Ala Val Gly Phe Phe Cys Ser Ser Gln Glu Asp Phe
305                 310                 315                 320

Glu Asp Trp Cys Gln His Ile Lys Lys Leu Ser Leu Ser Gly Gly Ala
                325                 330                 335

Leu Pro Met Phe Glu Val Val Asp Gln Leu Pro Leu His Leu Ser Asn
            340                 345                 350

Pro Asp Val Leu Asn Leu Thr Pro Asp Ser Ser Asp Ala Asp Arg Leu
        355                 360                 365

Asp Arg Phe Phe Asp Ser Glu Asp Glu Glu Phe Glu Ile Leu Ser Leu
    370                 375                 380

<210> SEQ ID NO 2
<211> LENGTH: 120
<212> TYPE: PRT
<213> ORGANISM: Xenopus laevis

<400> SEQUENCE: 2

Met Pro Ser Glu Lys Thr Phe Lys Gln Arg Arg Ser Leu Glu Gln Arg
1               5                   10                  15

Val Glu Asp Val Arg Leu Ile Arg Glu Gln His Pro Thr Lys Ile Pro
            20                  25                  30
```

```
Val Ile Ile Glu Arg Tyr Lys Gly Glu Lys Gln Leu Pro Val Leu Asp
             35                  40                  45

Lys Thr Lys Phe Leu Val Pro Asp His Val Asn Met Ser Glu Leu Ile
 50                  55                  60

Lys Ile Ile Arg Arg Arg Leu Gln Leu Asn Ser Asn Gln Ala Phe Phe
 65                  70                  75                  80

Leu Leu Val Asn Gly His Ser Met Val Ser Val Ser Thr Pro Ile Ser
                 85                  90                  95

Glu Val Tyr Glu Arg Glu Lys Asp Glu Asp Gly Phe Leu Tyr Met Val
             100                 105                 110

Tyr Ala Ser Gln Glu Thr Phe Gly
             115                 120

<210> SEQ ID NO 3
<211> LENGTH: 525
<212> TYPE: PRT
<213> ORGANISM: Artificial
<220> FEATURE:
<223> OTHER INFORMATION: His14-xlLC3B-MBP

<400> SEQUENCE: 3

Met Ser Lys His His His His Ser Gly His His Thr Gly His His
 1               5                  10                  15

His His Ser Gly Ser His His Thr Gly Gly Ser Ser Gly Ser Glu
                 20                  25                  30

Ser Ser Glu Lys Thr Phe Lys Gln Arg Arg Ser Leu Glu Gln Arg Val
             35                  40                  45

Glu Asp Val Arg Leu Ile Arg Glu Gln His Pro Thr Lys Ile Pro Val
 50                  55                  60

Ile Ile Glu Arg Tyr Lys Gly Glu Lys Gln Leu Pro Val Leu Asp Lys
 65                  70                  75                  80

Thr Lys Phe Leu Val Pro Asp His Val Asn Met Ser Glu Leu Ile Lys
                 85                  90                  95

Ile Ile Arg Arg Arg Leu Gln Leu Asn Ser Asn Gln Ala Phe Phe Leu
             100                 105                 110

Leu Val Asn Gly His Ser Met Val Ser Val Ser Thr Pro Ile Ser Glu
         115                 120                 125

Val Tyr Glu Arg Glu Lys Asp Glu Asp Gly Phe Leu Tyr Met Val Tyr
     130                 135                 140

Ala Ser Gln Glu Thr Phe Gly Ala Gly Thr Lys Thr Glu Glu Gly Lys
145                 150                 155                 160

Leu Val Ile Trp Ile Asn Gly Asp Lys Gly Tyr Asn Gly Leu Ala Glu
                165                 170                 175

Val Gly Lys Lys Phe Glu Lys Asp Thr Gly Ile Lys Val Thr Val Glu
            180                 185                 190

His Pro Asp Lys Leu Glu Glu Lys Phe Pro Gln Val Ala Ala Thr Gly
        195                 200                 205

Asp Gly Pro Asp Ile Ile Phe Trp Ala His Asp Arg Phe Gly Gly Tyr
    210                 215                 220

Ala Gln Ser Gly Leu Leu Ala Glu Ile Thr Pro Asp Lys Ala Phe Gln
225                 230                 235                 240

Asp Lys Leu Tyr Pro Phe Thr Trp Asp Ala Val Arg Tyr Asn Gly Lys
                245                 250                 255

Leu Ile Ala Tyr Pro Ile Ala Val Glu Ala Leu Ser Leu Ile Tyr Asn
            260                 265                 270
```

```
Lys Asp Leu Leu Pro Asn Pro Pro Lys Thr Trp Glu Ile Pro Ala
            275                 280                 285

Leu Asp Lys Glu Leu Lys Ala Lys Gly Lys Ser Ala Leu Met Phe Asn
290                 295                 300

Leu Gln Glu Pro Tyr Phe Thr Trp Pro Leu Ile Ala Ala Asp Gly Gly
305                 310                 315                 320

Tyr Ala Phe Lys Tyr Glu Asn Gly Lys Tyr Asp Ile Lys Asp Val Gly
                325                 330                 335

Val Asp Asn Ala Gly Ala Lys Ala Gly Leu Thr Phe Leu Val Asp Leu
            340                 345                 350

Ile Lys Asn Lys His Met Asn Ala Asp Thr Asp Tyr Ser Ile Ala Glu
        355                 360                 365

Ala Ala Phe Asn Lys Gly Glu Thr Ala Met Thr Ile Asn Gly Pro Trp
370                 375                 380

Ala Trp Ser Asn Ile Asp Thr Ser Lys Val Asn Tyr Gly Val Thr Val
385                 390                 395                 400

Leu Pro Thr Phe Lys Gly Gln Pro Ser Lys Pro Phe Val Gly Val Leu
                405                 410                 415

Ser Ala Gly Ile Asn Ala Ala Ser Pro Asn Lys Glu Leu Ala Lys Glu
            420                 425                 430

Phe Leu Glu Asn Tyr Leu Leu Thr Asp Glu Gly Leu Glu Ala Val Asn
        435                 440                 445

Lys Asp Lys Pro Leu Gly Ala Val Ala Leu Lys Ser Tyr Glu Glu Glu
450                 455                 460

Leu Ala Lys Asp Pro Arg Ile Ala Ala Thr Met Glu Asn Ala Gln Lys
465                 470                 475                 480

Gly Glu Ile Met Pro Asn Ile Pro Gln Met Ser Ala Phe Trp Tyr Ala
                485                 490                 495

Val Arg Thr Ala Val Ile Asn Ala Ala Ser Gly Arg Gln Thr Val Asp
            500                 505                 510

Glu Ala Leu Lys Asp Ala Gln Thr Asn Gly Thr Gly Cys
        515                 520                 525

<210> SEQ ID NO 4
<211> LENGTH: 116
<212> TYPE: PRT
<213> ORGANISM: Xenopus laevis

<400> SEQUENCE: 4

Met Lys Trp Met Phe Lys Glu Asp His Ser Leu Glu His Arg Cys Val
1               5                   10                  15

Glu Ser Ala Lys Ile Arg Ala Lys Tyr Pro Asp Arg Val Pro Val Ile
            20                  25                  30

Val Glu Lys Val Ser Gly Ser Gln Ile Val Asp Ile Asp Lys Arg Lys
        35                  40                  45

Tyr Leu Val Pro Ser Asp Ile Thr Val Ala Gln Phe Met Trp Ile Ile
    50                  55                  60

Arg Lys Arg Ile Gln Leu Pro Ser Glu Lys Ala Ile Phe Leu Phe Val
65                  70                  75                  80

Asp Lys Thr Val Pro Gln Ser Ser Leu Thr Met Gly Gln Leu Tyr Glu
                85                  90                  95

Lys Glu Lys Asp Glu Asp Gly Phe Leu Tyr Val Ala Tyr Ser Gly Glu
            100                 105                 110

Asn Thr Phe Gly
```

-continued

115

<210> SEQ ID NO 5
<211> LENGTH: 524
<212> TYPE: PRT
<213> ORGANISM: Artificial
<220> FEATURE:
<223> OTHER INFORMATION: His14-xlGATE16-MBP

<400> SEQUENCE: 5

Met Ser Lys His His His His Ser Gly His His Thr Gly His His
1               5                   10                  15

His His Ser Gly Ser His His Thr Gly Gly Ser Ser Gly Ser Glu
            20                  25                  30

Ser Ser Met Lys Trp Met Phe Lys Glu Asp His Ser Leu Glu His Arg
        35                  40                  45

Cys Val Glu Ser Ala Lys Ile Arg Ala Lys Tyr Pro Asp Arg Val Pro
    50                  55                  60

Val Ile Val Glu Lys Val Ser Gly Ser Gln Ile Val Asp Ile Asp Lys
65                  70                  75                  80

Arg Lys Tyr Leu Val Pro Ser Asp Ile Thr Val Ala Gln Phe Met Trp
                85                  90                  95

Ile Ile Arg Lys Arg Ile Gln Leu Pro Ser Glu Lys Ala Ile Phe Leu
            100                 105                 110

Phe Val Asp Lys Thr Val Pro Gln Ser Ser Leu Thr Met Gly Gln Leu
        115                 120                 125

Tyr Glu Lys Glu Lys Asp Glu Asp Gly Phe Leu Tyr Val Ala Tyr Ser
    130                 135                 140

Gly Glu Asn Thr Phe Gly Ala Gly Thr Lys Thr Glu Glu Gly Lys Leu
145                 150                 155                 160

Val Ile Trp Ile Asn Gly Asp Lys Gly Tyr Asn Gly Leu Ala Glu Val
                165                 170                 175

Gly Lys Lys Phe Glu Lys Asp Thr Gly Ile Lys Val Thr Val Glu His
            180                 185                 190

Pro Asp Lys Leu Glu Glu Lys Phe Pro Gln Val Ala Ala Thr Gly Asp
        195                 200                 205

Gly Pro Asp Ile Ile Phe Trp Ala His Asp Arg Phe Gly Gly Tyr Ala
    210                 215                 220

Gln Ser Gly Leu Leu Ala Glu Ile Thr Pro Asp Lys Ala Phe Gln Asp
225                 230                 235                 240

Lys Leu Tyr Pro Phe Thr Trp Asp Ala Val Arg Tyr Asn Gly Lys Leu
                245                 250                 255

Ile Ala Tyr Pro Ile Ala Val Glu Ala Leu Ser Leu Ile Tyr Asn Lys
            260                 265                 270

Asp Leu Leu Pro Asn Pro Pro Lys Thr Trp Glu Glu Ile Pro Ala Leu
        275                 280                 285

Asp Lys Glu Leu Lys Ala Lys Gly Lys Ser Ala Leu Met Phe Asn Leu
    290                 295                 300

Gln Glu Pro Tyr Phe Thr Trp Pro Leu Ile Ala Ala Asp Gly Gly Tyr
305                 310                 315                 320

Ala Phe Lys Tyr Glu Asn Gly Lys Tyr Asp Ile Lys Asp Val Gly Val
                325                 330                 335

Asp Asn Ala Gly Ala Lys Ala Gly Leu Thr Phe Leu Val Asp Leu Ile
            340                 345                 350

Lys Asn Lys His Met Asn Ala Asp Thr Asp Tyr Ser Ile Ala Glu Ala

-continued

```
                355                 360                 365
Ala Phe Asn Lys Gly Glu Thr Ala Met Thr Ile Asn Gly Pro Trp Ala
            370                 375                 380

Trp Ser Asn Ile Asp Thr Ser Lys Val Asn Tyr Gly Val Thr Val Leu
385                 390                 395                 400

Pro Thr Phe Lys Gly Gln Pro Ser Lys Pro Phe Val Gly Val Leu Ser
                405                 410                 415

Ala Gly Ile Asn Ala Ala Ser Pro Asn Lys Glu Leu Ala Lys Glu Phe
            420                 425                 430

Leu Glu Asn Tyr Leu Leu Thr Asp Glu Gly Leu Glu Ala Val Asn Lys
        435                 440                 445

Asp Lys Pro Leu Gly Ala Val Ala Leu Lys Ser Tyr Glu Glu Glu Leu
    450                 455                 460

Ala Lys Asp Pro Arg Ile Ala Ala Thr Met Glu Asn Ala Gln Lys Gly
465                 470                 475                 480

Glu Ile Met Pro Asn Ile Pro Gln Met Ser Ala Phe Trp Tyr Ala Val
                485                 490                 495

Arg Thr Ala Val Ile Asn Ala Ala Ser Gly Arg Gln Thr Val Asp Glu
            500                 505                 510

Ala Leu Lys Asp Ala Gln Thr Asn Gly Thr Gly Cys
        515                 520
```

<210> SEQ ID NO 6
<211> LENGTH: 512
<212> TYPE: PRT
<213> ORGANISM: Artificial
<220> FEATURE:
<223> OTHER INFORMATION: His10-ZZ-TEV-MBP

<400> SEQUENCE: 6

```
Met His His His His His His His His His Gly Ser Asn Lys Phe
1               5                   10                  15

Asn Lys Glu Gln Gln Asn Ala Phe Tyr Glu Ile Leu His Leu Pro Asn
            20                  25                  30

Leu Asn Glu Glu Gln Arg Asn Ala Phe Ile Gln Ser Leu Lys Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Ala Met Asn Lys Phe Asn Lys Glu Gln Gln
65                  70                  75                  80

Asn Ala Phe Tyr Glu Ile Leu His Leu Pro Asn Leu Asn Glu Glu Gln
                85                  90                  95

Arg Asn Ala Phe Ile Gln Ser Leu Lys Asp Asp Pro Ser Gln Ser Ala
            100                 105                 110

Asn Leu Leu Ala Glu Ala Lys Lys Leu Asn Asp Ala Gln Ala Pro Lys
        115                 120                 125

Val Ala Met Ser Gly Glu Asn Leu Tyr Phe Gln Gly Thr Lys Thr Glu
    130                 135                 140

Glu Gly Lys Leu Val Ile Trp Ile Asn Gly Asp Lys Gly Tyr Asn Gly
145                 150                 155                 160

Leu Ala Glu Val Gly Lys Lys Phe Glu Lys Asp Thr Gly Ile Lys Val
                165                 170                 175

Thr Val Glu His Pro Asp Lys Leu Glu Glu Lys Phe Pro Gln Val Ala
            180                 185                 190

Ala Thr Gly Asp Gly Pro Asp Ile Ile Phe Trp Ala His Asp Arg Phe
```

```
            195                 200                 205
Gly Gly Tyr Ala Gln Ser Gly Leu Leu Ala Glu Ile Thr Pro Asp Lys
    210                 215                 220

Ala Phe Gln Asp Lys Leu Tyr Pro Phe Thr Trp Asp Ala Val Arg Tyr
225                 230                 235                 240

Asn Gly Lys Leu Ile Ala Tyr Pro Ile Ala Val Glu Ala Leu Ser Leu
                245                 250                 255

Ile Tyr Asn Lys Asp Leu Leu Pro Asn Pro Pro Lys Thr Trp Glu Glu
            260                 265                 270

Ile Pro Ala Leu Asp Lys Glu Leu Lys Ala Lys Gly Lys Ser Ala Leu
        275                 280                 285

Met Phe Asn Leu Gln Glu Pro Tyr Phe Thr Trp Pro Leu Ile Ala Ala
    290                 295                 300

Asp Gly Gly Tyr Ala Phe Lys Tyr Glu Asn Gly Lys Tyr Asp Ile Lys
305                 310                 315                 320

Asp Val Gly Val Asp Asn Ala Gly Ala Lys Ala Gly Leu Thr Phe Leu
                325                 330                 335

Val Asp Leu Ile Lys Asn Lys His Met Asn Ala Asp Thr Asp Tyr Ser
            340                 345                 350

Ile Ala Glu Ala Ala Phe Asn Lys Gly Glu Thr Ala Met Thr Ile Asn
        355                 360                 365

Gly Pro Trp Ala Trp Ser Asn Ile Asp Thr Ser Lys Val Asn Tyr Gly
    370                 375                 380

Val Thr Val Leu Pro Thr Phe Lys Gly Gln Pro Ser Lys Pro Phe Val
385                 390                 395                 400

Gly Val Leu Ser Ala Gly Ile Asn Ala Ala Ser Pro Asn Lys Glu Leu
                405                 410                 415

Ala Lys Glu Phe Leu Glu Asn Tyr Leu Leu Thr Asp Glu Gly Leu Glu
            420                 425                 430

Ala Val Asn Lys Asp Lys Pro Leu Gly Ala Val Ala Leu Lys Ser Tyr
        435                 440                 445

Glu Glu Glu Leu Ala Lys Asp Pro Arg Ile Ala Ala Thr Met Glu Asn
    450                 455                 460

Ala Gln Lys Gly Glu Ile Met Pro Asn Ile Pro Gln Met Ser Ala Phe
465                 470                 475                 480

Trp Tyr Ala Val Arg Thr Ala Val Ile Asn Ala Ala Ser Gly Arg Gln
                485                 490                 495

Thr Val Asp Glu Ala Leu Lys Asp Ala Gln Thr Asn Gly Thr Gly Cys
            500                 505                 510

<210> SEQ ID NO 7
<211> LENGTH: 476
<212> TYPE: PRT
<213> ORGANISM: Artificial
<220> FEATURE:
<223> OTHER INFORMATION: His14-bdNEDD8-MBP

<400> SEQUENCE: 7

Met Ser Lys His His His His Ser Gly His His Thr Gly His His
1               5                   10                  15

His His Ser Gly Ser His His Ser Gly Thr Met Ile Lys Val Lys
                20                  25                  30

Thr Leu Thr Gly Lys Glu Ile Glu Ile Asp Ile Glu Pro Thr Asp Thr
            35                  40                  45

Ile Asp Arg Ile Lys Glu Arg Val Glu Glu Lys Glu Gly Ile Pro Pro
```

```
            50                  55                  60
Val Gln Gln Arg Leu Ile Tyr Ala Gly Lys Gln Leu Ala Asp Asp Lys
 65                  70                  75                  80

Thr Ala Lys Asp Tyr Asn Ile Glu Gly Gly Ser Val Leu His Leu Val
                 85                  90                  95

Leu Ala Leu Arg Gly Gly Ala Gly Thr Lys Thr Glu Glu Gly Lys Leu
                100                 105                 110

Val Ile Trp Ile Asn Gly Asp Lys Gly Tyr Asn Gly Leu Ala Glu Val
            115                 120                 125

Gly Lys Lys Phe Glu Lys Asp Thr Gly Ile Lys Val Thr Val Glu His
        130                 135                 140

Pro Asp Lys Leu Glu Glu Lys Phe Pro Gln Val Ala Ala Thr Gly Asp
145                 150                 155                 160

Gly Pro Asp Ile Ile Phe Trp Ala His Asp Arg Phe Gly Gly Tyr Ala
                165                 170                 175

Gln Ser Gly Leu Leu Ala Glu Ile Thr Pro Asp Lys Ala Phe Gln Asp
            180                 185                 190

Lys Leu Tyr Pro Phe Thr Trp Asp Ala Val Arg Tyr Asn Gly Lys Leu
        195                 200                 205

Ile Ala Tyr Pro Ile Ala Val Glu Ala Leu Ser Leu Ile Tyr Asn Lys
210                 215                 220

Asp Leu Leu Pro Asn Pro Pro Lys Thr Trp Glu Glu Ile Pro Ala Leu
225                 230                 235                 240

Asp Lys Glu Leu Lys Ala Lys Gly Lys Ser Ala Leu Met Phe Asn Leu
                245                 250                 255

Gln Glu Pro Tyr Phe Thr Trp Pro Leu Ile Ala Ala Asp Gly Gly Tyr
            260                 265                 270

Ala Phe Lys Tyr Glu Asn Gly Lys Tyr Asp Ile Lys Asp Val Gly Val
        275                 280                 285

Asp Asn Ala Gly Ala Lys Ala Gly Leu Thr Phe Leu Val Asp Leu Ile
290                 295                 300

Lys Asn Lys His Met Asn Ala Asp Thr Asp Tyr Ser Ile Ala Glu Ala
305                 310                 315                 320

Ala Phe Asn Lys Gly Glu Thr Ala Met Thr Ile Asn Gly Pro Trp Ala
                325                 330                 335

Trp Ser Asn Ile Asp Thr Ser Lys Val Asn Tyr Gly Val Thr Val Leu
            340                 345                 350

Pro Thr Phe Lys Gly Gln Pro Ser Lys Pro Phe Val Gly Val Leu Ser
        355                 360                 365

Ala Gly Ile Asn Ala Ala Ser Pro Asn Lys Glu Leu Ala Lys Glu Phe
370                 375                 380

Leu Glu Asn Tyr Leu Leu Thr Asp Glu Gly Leu Glu Ala Val Asn Lys
385                 390                 395                 400

Asp Lys Pro Leu Gly Ala Val Ala Leu Lys Ser Tyr Glu Glu Glu Leu
                405                 410                 415

Ala Lys Asp Pro Arg Ile Ala Ala Thr Met Glu Asn Ala Gln Lys Gly
            420                 425                 430

Glu Ile Met Pro Asn Ile Pro Gln Met Ser Ala Phe Trp Tyr Ala Val
        435                 440                 445

Arg Thr Ala Val Ile Asn Ala Ala Ser Gly Arg Gln Thr Val Asp Glu
450                 455                 460

Ala Leu Lys Asp Ala Gln Thr Asn Gly Thr Gly Cys
465                 470                 475
```

<210> SEQ ID NO 8
<211> LENGTH: 496
<212> TYPE: PRT
<213> ORGANISM: Artificial
<220> FEATURE:
<223> OTHER INFORMATION: His14-bdSUMO-MBP

<400> SEQUENCE: 8

```
Met Ser Lys His His His His Ser Gly His His Thr Gly His His
1               5                   10                  15

His His Ser Gly Ser His His Ser Gly Ser Ala Ala Gly Gly Glu
                20                  25                  30

Glu Asp Lys Lys Pro Ala Gly Gly Glu Gly Gly Gly Ala His Ile Asn
            35                  40                  45

Leu Lys Val Lys Gly Gln Asp Gly Asn Glu Val Phe Phe Arg Ile Lys
50                  55                  60

Arg Ser Thr Gln Leu Lys Lys Leu Met Asn Ala Tyr Cys Asp Arg Gln
65                  70                  75                  80

Ser Val Asp Met Thr Ala Ile Ala Phe Leu Phe Asp Gly Arg Arg Leu
                85                  90                  95

Arg Ala Glu Gln Thr Pro Asp Glu Leu Glu Met Glu Asp Gly Asp Glu
            100                 105                 110

Ile Asp Ala Met Leu His Gln Thr Gly Gly Ala Gly Thr Lys Thr Glu
            115                 120                 125

Glu Gly Lys Leu Val Ile Trp Ile Asn Gly Asp Lys Gly Tyr Asn Gly
        130                 135                 140

Leu Ala Glu Val Gly Lys Lys Phe Glu Lys Asp Thr Gly Ile Lys Val
145                 150                 155                 160

Thr Val Glu His Pro Asp Lys Leu Glu Glu Lys Phe Pro Gln Val Ala
                165                 170                 175

Ala Thr Gly Asp Gly Pro Asp Ile Ile Phe Trp Ala His Asp Arg Phe
            180                 185                 190

Gly Gly Tyr Ala Gln Ser Gly Leu Leu Ala Glu Ile Thr Pro Asp Lys
        195                 200                 205

Ala Phe Gln Asp Lys Leu Tyr Pro Phe Thr Trp Asp Ala Val Arg Tyr
    210                 215                 220

Asn Gly Lys Leu Ile Ala Tyr Pro Ile Ala Val Glu Ala Leu Ser Leu
225                 230                 235                 240

Ile Tyr Asn Lys Asp Leu Leu Pro Asn Pro Pro Lys Thr Trp Glu Glu
                245                 250                 255

Ile Pro Ala Leu Asp Lys Glu Leu Lys Ala Lys Gly Lys Ser Ala Leu
            260                 265                 270

Met Phe Asn Leu Gln Glu Pro Tyr Phe Thr Trp Pro Leu Ile Ala Ala
        275                 280                 285

Asp Gly Gly Tyr Ala Phe Lys Tyr Glu Asn Gly Lys Tyr Asp Ile Lys
    290                 295                 300

Asp Val Gly Val Asp Asn Ala Gly Ala Lys Ala Gly Leu Thr Phe Leu
305                 310                 315                 320

Val Asp Leu Ile Lys Asn Lys His Met Asn Ala Asp Thr Asp Tyr Ser
                325                 330                 335

Ile Ala Glu Ala Ala Phe Asn Lys Gly Glu Thr Ala Met Thr Ile Asn
            340                 345                 350

Gly Pro Trp Ala Trp Ser Asn Ile Asp Thr Ser Lys Val Asn Tyr Gly
        355                 360                 365
```

```
Val Thr Val Leu Pro Thr Phe Lys Gly Gln Pro Ser Lys Pro Phe Val
            370                 375                 380

Gly Val Leu Ser Ala Gly Ile Asn Ala Ala Ser Pro Asn Lys Glu Leu
385                 390                 395                 400

Ala Lys Glu Phe Leu Glu Asn Tyr Leu Leu Thr Asp Glu Gly Leu Glu
                405                 410                 415

Ala Val Asn Lys Asp Lys Pro Leu Gly Ala Val Ala Leu Lys Ser Tyr
            420                 425                 430

Glu Glu Glu Leu Ala Lys Asp Pro Arg Ile Ala Ala Thr Met Glu Asn
                435                 440                 445

Ala Gln Lys Gly Glu Ile Met Pro Asn Ile Pro Gln Met Ser Ala Phe
            450                 455                 460

Trp Tyr Ala Val Arg Thr Ala Val Ile Asn Ala Ala Ser Gly Arg Gln
465                 470                 475                 480

Thr Val Asp Glu Ala Leu Lys Asp Ala Gln Thr Asn Gly Thr Gly Cys
                485                 490                 495

<210> SEQ ID NO 9
<211> LENGTH: 484
<212> TYPE: PRT
<213> ORGANISM: Artificial
<220> FEATURE:
<223> OTHER INFORMATION: His14-xlUb-MBP

<400> SEQUENCE: 9

Met Ser Lys His His His His Ser Gly His His Thr Gly His His
1               5                   10                  15

His His Ser Gly Ser His His His Thr Gly Gly Ser Ser Gly Ser Glu
                20                  25                  30

Ser Ser Met Gln Ile Phe Val Lys Thr Leu Thr Gly Lys Thr Ile Thr
            35                  40                  45

Leu Glu Val Glu Pro Ser Asp Thr Ile Glu Asn Val Lys Ala Lys Ile
50                  55                  60

Gln Asp Lys Glu Gly Ile Pro Pro Asp Gln Gln Arg Leu Ile Phe Ala
65                  70                  75                  80

Gly Lys Gln Leu Glu Asp Gly Arg Thr Leu Ser Asp Tyr Asn Ile Gln
                85                  90                  95

Lys Glu Ser Thr Leu His Leu Val Leu Arg Leu Arg Gly Gly Ala Gly
            100                 105                 110

Thr Lys Thr Glu Glu Gly Lys Leu Val Ile Trp Ile Asn Gly Asp Lys
                115                 120                 125

Gly Tyr Asn Gly Leu Ala Glu Val Gly Lys Lys Phe Glu Lys Asp Thr
130                 135                 140

Gly Ile Lys Val Thr Val Glu His Pro Asp Lys Leu Glu Glu Lys Phe
145                 150                 155                 160

Pro Gln Val Ala Ala Thr Gly Asp Gly Pro Asp Ile Ile Phe Trp Ala
                165                 170                 175

His Asp Arg Phe Gly Gly Tyr Ala Gln Ser Gly Leu Leu Ala Glu Ile
            180                 185                 190

Thr Pro Asp Lys Ala Phe Gln Asp Lys Leu Tyr Pro Phe Thr Trp Asp
                195                 200                 205

Ala Val Arg Tyr Asn Gly Lys Leu Ile Ala Tyr Pro Ile Ala Val Glu
            210                 215                 220

Ala Leu Ser Leu Ile Tyr Asn Lys Asp Leu Leu Pro Asn Pro Pro Lys
225                 230                 235                 240
```

Thr Trp Glu Glu Ile Pro Ala Leu Asp Lys Glu Leu Lys Ala Lys Gly
            245                 250                 255

Lys Ser Ala Leu Met Phe Asn Leu Gln Glu Pro Tyr Phe Thr Trp Pro
        260                 265                 270

Leu Ile Ala Ala Asp Gly Gly Tyr Ala Phe Lys Tyr Glu Asn Gly Lys
    275                 280                 285

Tyr Asp Ile Lys Asp Val Gly Val Asp Asn Ala Gly Ala Lys Ala Gly
290                 295                 300

Leu Thr Phe Leu Val Asp Leu Ile Lys Asn Lys His Met Asn Ala Asp
305                 310                 315                 320

Thr Asp Tyr Ser Ile Ala Glu Ala Ala Phe Asn Lys Gly Glu Thr Ala
            325                 330                 335

Met Thr Ile Asn Gly Pro Trp Ala Trp Ser Asn Ile Asp Thr Ser Lys
        340                 345                 350

Val Asn Tyr Gly Val Thr Val Leu Pro Thr Phe Lys Gly Gln Pro Ser
    355                 360                 365

Lys Pro Phe Val Gly Val Leu Ser Ala Gly Ile Asn Ala Ala Ser Pro
    370                 375                 380

Asn Lys Glu Leu Ala Lys Glu Phe Leu Glu Asn Tyr Leu Leu Thr Asp
385                 390                 395                 400

Glu Gly Leu Glu Ala Val Asn Lys Asp Lys Pro Leu Gly Ala Val Ala
            405                 410                 415

Leu Lys Ser Tyr Glu Glu Leu Ala Lys Asp Pro Arg Ile Ala Ala
        420                 425                 430

Thr Met Glu Asn Ala Gln Lys Gly Glu Ile Met Pro Asn Ile Pro Gln
    435                 440                 445

Met Ser Ala Phe Trp Tyr Ala Val Arg Thr Ala Val Ile Asn Ala Ala
    450                 455                 460

Ser Gly Arg Gln Thr Val Asp Glu Ala Leu Lys Asp Ala Gln Thr Asn
465                 470                 475                 480

Gly Thr Gly Cys

<210> SEQ ID NO 10
<211> LENGTH: 77
<212> TYPE: PRT
<213> ORGANISM: Artificial
<220> FEATURE:
<223> OTHER INFORMATION: bdSUMO 21-97

<400> SEQUENCE: 10

His Ile Asn Leu Lys Val Lys Gly Gln Asp Gly Asn Glu Val Phe Phe
1               5                   10                  15

Arg Ile Lys Arg Ser Thr Gln Leu Lys Lys Leu Met Asn Ala Tyr Cys
            20                  25                  30

Asp Arg Gln Ser Val Asp Met Thr Ala Ile Ala Phe Leu Phe Asp Gly
        35                  40                  45

Arg Arg Leu Arg Ala Glu Gln Thr Pro Asp Glu Leu Glu Met Glu Asp
    50                  55                  60

Gly Asp Glu Ile Asp Ala Met Leu His Gln Thr Gly Gly
65                  70                  75

<210> SEQ ID NO 11
<211> LENGTH: 234
<212> TYPE: PRT
<213> ORGANISM: Artificial
<220> FEATURE:

<223> OTHER INFORMATION: bdSENP1 248-481

<400> SEQUENCE: 11

```
Pro Phe Val Pro Leu Thr Asp Glu Asp Glu Asp Asn Val Arg His Ala
1               5                   10                  15

Leu Gly Gly Arg Lys Arg Ser Glu Thr Leu Ser Val His Glu Ala Ser
            20                  25                  30

Asn Ile Val Ile Thr Arg Glu Ile Leu Gln Cys Leu Asn Asp Lys Glu
        35                  40                  45

Trp Leu Asn Asp Glu Val Ile Asn Leu Tyr Leu Glu Leu Leu Lys Glu
    50                  55                  60

Arg Glu Leu Arg Glu Pro Asn Lys Phe Leu Lys Cys His Phe Phe Asn
65                  70                  75                  80

Thr Phe Phe Tyr Lys Lys Leu Ile Asn Gly Gly Tyr Asp Tyr Lys Ser
                85                  90                  95

Val Arg Arg Trp Thr Thr Lys Arg Lys Leu Gly Tyr Asn Leu Ile Asp
            100                 105                 110

Cys Asp Lys Ile Phe Val Pro Ile His Lys Asp Val His Trp Cys Leu
        115                 120                 125

Ala Val Ile Asn Ile Lys Glu Lys Lys Phe Gln Tyr Leu Asp Ser Leu
    130                 135                 140

Gly Tyr Met Asp Met Lys Ala Leu Arg Ile Leu Ala Lys Tyr Leu Val
145                 150                 155                 160

Asp Glu Val Lys Asp Lys Ser Gly Lys Gln Ile Asp Val His Ala Trp
                165                 170                 175

Lys Gln Glu Gly Val Gln Asn Leu Pro Leu Gln Glu Asn Gly Trp Asp
            180                 185                 190

Cys Gly Met Phe Met Leu Lys Tyr Ile Asp Phe Tyr Ser Arg Asp Met
        195                 200                 205

Glu Leu Val Phe Gly Gln Lys His Met Ser Tyr Phe Arg Arg Arg Thr
    210                 215                 220

Ala Lys Glu Ile Leu Asp Leu Lys Ala Gly
225                 230
```

<210> SEQ ID NO 12
<211> LENGTH: 75
<212> TYPE: PRT
<213> ORGANISM: Brachypodium distachyon

<400> SEQUENCE: 12

```
Met Ile Lys Val Lys Thr Leu Thr Gly Lys Glu Ile Glu Ile Asp Ile
1               5                   10                  15

Glu Pro Thr Asp Thr Ile Asp Arg Ile Lys Glu Arg Val Glu Glu Lys
            20                  25                  30

Glu Gly Ile Pro Pro Val Gln Gln Arg Leu Ile Tyr Ala Gly Lys Gln
        35                  40                  45

Leu Ala Asp Asp Lys Thr Ala Leu Asp Tyr Asn Ile Glu Gly Gly Ser
    50                  55                  60

Val Leu His Leu Val Leu Ala Leu Arg Gly Gly
65                  70                  75
```

<210> SEQ ID NO 13
<211> LENGTH: 242
<212> TYPE: PRT
<213> ORGANISM: Brachypodium distachyon

<400> SEQUENCE: 13

```
Met Asp Glu Arg Val Leu Ser Tyr Gly Asp Val Leu Leu Arg Ser
1               5                   10                  15

Asp Leu Ala Ile Leu Arg Gly Pro His Phe Leu Asn Asp Arg Ile Ile
            20                  25                  30

Ala Phe Tyr Leu Ala His Leu Ser Ala Ser Phe His Gly Asp Gly Asp
        35                  40                  45

Leu Leu Leu Leu Pro Pro Ser Ile Pro Tyr Leu Leu Ser Asn Leu Pro
50                  55                  60

Asp Pro Glu Ser Val Ala Glu Pro Leu Cys Leu Ala Ser Arg Arg Leu
65                  70                  75                  80

Val Leu Leu Pro Val Asn Asp Asn Pro Asp Ala Ser Val Ala Asn Gly
                85                  90                  95

Gly Ser His Trp Thr Leu Leu Val Leu Asp Ala Ala Thr Thr Asp Pro
                100                 105                 110

Gln Ala Pro Arg Phe Val His His Asp Ser Leu Arg Gly Ser Ala Asn
            115                 120                 125

Ala Ala Ala Ala Arg Arg Leu Ala Arg Ala Leu Thr Ala Gly Gly Ala
        130                 135                 140

Pro Leu Arg Phe Val Glu Ala Pro Thr Pro Thr Gln Arg Asn Gly His
145                 150                 155                 160

Asp Cys Gly Val Tyr Val Leu Ala Val Ala Arg Ala Ile Cys Gly Trp
                165                 170                 175

Trp Arg Ser Ser Arg Arg Arg Glu Asn Gln Gln Gly Gly Gly Gly Asp
                180                 185                 190

Trp Phe Ala Thr Met Met Glu Glu Val Asp Ala Glu Ser Val Gly Ala
            195                 200                 205

Met Arg Ala Glu Leu Leu Gln Leu Ile His Arg Leu Ile Gln Asp Lys
        210                 215                 220

Glu Gln Glu Glu Glu Lys Lys Ser Lys Ala Gly Val Glu Asp Thr Cys
225                 230                 235                 240

Gly Gln

<210> SEQ ID NO 14
<211> LENGTH: 8
<212> TYPE: PRT
<213> ORGANISM: Artificial
<220> FEATURE:
<223> OTHER INFORMATION: TEV protease recognition site-spacer fusion
<220> FEATURE:
<221> NAME/KEY: MISC_FEATURE
<222> LOCATION: (1)..(7)
<223> OTHER INFORMATION: TEV protease minimum recognition site
<220> FEATURE:
<221> NAME/KEY: MISC_FEATURE
<222> LOCATION: (8)..(8)
<223> OTHER INFORMATION: spacer

<400> SEQUENCE: 14

Glu Asn Leu Tyr Phe Gln Gly Thr
1               5

<210> SEQ ID NO 15
<211> LENGTH: 242
<212> TYPE: PRT
<213> ORGANISM: Tobacco etch virus

<400> SEQUENCE: 15

Gly Glu Ser Leu Phe Lys Gly Pro Arg Asp Tyr Asn Pro Ile Ser Ser
1               5                   10                  15
```

Thr Ile Cys His Leu Thr Asn Glu Ser Asp Gly His Thr Thr Ser Leu
                20                  25                  30

Tyr Gly Ile Gly Phe Gly Pro Phe Ile Ile Thr Asn Lys His Leu Phe
            35                  40                  45

Arg Arg Asn Asn Gly Thr Leu Leu Val Gln Ser Leu His Gly Val Phe
50                      55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Ser Lys Pro Glu Glu Pro
210                 215                 220

Phe Gln Pro Val Lys Glu Ala Thr Gln Leu Met Asn Glu Leu Val Tyr
225                 230                 235                 240

Ser Gln

<210> SEQ ID NO 16
<211> LENGTH: 235
<212> TYPE: PRT
<213> ORGANISM: Artificial
<220> FEATURE:
<223> OTHER INFORMATION: TEV(SH)deltaC6

<400> SEQUENCE: 16

Glu Ser Leu Phe Lys Gly Pro Arg Asp Tyr Asn Pro Ile Ser Ser Ser
1               5                   10                  15

Ile Cys His Leu Thr Asn Glu Ser Asp Gly His Thr Thr Ser Leu Tyr
                20                  25                  30

Gly Ile Gly Phe Gly Pro Phe Ile Ile Thr Asn Lys His Leu Phe Arg
            35                  40                  45

Arg Asn Asn Gly Thr Leu Leu Val Gln Ser Leu His Gly Val Phe Lys
50                  55                  60

Val Lys Asp Thr Thr Thr Leu Gln Gln His Leu Val Asp Gly Arg Asp
65                  70                  75                  80

Met Ile Ile Ile Arg Met Pro Lys Asp Phe Pro Pro Phe Pro Gln Lys
                85                  90                  95

Leu Lys Phe Arg Glu Pro Gln Arg Glu Glu Arg Ile Cys Leu Val Thr
            100                 105                 110

Thr Asn Phe Gln Thr Lys Ser Met Ser Ser Met Val Ser Asp Thr Ser
        115                 120                 125

```
Cys Thr Phe Pro Ser Ser Asp Gly Ile Phe Trp Lys His Trp Ile Gln
        130                 135                 140

Thr Lys Asp Gly Gln Cys Gly Ser Pro Leu Val Ser Thr Arg Asp Gly
145                 150                 155                 160

Phe Ile Val Gly Ile His Ser Ala Ser Asn Phe Thr Asn Thr Asn Asn
                165                 170                 175

Tyr Phe Thr Ser Val Pro Lys Asn Phe Met Glu Leu Leu Thr Asn Gln
                180                 185                 190

Glu Ala Gln Gln Trp Val Ser Gly Trp Arg Leu Asn Ala Asp Ser Val
            195                 200                 205

Leu Trp Gly Gly His Lys Val Phe Met Asn Lys Pro Glu Glu Pro Phe
210                 215                 220

Gln Pro Val Lys Glu Ala Thr Gln Leu Met Asn
225                 230                 235

<210> SEQ ID NO 17
<211> LENGTH: 76
<212> TYPE: PRT
<213> ORGANISM: Xenopus laevis

<400> SEQUENCE: 17

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
50                  55                  60

Ser Thr Leu His Leu Val Leu Arg Leu Arg Gly Gly
65                  70                  75

<210> SEQ ID NO 18
<211> LENGTH: 383
<212> TYPE: PRT
<213> ORGANISM: Xenopus laevis

<400> SEQUENCE: 18

Met Arg Ser His Thr Leu Arg Ile His Gly Met Gly Ala Gly Arg Glu
1               5                   10                  15

His Gln Ile Pro Gly Thr Val Ile Leu Ser Ser Ile Met Asp Phe Ile
                20                  25                  30

Leu His Arg Ala Lys Ser Ser Lys His Val Gln Gly Leu Val Gly Leu
            35                  40                  45

Arg Asn Leu Gly Asn Thr Cys Phe Met Asn Ser Ile Leu Gln Cys Leu
50                  55                  60

Ser Asn Thr Lys Asp Leu Arg Asp Tyr Cys Gln Gln Asn Ser Tyr Arg
65                  70                  75                  80

Arg Asp Leu Ser Ser Lys Lys Cys Asn Thr Ala Ile Met Glu Glu Phe
                85                  90                  95

Ala Arg Leu Leu Gln Ala Ile Trp Thr Ser Ser Ala Asn Glu Val Val
            100                 105                 110

Ser Pro Ser Glu Phe Lys Thr Gln Ile Gln Arg Tyr Ala Pro Arg Phe
        115                 120                 125

Met Gly Tyr Asn Gln Gln Asp Ala Gln Glu Phe Leu Arg Phe Leu Leu
    130                 135                 140
```

Asp Gly Leu His Asn Glu Val Asn Arg Val Thr Val Lys Pro Arg Pro
145                 150                 155                 160

Ser Ser Gln Asp Leu Asp His Met Pro Asp Ser Glu Lys Gly Lys Lys
            165                 170                 175

Met Trp Lys Arg Tyr Leu Glu Arg Glu Asp Ser Arg Ile Val Glu Leu
            180                 185                 190

Phe Val Gly Gln Leu Lys Ser Ser Leu Thr Cys Thr Asp Cys Gly Tyr
            195                 200                 205

Cys Ser Thr Val Phe Asp Pro Phe Trp Asp Leu Ser Leu Pro Ile Ala
        210                 215                 220

Lys Lys Ser Ala Ser Glu Val Ser Leu Val Asp Cys Met Arg Leu Phe
225                 230                 235                 240

Thr Lys Glu Asp Val Leu Asp Gly Asp Glu Lys Pro Thr Cys Cys Arg
                245                 250                 255

Cys Lys Ala Arg Arg Arg Cys Thr Lys Lys Phe Thr Ile Gln Arg Phe
            260                 265                 270

Pro Lys Ile Leu Val Leu His Leu Lys Arg Phe Ser Glu Gly Arg Ile
            275                 280                 285

Arg Ser Gly Lys Leu Ser Thr Phe Val Asn Phe Pro Leu Lys Asp Leu
290                 295                 300

Asp Leu Arg Glu Phe Ser Ser Glu Ser Asn Pro His Ala Thr Tyr Asn
305                 310                 315                 320

Leu Tyr Ala Val Ser Asn His Ser Gly Thr Thr Met Gly Gly His Tyr
                325                 330                 335

Thr Ala Tyr Cys Lys Asn Pro Ser Asn Gly Glu Trp Tyr Thr Phe Asn
            340                 345                 350

Asp Ser Arg Val Thr Ala Met Ser Ser Gln Val Lys Ser Ser Asp
            355                 360                 365

Ala Tyr Val Leu Phe Tyr Glu Leu Ser Gly Pro Ser Ser Arg Met
370                 375                 380

<210> SEQ ID NO 19
<211> LENGTH: 393
<212> TYPE: PRT
<213> ORGANISM: Homo sapiens

<400> SEQUENCE: 19

Met Asp Ala Ala Thr Leu Thr Tyr Asp Thr Leu Arg Phe Ala Glu Phe
1               5                   10                  15

Glu Asp Phe Pro Glu Thr Ser Glu Pro Val Trp Ile Leu Gly Arg Lys
            20                  25                  30

Tyr Ser Ile Phe Thr Glu Lys Asp Glu Ile Leu Ser Asp Val Ala Ser
        35                  40                  45

Arg Leu Trp Phe Thr Tyr Arg Lys Asn Phe Pro Ala Ile Gly Gly Thr
50                  55                  60

Gly Pro Thr Ser Asp Thr Gly Trp Gly Cys Met Leu Arg Cys Gly Gln
65                  70                  75                  80

Met Ile Phe Ala Gln Ala Leu Val Cys Arg His Leu Gly Arg Asp Trp
                85                  90                  95

Arg Trp Thr Gln Arg Lys Arg Gln Pro Asp Ser Tyr Phe Ser Val Leu
            100                 105                 110

Asn Ala Phe Ile Asp Arg Lys Asp Ser Tyr Tyr Ser Ile His Gln Ile
        115                 120                 125

Ala Gln Met Gly Val Gly Glu Gly Lys Ser Ile Gly Gln Trp Tyr Gly
130                 135                 140

```
Pro Asn Thr Val Ala Gln Val Leu Lys Lys Leu Ala Val Phe Asp Thr
145                 150                 155                 160

Trp Ser Ser Leu Ala Val His Ile Ala Met Asp Asn Thr Val Val Met
            165                 170                 175

Glu Glu Ile Arg Arg Leu Cys Arg Thr Ser Val Pro Cys Ala Gly Ala
        180                 185                 190

Thr Ala Phe Pro Ala Asp Ser Asp Arg His Cys Asn Gly Phe Pro Ala
    195                 200                 205

Gly Ala Glu Val Thr Asn Arg Pro Ser Pro Trp Arg Pro Leu Val Leu
210                 215                 220

Leu Ile Pro Leu Arg Leu Gly Leu Thr Asp Ile Asn Glu Ala Tyr Val
225                 230                 235                 240

Glu Thr Leu Lys His Cys Phe Met Met Pro Gln Ser Leu Gly Val Ile
                245                 250                 255

Gly Gly Lys Pro Asn Ser Ala His Tyr Phe Ile Gly Tyr Val Gly Glu
            260                 265                 270

Glu Leu Ile Tyr Leu Asp Pro His Thr Thr Gln Pro Ala Val Glu Pro
        275                 280                 285

Thr Asp Gly Cys Phe Ile Pro Asp Glu Ser Phe His Cys Gln His Pro
290                 295                 300

Pro Cys Arg Met Ser Ile Ala Glu Leu Asp Pro Ser Ile Ala Val Gly
305                 310                 315                 320

Phe Phe Cys Lys Thr Glu Asp Asp Phe Asn Asp Trp Cys Gln Gln Val
                325                 330                 335

Lys Lys Leu Ser Leu Leu Gly Gly Ala Leu Pro Met Phe Glu Leu Val
            340                 345                 350

Glu Leu Gln Pro Ser His Leu Ala Cys Pro Asp Val Leu Asn Leu Ser
        355                 360                 365

Leu Asp Ser Ser Asp Val Glu Arg Leu Glu Arg Phe Phe Asp Ser Glu
370                 375                 380

Asp Glu Asp Phe Glu Ile Leu Ser Leu
385                 390

<210> SEQ ID NO 20
<211> LENGTH: 120
<212> TYPE: PRT
<213> ORGANISM: Homo sapiens

<400> SEQUENCE: 20

Met Pro Ser Glu Lys Thr Phe Lys Gln Arg Arg Ser Phe Glu Gln Arg
1               5                   10                  15

Val Glu Asp Val Arg Leu Ile Arg Glu Gln His Pro Thr Lys Ile Pro
            20                  25                  30

Val Ile Ile Glu Arg Tyr Lys Gly Glu Lys Gln Leu Pro Val Leu Asp
        35                  40                  45

Lys Thr Lys Phe Leu Val Pro Asp His Val Asn Met Ser Glu Leu Ile
50                  55                  60

Lys Ile Ile Arg Arg Arg Leu Gln Leu Asn Ala Asn Gln Ala Phe Phe
65                  70                  75                  80

Leu Leu Val Asn Gly His Ser Met Val Ser Val Ser Thr Pro Ile Ser
                85                  90                  95

Glu Val Tyr Glu Ser Glu Arg Asp Glu Asp Gly Phe Leu Tyr Met Val
            100                 105                 110

Tyr Ala Ser Gln Glu Thr Phe Gly
        115                 120
```

<210> SEQ ID NO 21
<211> LENGTH: 116
<212> TYPE: PRT
<213> ORGANISM: Homo sapiens

<400> SEQUENCE: 21

Met Lys Trp Met Phe Lys Glu Asp His Ser Leu Glu His Arg Cys Val
1               5                   10                  15

Glu Ser Ala Lys Ile Arg Ala Lys Tyr Pro Asp Arg Val Pro Val Ile
            20                  25                  30

Val Glu Lys Val Ser Gly Ser Gln Ile Val Asp Ile Asp Lys Arg Lys
        35                  40                  45

Tyr Leu Val Pro Ser Asp Ile Thr Val Ala Gln Phe Met Trp Ile Ile
    50                  55                  60

Arg Lys Arg Ile Gln Leu Pro Ser Glu Lys Ala Ile Phe Leu Phe Val
65                  70                  75                  80

Asp Lys Thr Val Pro Gln Ser Ser Leu Thr Met Gly Gln Leu Tyr Glu
                85                  90                  95

Lys Glu Lys Asp Glu Asp Gly Phe Leu Tyr Val Ala Tyr Ser Gly Glu
            100                 105                 110

Asn Thr Phe Gly
        115

<210> SEQ ID NO 22
<211> LENGTH: 497
<212> TYPE: PRT
<213> ORGANISM: Artificial
<220> FEATURE:
<223> OTHER INFORMATION: His14-SUMOstar-MBP

<400> SEQUENCE: 22

Met Ser Lys His His His His Ser Gly His His His Thr Gly His His
1               5                   10                  15

His His Ser Gly Ser His His His Thr Gly Ser Asp Ser Glu Val Asn
            20                  25                  30

Gln Glu Ala Lys Pro Glu Val Lys Pro Glu Val Lys Pro Glu Thr His
        35                  40                  45

Ile Asn Leu Lys Val Ser Asp Gly Ser Ser Glu Ile Phe Phe Lys Ile
    50                  55                  60

Lys Lys Thr Thr Pro Leu Arg Arg Leu Met Glu Ala Phe Ala Lys Arg
65                  70                  75                  80

Gln Gly Lys Glu Met Asp Ser Leu Thr Phe Leu Tyr Asp Gly Ile Glu
                85                  90                  95

Ile Gln Ala Asp Gln Thr Pro Glu Asp Leu Asp Met Glu Asp Asn Asp
            100                 105                 110

Ile Ile Glu Ala His Arg Glu Gln Ile Gly Gly Ala Gly Thr Lys Thr
        115                 120                 125

Glu Glu Gly Lys Leu Val Ile Trp Ile Asn Gly Asp Lys Gly Tyr Asn
    130                 135                 140

Gly Leu Ala Glu Val Gly Lys Lys Phe Glu Lys Asp Thr Gly Ile Lys
145                 150                 155                 160

Val Thr Val Glu His Pro Asp Lys Leu Glu Glu Lys Phe Pro Gln Val
                165                 170                 175

Ala Ala Thr Gly Asp Gly Pro Asp Ile Ile Phe Trp Ala His Asp Arg
            180                 185                 190

```
Phe Gly Gly Tyr Ala Gln Ser Gly Leu Leu Ala Glu Ile Thr Pro Asp
        195                 200                 205

Lys Ala Phe Gln Asp Lys Leu Tyr Pro Phe Thr Trp Asp Ala Val Arg
        210                 215                 220

Tyr Asn Gly Lys Leu Ile Ala Tyr Pro Ile Ala Val Glu Ala Leu Ser
225                 230                 235                 240

Leu Ile Tyr Asn Lys Asp Leu Leu Pro Asn Pro Pro Lys Thr Trp Glu
                245                 250                 255

Glu Ile Pro Ala Leu Asp Lys Glu Leu Lys Ala Lys Gly Lys Ser Ala
                260                 265                 270

Leu Met Phe Asn Leu Gln Glu Pro Tyr Phe Thr Trp Pro Leu Ile Ala
                275                 280                 285

Ala Asp Gly Gly Tyr Ala Phe Lys Tyr Glu Asn Gly Lys Tyr Asp Ile
        290                 295                 300

Lys Asp Val Gly Val Asp Asn Ala Gly Ala Lys Ala Gly Leu Thr Phe
305                 310                 315                 320

Leu Val Asp Leu Ile Lys Asn Lys His Met Asn Ala Asp Thr Asp Tyr
                325                 330                 335

Ser Ile Ala Glu Ala Ala Phe Asn Lys Gly Glu Thr Ala Met Thr Ile
                340                 345                 350

Asn Gly Pro Trp Ala Trp Ser Asn Ile Asp Thr Ser Lys Val Asn Tyr
                355                 360                 365

Gly Val Thr Val Leu Pro Thr Phe Lys Gly Gln Pro Ser Lys Pro Phe
        370                 375                 380

Val Gly Val Leu Ser Ala Gly Ile Asn Ala Ala Ser Pro Asn Lys Glu
385                 390                 395                 400

Leu Ala Lys Glu Phe Leu Glu Asn Tyr Leu Leu Thr Asp Glu Gly Leu
                405                 410                 415

Glu Ala Val Asn Lys Asp Lys Pro Leu Gly Ala Val Ala Leu Lys Ser
                420                 425                 430

Tyr Glu Glu Glu Leu Ala Lys Asp Pro Arg Ile Ala Ala Thr Met Glu
        435                 440                 445

Asn Ala Gln Lys Gly Glu Ile Met Pro Asn Ile Pro Gln Met Ser Ala
        450                 455                 460

Phe Trp Tyr Ala Val Arg Thr Ala Val Ile Asn Ala Ala Ser Gly Arg
465                 470                 475                 480

Gln Thr Val Asp Glu Ala Leu Lys Asp Ala Gln Thr Asn Gly Thr Gly
                485                 490                 495

Cys

<210> SEQ ID NO 23
<211> LENGTH: 98
<212> TYPE: PRT
<213> ORGANISM: Artificial
<220> FEATURE:
<223> OTHER INFORMATION: SUMOstar

<400> SEQUENCE: 23

Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
                35                  40                  45
```

```
Met Glu Ala Phe Ala Lys Arg Gln Gly Lys Glu Met Asp Ser Leu Thr
     50                  55                  60

Phe Leu Tyr Asp Gly Ile Glu Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 24
<211> LENGTH: 219
<212> TYPE: PRT
<213> ORGANISM: Artificial
<220> FEATURE:
<223> OTHER INFORMATION: SUMOstar protease

<400> SEQUENCE: 24

Leu Val Pro Glu Leu Asn Glu Lys Asp Asp Gln Val Gln Lys Ala
 1               5                  10                  15

Leu Ala Ser Arg Glu Asn Thr Gln Leu Met Asn Arg Asp Asn Ile Glu
                 20                  25                  30

Ile Thr Val Arg Asp Phe Lys Thr Leu Ala Pro Arg Arg Trp Leu Asn
                 35                  40                  45

Asp Thr Ile Ile Glu Phe Phe Met Lys Tyr Ile Glu Lys Ser Thr Pro
 50                  55                  60

Asn Thr Val Ala Phe Asn Ser Phe Phe Tyr Thr Asn Leu Ser Glu Arg
 65                  70                  75                  80

Gly Tyr Gln Gly Val Arg Arg Trp Met Lys Arg Lys Thr Gln Ile
                 85                  90                  95

Asp Lys Leu Asp Lys Ile Phe Thr Pro Ile Asn Leu Asn Gln Ser His
                 100                 105                 110

Trp Ala Leu Gly Ile Ile Asp Leu Lys Lys Lys Thr Ile Gly Tyr Val
                 115                 120                 125

Asp Ser Leu Ser Asn Gly Pro Asn Ala Met Ser Phe Ala Ile Leu Thr
 130                 135                 140

Asp Leu Gln Lys Tyr Val Met Glu Glu Ser Lys His Thr Ile Gly Glu
145                  150                 155                 160

Asp Phe Asp Leu Ile His Leu Asp Cys Pro Gln Gln Pro Asn Gly Tyr
                 165                 170                 175

Asp Cys Gly Ile Tyr Val Cys Met Asn Thr Leu Tyr Gly Ser Ala Asp
                 180                 185                 190

Ala Pro Leu Asp Phe Asp Tyr Lys Asp Ala Ile Arg Met Arg Arg Phe
                 195                 200                 205

Ile Ala His Leu Ile Leu Thr Asp Ala Leu Lys
 210                 215

<210> SEQ ID NO 25
<211> LENGTH: 681
<212> TYPE: PRT
<213> ORGANISM: Artificial
<220> FEATURE:
<223> OTHER INFORMATION: His14-IF2d1-xlLC3B-MBP

<400> SEQUENCE: 25

Met Ser Lys His His His His Ser Gly His His Thr Gly His His
 1               5                  10                  15

His His Ser Gly Ser His His Thr Gly Gly Ser Ser Gly Thr Asp
                 20                  25                  30
```

```
Val Thr Ile Lys Thr Leu Ala Ala Glu Arg Gln Thr Ser Val Glu Arg
         35                  40                  45

Leu Val Gln Gln Phe Ala Asp Ala Gly Ile Arg Lys Ser Ala Asp Asp
 50                  55                  60

Ser Val Ser Ala Gln Glu Lys Gln Thr Leu Ile Asp His Leu Asn Gln
 65                  70                  75                  80

Lys Asn Ser Gly Pro Asp Lys Leu Thr Leu Gln Arg Lys Thr Arg Ser
                 85                  90                  95

Thr Leu Asn Ile Pro Gly Thr Gly Gly Lys Ser Lys Ser Val Gln Ile
             100                 105                 110

Glu Val Arg Lys Lys Arg Thr Phe Val Lys Arg Asp Pro Gln Glu Ala
             115                 120                 125

Glu Arg Leu Ala Ala Glu Glu Ala Gln Arg Glu Ala Glu Glu Gln
             130                 135                 140

Ala Arg Arg Glu Ala Glu Glu Ser Ala Lys Arg Glu Ala Gln Gln Lys
145                 150                 155                 160

Ala Glu Arg Glu Ala Ala Glu Gln Ala Lys Arg Glu Ala Ala Glu Gln
                 165                 170                 175

Ala Lys Arg Glu Ala Ala Glu Lys Asp Lys Val Thr Ser Ser Glu Lys
             180                 185                 190

Thr Phe Lys Gln Arg Arg Ser Leu Glu Gln Arg Val Glu Asp Val Arg
             195                 200                 205

Leu Ile Arg Glu Gln His Pro Thr Lys Ile Pro Val Ile Glu Arg
 210                 215                 220

Tyr Lys Gly Glu Lys Gln Leu Pro Val Leu Asp Lys Thr Lys Phe Leu
225                 230                 235                 240

Val Pro Asp His Val Asn Met Ser Glu Leu Ile Lys Ile Ile Arg Arg
                 245                 250                 255

Arg Leu Gln Leu Asn Ser Asn Gln Ala Phe Phe Leu Leu Val Asn Gly
             260                 265                 270

His Ser Met Val Ser Val Ser Thr Pro Ile Ser Glu Val Tyr Glu Arg
             275                 280                 285

Glu Lys Asp Glu Asp Gly Phe Leu Tyr Met Val Tyr Ala Ser Gln Glu
             290                 295                 300

Thr Phe Gly Ala Gly Thr Lys Thr Glu Glu Gly Lys Leu Val Ile Trp
305                 310                 315                 320

Ile Asn Gly Asp Lys Gly Tyr Asn Gly Leu Ala Glu Val Gly Lys Lys
                 325                 330                 335

Phe Glu Lys Asp Thr Gly Ile Lys Val Thr Val Glu His Pro Asp Lys
             340                 345                 350

Leu Glu Glu Lys Phe Pro Gln Val Ala Ala Thr Gly Asp Gly Pro Asp
             355                 360                 365

Ile Ile Phe Trp Ala His Asp Arg Phe Gly Gly Tyr Ala Gln Ser Gly
 370                 375                 380

Leu Leu Ala Glu Ile Thr Pro Asp Lys Ala Phe Gln Asp Lys Leu Tyr
385                 390                 395                 400

Pro Phe Thr Trp Asp Ala Val Arg Tyr Asn Gly Lys Leu Ile Ala Tyr
                 405                 410                 415

Pro Ile Ala Val Glu Ala Leu Ser Leu Ile Tyr Asn Lys Asp Leu Leu
             420                 425                 430

Pro Asn Pro Pro Lys Thr Trp Glu Glu Ile Pro Ala Leu Asp Lys Glu
             435                 440                 445

Leu Lys Ala Lys Gly Lys Ser Ala Leu Met Phe Asn Leu Gln Glu Pro
```

```
                    450             455             460
Tyr Phe Thr Trp Pro Leu Ile Ala Ala Asp Gly Gly Tyr Ala Phe Lys
465                 470                 475                 480

Tyr Glu Asn Gly Lys Tyr Asp Ile Lys Asp Val Gly Val Asp Asn Ala
                485                 490                 495

Gly Ala Lys Ala Gly Leu Thr Phe Leu Val Asp Leu Ile Lys Asn Lys
                500                 505                 510

His Met Asn Ala Asp Thr Asp Tyr Ser Ile Ala Glu Ala Ala Phe Asn
                515                 520                 525

Lys Gly Glu Thr Ala Met Thr Ile Asn Gly Pro Trp Ala Trp Ser Asn
                530                 535                 540

Ile Asp Thr Ser Lys Val Asn Tyr Gly Val Thr Val Leu Pro Thr Phe
545                 550                 555                 560

Lys Gly Gln Pro Ser Lys Pro Phe Val Gly Val Leu Ser Ala Gly Ile
                565                 570                 575

Asn Ala Ala Ser Pro Asn Lys Glu Leu Ala Lys Glu Phe Leu Glu Asn
                580                 585                 590

Tyr Leu Leu Thr Asp Glu Gly Leu Glu Ala Val Asn Lys Asp Lys Pro
                595                 600                 605

Leu Gly Ala Val Ala Leu Lys Ser Tyr Glu Glu Glu Leu Ala Lys Asp
                610                 615                 620

Pro Arg Ile Ala Ala Thr Met Glu Asn Ala Gln Lys Gly Glu Ile Met
625                 630                 635                 640

Pro Asn Ile Pro Gln Met Ser Ala Phe Trp Tyr Ala Val Arg Thr Ala
                645                 650                 655

Val Ile Asn Ala Ala Ser Gly Arg Gln Thr Val Asp Glu Ala Leu Lys
                660                 665                 670

Asp Ala Gln Thr Asn Gly Thr Gly Cys
                675                 680
```